(12) United States Patent
Lopes et al.

(10) Patent No.: US 11,896,295 B2
(45) Date of Patent: Feb. 13, 2024

(54) HIGH-DENSITY ELECTRODE-BASED MEDICAL DEVICE SYSTEM

(71) Applicant: Kardium Inc., Burnaby (CA)

(72) Inventors: Fernando Luis de Souza Lopes, Delta (CA); Saar Moisa, Vancouver (CA); Peter Josiah Hawes, Burnaby (CA)

(73) Assignee: KARDIUM INC., Burnaby (CA)

( * ) Notice: Subject to any disclaimer, the term of this patent is extended or adjusted under 35 U.S.C. 154(b) by 1051 days.

(21) Appl. No.: 16/655,775

(22) Filed: Oct. 17, 2019

(65) Prior Publication Data

US 2020/0046425 A1 Feb. 13, 2020

Related U.S. Application Data

(63) Continuation of application No. 15/287,988, filed on Oct. 7, 2016, now Pat. No. 11,259,867, which is a
(Continued)

(51) Int. Cl.
*A61B 18/14* (2006.01)
*A61B 5/00* (2006.01)
(Continued)

(52) U.S. Cl.
CPC .......... *A61B 18/1492* (2013.01); *A61B 5/287* (2021.01); *A61B 5/6858* (2013.01);
(Continued)

(58) Field of Classification Search
CPC ... A61B 18/1492; A61B 5/287; A61B 5/6858; A61B 5/283; A61B 5/0538;
(Continued)

(56) References Cited

U.S. PATENT DOCUMENTS 4,114,202 A 9/1978 Roy et al.
4,164,046 A 8/1979 Cooley
(Continued)

FOREIGN PATENT DOCUMENTS

CN 101797181 A 8/2010
DE 102010026210 A1 1/2012
(Continued)

OTHER PUBLICATIONS

Buchbinder, Maurice Md, "Dynamic Mitral Valve Annuloplasty: A Reshapable Ring for Residual and Recurring MR," from the Foundation for Cardiovascular Medicine, La Jolla, CA. May 24, 2007.
(Continued)

*Primary Examiner* — Adam Z Minchella
(74) *Attorney, Agent, or Firm* — ROSSI, KIMMS & McDOWELL LLP

(57) ABSTRACT

A medical device system is disclosed including a high-density arrangement of transducers, which may be configured to ablate, stimulate, or sense characteristics of tissue inside a bodily cavity, such as an intra-cardiac cavity. High-density arrangements of transducers may be achieved, at least in part, by overlapping elongate members on which the transducers are located, and varying sizes, shapes, or both of the transducers, especially in view of the overlapping of the elongate members. Also, the high-density arrangements of transducers may be achieved, at least in part, by including one or more recessed portions in an elongate member in order to expose one or more transducers on an underlying elongate member in a region adjacent an elongate-member-overlap region.

40 Claims, 14 Drawing Sheets

Related U.S. Application Data continuation of application No. 13/793,213, filed on Mar. 11, 2013, now Pat. No. 9,480,525, which is a continuation-in-part of application No. PCT/US2012/022061, filed on Jan. 20, 2012, and a continuation-in-part of application No. PCT/US2012/022062, filed on Jan. 20, 2012.

(60) Provisional application No. 61/734,750, filed on Dec. 7, 2012, provisional application No. 61/723,311, filed on Nov. 6, 2012, provisional application No. 61/670,881, filed on Jul. 12, 2012, provisional application No. 61/649,734, filed on May 21, 2012, provisional application No. 61/515,141, filed on Aug. 4, 2011, provisional application No. 61/488,639, filed on May 20, 2011, provisional application No. 61/485,987, filed on May 13, 2011, provisional application No. 61/435,213, filed on Jan. 21, 2011.

(51) Int. Cl.
*A61B 5/287* (2021.01)
*A61B 18/00* (2006.01)
*A61N 1/05* (2006.01)
*A61B 5/0538* (2021.01)

(52) U.S. Cl.
CPC ............ *A61B 5/0538* (2013.01); *A61B 5/6885* (2013.01); *A61B 2018/0016* (2013.01); *A61B 2018/00208* (2013.01); *A61B 2018/00267* (2013.01); *A61B 2018/00357* (2013.01); *A61B 2018/00577* (2013.01); *A61B 2018/1407* (2013.01); *A61B 2018/1417* (2013.01); *A61B 2018/1467* (2013.01); *A61B 2018/1475* (2013.01); *A61B 2562/0271* (2013.01); *A61B 2562/04* (2013.01); *A61B 2562/046* (2013.01); *A61N 1/056* (2013.01)

(58) Field of Classification Search
CPC .......... A61B 5/6885; A61B 2018/0016; A61B 2018/00208; A61B 2018/00267; A61B 2018/00357; A61B 2018/00577; A61B 2018/1407; A61B 2018/1417; A61B 2018/1467; A61B 2018/1475; A61B 2562/0271; A61B 2562/04; A61B 2562/046; A61N 1/056
See application file for complete search history.

(56) References Cited

U.S. PATENT DOCUMENTS

| | | |
|---|---|---|
| 4,225,148 A | 9/1980 | Andersson |
| 4,240,441 A | 12/1980 | Khalil |
| 4,263,680 A | 4/1981 | Reul et al. |
| 4,273,128 A | 6/1981 | Lary |
| 4,411,266 A | 10/1983 | Cosman |
| 4,490,859 A | 1/1985 | Black et al. |
| 4,543,090 A | 9/1985 | McCoy |
| 4,576,182 A | 3/1986 | Normann |
| 4,699,147 A | 10/1987 | Chilson et al. |
| 4,770,187 A | 9/1988 | Lash et al. |
| 4,787,369 A | 11/1988 | Allred, III et al. |
| 4,794,912 A | 1/1989 | Lia |
| 4,850,957 A | 7/1989 | Summers |
| 4,887,613 A | 12/1989 | Farr et al. |
| 4,890,602 A | 1/1990 | Hake |
| 4,890,612 A | 1/1990 | Kensey |
| 4,893,613 A | 1/1990 | Hake |
| 4,895,166 A | 1/1990 | Farr et al. |
| 4,905,667 A | 3/1990 | Foerster et al. |
| 4,921,499 A | 5/1990 | Hoffman et al. |
| 4,940,064 A | 7/1990 | Desai |
| 4,942,788 A | 7/1990 | Farr et al. |
| 4,979,514 A | 12/1990 | Sekii et al. |
| 4,998,933 A | 3/1991 | Eggers et al. |
| 5,026,384 A | 6/1991 | Farr et al. |
| 5,047,047 A | 9/1991 | Yoon |
| 5,122,137 A | 6/1992 | Lennox |
| 5,127,902 A | 7/1992 | Fischell |
| 5,153,151 A | 10/1992 | Aitken |
| 5,156,151 A * | 10/1992 | Imran .................... A61N 1/056 600/375 |
| 5,174,299 A | 12/1992 | Nelson |
| 5,176,693 A | 1/1993 | Pannek, Jr. |
| 5,178,620 A | 1/1993 | Eggers et al. |
| 5,192,291 A | 3/1993 | Pannek, Jr. |
| 5,195,505 A | 3/1993 | Josefsen |
| 5,201,316 A | 4/1993 | Pomeranz et al. |
| 5,228,442 A | 7/1993 | Imran |
| 5,242,386 A | 9/1993 | Holzer |
| 5,245,987 A | 9/1993 | Redmond et al. |
| 5,255,679 A | 10/1993 | Imran |
| 5,279,299 A | 1/1994 | Imran |
| 5,293,869 A | 3/1994 | Edwards et al. |
| 5,297,549 A | 3/1994 | Beatty et al. |
| 5,309,910 A | 5/1994 | Edwards et al. |
| 5,311,866 A | 5/1994 | Kagan |
| 5,312,435 A | 5/1994 | Nash et al. |
| 5,317,952 A | 6/1994 | Immega |
| 5,324,284 A | 6/1994 | Imran |
| 5,327,889 A | 7/1994 | Imran |
| 5,341,807 A | 8/1994 | Nardella |
| 5,345,936 A | 9/1994 | Pomeranz et al. |
| 5,351,551 A | 10/1994 | Drubetsky |
| 5,351,679 A | 10/1994 | Mayzels et al. |
| 5,366,443 A | 11/1994 | Eggers et al. |
| 5,370,679 A | 12/1994 | Atlee, III |
| 5,379,773 A | 1/1995 | Hornsby |
| 5,397,321 A | 3/1995 | Houser et al. |
| 5,419,767 A | 5/1995 | Eggers et al. |
| 5,450,860 A | 9/1995 | O'Connor |
| 5,456,254 A | 10/1995 | Pietroski et al. |
| 5,462,545 A | 10/1995 | Wang |
| 5,465,717 A | 11/1995 | Imran et al. |
| 5,478,353 A | 12/1995 | Yoon |
| 5,485,849 A | 1/1996 | Panescu et al. |
| 5,496,267 A | 3/1996 | Drasler et al. |
| 5,496,330 A | 3/1996 | Bates |
| 5,499,981 A | 3/1996 | Kordis |
| 5,531,760 A | 7/1996 | Alwafaie |
| 5,545,193 A | 8/1996 | Fleischman et al. |
| 5,549,108 A | 8/1996 | Edwards et al. |
| 5,549,661 A | 8/1996 | Kordis et al. |
| 5,555,883 A | 9/1996 | Avitall |
| 5,557,967 A | 9/1996 | Renger |
| 5,575,810 A | 11/1996 | Swanson et al. |
| 5,577,509 A | 11/1996 | Panescu |
| 5,593,424 A | 1/1997 | Northrup, III |
| 5,595,183 A | 1/1997 | Swanson |
| 5,598,848 A | 2/1997 | Swanson et al. |
| 5,599,345 A | 2/1997 | Edwards et al. |
| 5,620,481 A | 4/1997 | Desai et al. |
| 5,630,813 A | 5/1997 | Kieturakis |
| 5,636,634 A | 6/1997 | Kordis |
| 5,637,090 A | 6/1997 | McGee et al. |
| 5,662,587 A | 9/1997 | Grundfest et al. |
| 5,681,308 A | 10/1997 | Edwards et al. |
| 5,681,336 A | 10/1997 | Clement et al. |
| 5,687,723 A | 11/1997 | Avitall |
| 5,687,737 A | 11/1997 | Branham et al. |
| 5,697,285 A | 12/1997 | Nappi et al. |
| 5,704,914 A | 1/1998 | Stocking |
| 5,713,896 A | 2/1998 | Nardella |
| 5,713,942 A | 2/1998 | Stern et al. |
| 5,716,397 A | 2/1998 | Myers |
| 5,718,241 A | 2/1998 | Ben-Haim |
| 5,720,726 A | 2/1998 | Marcadis et al. |
| 5,728,114 A | 3/1998 | Evans et al. |
| 5,730,127 A | 3/1998 | Avitall |
| 5,738,096 A | 4/1998 | Ben-Haim |

(56) References Cited

U.S. PATENT DOCUMENTS

| | | | |
|---|---|---|---|
| 5,762,066 A | 6/1998 | Law et al. | |
| 5,769,846 A | 6/1998 | Edwards et al. | |
| 5,782,239 A | 7/1998 | Webster, Jr. | |
| 5,782,879 A | 7/1998 | Rosborough et al. | |
| 5,800,495 A | 9/1998 | Machek et al. | |
| 5,823,189 A | 10/1998 | Kordis | |
| 5,824,066 A | 10/1998 | Gross | |
| 5,831,159 A | 11/1998 | Renger | |
| 5,836,947 A | 11/1998 | Fleischman et al. | |
| 5,836,990 A | 11/1998 | Li | |
| 5,853,422 A | 12/1998 | Huebsch et al. | |
| 5,868,743 A | 2/1999 | Saul | |
| 5,868,755 A | 2/1999 | Kanner et al. | |
| 5,876,343 A | 3/1999 | Teo | |
| 5,879,295 A | 3/1999 | Li et al. | |
| 5,881,727 A | 3/1999 | Edwards | |
| 5,885,278 A | 3/1999 | Fleischman | |
| 5,891,136 A | 4/1999 | McGee et al. | |
| 5,893,847 A | 4/1999 | Kordis | |
| 5,904,711 A | 5/1999 | Flom et al. | |
| 5,916,163 A | 6/1999 | Panescu et al. | |
| 5,919,207 A | 7/1999 | Taheri | |
| 5,921,924 A | 7/1999 | Avitall | |
| 5,935,075 A | 8/1999 | Casscells et al. | |
| 5,935,079 A | 8/1999 | Swanson et al. | |
| 5,941,251 A | 8/1999 | Panescu et al. | |
| 5,944,715 A | 8/1999 | Goble et al. | |
| 5,961,440 A | 10/1999 | Schweich, Jr. et al. | |
| 5,968,040 A | 10/1999 | Swanson et al. | |
| 5,984,950 A | 11/1999 | Cragg et al. | |
| 6,001,069 A | 12/1999 | Tachibana et al. | |
| 6,001,093 A | 12/1999 | Swanson et al. | |
| 6,014,581 A | 1/2000 | Whayne et al. | |
| 6,023,638 A | 2/2000 | Swanson | |
| 6,030,382 A | 2/2000 | Fleischman et al. | |
| 6,036,689 A | 3/2000 | Tu et al. | |
| 6,063,082 A | 5/2000 | DeVore et al. | |
| 6,071,282 A | 6/2000 | Fleischman | |
| 6,104,944 A | 8/2000 | Martinelli | |
| 6,106,460 A | 8/2000 | Panescu | |
| 6,106,522 A | 8/2000 | Fleischman et al. | |
| 6,119,030 A | 9/2000 | Morency | |
| 6,123,702 A | 9/2000 | Swanson et al. | |
| 6,138,043 A | 10/2000 | Avitall | |
| 6,142,993 A | 11/2000 | Whayne et al. | |
| 6,156,046 A | 12/2000 | Passafaro et al. | |
| 6,210,432 B1 | 4/2001 | Solem et al. | |
| 6,216,043 B1 | 4/2001 | Swanson et al. | |
| 6,217,573 B1 | 4/2001 | Webster | |
| 6,240,307 B1 | 5/2001 | Beatty | |
| 6,241,747 B1 | 6/2001 | Ruff | |
| 6,248,124 B1 | 6/2001 | Pedros et al. | |
| 6,254,598 B1 | 7/2001 | Edwards | |
| 6,258,258 B1 | 7/2001 | Sartori et al. | |
| 6,266,550 B1 | 7/2001 | Selmon et al. | |
| 6,292,695 B1 | 9/2001 | Webster, Jr. et al. | |
| 6,304,769 B1 | 10/2001 | Arenson et al. | |
| 6,306,135 B1 | 10/2001 | Ellman et al. | |
| 6,308,091 B1 | 10/2001 | Avitall | |
| 6,319,249 B1 | 11/2001 | Tollner | |
| 6,322,559 B1 | 11/2001 | Daulton et al. | |
| 6,325,797 B1 | 12/2001 | Stewart et al. | |
| 6,330,478 B1 | 12/2001 | Lee et al. | |
| 6,346,105 B1 | 2/2002 | Tu et al. | |
| 6,350,263 B1 | 2/2002 | Wetzig et al. | |
| 6,358,258 B1 | 3/2002 | Arcia et al. | |
| 6,383,151 B1 | 5/2002 | Diederich et al. | |
| 6,389,311 B1 | 5/2002 | Whayne et al. | |
| 6,391,024 B1 | 5/2002 | Sun et al. | |
| 6,391,048 B1 | 5/2002 | Ginn et al. | |
| 6,391,054 B2 | 5/2002 | Carpentier et al. | |
| 6,402,781 B1 | 6/2002 | Langberg et al. | |
| 6,428,537 B1 * | 8/2002 | Swanson | A61B 18/1492 606/41 |
| 6,436,052 B1 | 8/2002 | Nikolic et al. | |
| 6,471,693 B1 | 10/2002 | Carroll | |
| 6,471,700 B1 | 10/2002 | Burbank et al. | |
| 6,475,223 B1 | 11/2002 | Werp et al. | |
| 6,485,409 B1 | 11/2002 | Voloshin et al. | |
| 6,485,482 B1 | 11/2002 | Belef | |
| 6,485,489 B2 | 11/2002 | Teirstein et al. | |
| 6,506,210 B1 | 1/2003 | Kanner | |
| 6,514,249 B1 | 2/2003 | Maguire et al. | |
| 6,517,534 B1 | 2/2003 | McGovern | |
| 6,529,756 B1 | 3/2003 | Phan et al. | |
| 6,537,198 B1 | 3/2003 | Vidlund et al. | |
| 6,537,314 B2 | 3/2003 | Langberg et al. | |
| 6,540,670 B1 | 4/2003 | Hirata et al. | |
| 6,551,310 B1 | 4/2003 | Ganz et al. | |
| 6,551,312 B2 | 4/2003 | Zhang et al. | |
| 6,558,378 B2 | 5/2003 | Sherman et al. | |
| 6,569,160 B1 | 5/2003 | Goldin et al. | |
| 6,569,198 B1 | 5/2003 | Wilson et al. | |
| 6,575,971 B2 | 6/2003 | Hauck et al. | |
| 6,589,208 B2 | 7/2003 | Ewers et al. | |
| 6,616,684 B1 | 9/2003 | Vidlund et al. | |
| 6,626,930 B1 | 9/2003 | Allen et al. | |
| 6,632,238 B2 | 10/2003 | Ginn et al. | |
| 6,635,056 B2 | 10/2003 | Kadhiresan et al. | |
| 6,640,119 B1 | 10/2003 | Budd et al. | |
| 6,662,034 B2 | 12/2003 | Segner et al. | |
| D484,979 S | 1/2004 | Fontaine | |
| 6,704,590 B2 | 3/2004 | Haldeman | |
| 6,723,038 B1 | 4/2004 | Schroeder et al. | |
| 6,726,716 B2 | 4/2004 | Marquez | |
| 6,738,655 B1 | 5/2004 | Sen et al. | |
| 6,760,616 B2 | 7/2004 | Hoey et al. | |
| 6,763,836 B2 | 7/2004 | Tasto et al. | |
| 6,773,433 B2 | 8/2004 | Stewart et al. | |
| 6,780,197 B2 | 8/2004 | Roe et al. | |
| 6,788,969 B2 | 9/2004 | Dupree et al. | |
| 6,797,001 B2 | 9/2004 | Mathis et al. | |
| 6,800,090 B2 | 10/2004 | Alferness et al. | |
| 6,824,562 B2 | 11/2004 | Mathis et al. | |
| 6,837,886 B2 | 1/2005 | Collins et al. | |
| 6,852,076 B2 | 2/2005 | Nikolic et al. | |
| 6,855,143 B2 | 2/2005 | Davison et al. | |
| 6,890,353 B2 | 5/2005 | Cohn et al. | |
| 6,892,091 B1 | 5/2005 | Ben-Haim et al. | |
| 6,899,674 B2 | 5/2005 | Viebach et al. | |
| 6,899,709 B2 | 5/2005 | Lehmann et al. | |
| 6,907,297 B2 | 6/2005 | Wellman et al. | |
| 6,908,478 B2 | 6/2005 | Alferness et al. | |
| 6,913,576 B2 | 7/2005 | Bowman | |
| 6,918,903 B2 | 7/2005 | Bass | |
| 6,926,669 B1 | 8/2005 | Stewart et al. | |
| 6,942,657 B2 | 9/2005 | Sinofsky et al. | |
| 6,949,122 B2 | 9/2005 | Adams et al. | |
| 6,960,206 B2 | 11/2005 | Keane | |
| 6,960,229 B2 | 11/2005 | Mathis et al. | |
| 6,986,775 B2 | 1/2006 | Morales et al. | |
| 6,989,010 B2 | 1/2006 | Francischelli et al. | |
| 6,989,028 B2 | 1/2006 | Lashinski et al. | |
| 6,994,093 B2 | 2/2006 | Murphy et al. | |
| 6,997,951 B2 | 2/2006 | Solem et al. | |
| 7,001,383 B2 | 2/2006 | Keidar | |
| 7,025,776 B1 | 4/2006 | Houser et al. | |
| 7,048,734 B1 | 5/2006 | Fleischman et al. | |
| 7,050,848 B2 | 5/2006 | Hoey et al. | |
| 7,052,487 B2 | 5/2006 | Cohn et al. | |
| 7,068,867 B2 | 6/2006 | Adoram et al. | |
| 7,141,019 B2 | 11/2006 | Pearlman | |
| 7,144,363 B2 | 12/2006 | Pai et al. | |
| 7,166,127 B2 | 1/2007 | Spence et al. | |
| 7,174,201 B2 | 2/2007 | Govari et al. | |
| 7,177,677 B2 | 2/2007 | Kaula et al. | |
| 7,186,210 B2 | 3/2007 | Feld et al. | |
| 7,187,964 B2 | 3/2007 | Khoury | |
| 7,189,202 B2 | 3/2007 | Lau et al. | |
| 7,198,635 B2 | 4/2007 | Danek et al. | |
| 7,255,695 B2 | 8/2007 | Falwell et al. | |
| 7,276,044 B2 | 10/2007 | Ferry et al. | |
| 7,279,007 B2 | 10/2007 | Nikolic et al. | |
| 7,300,435 B2 | 11/2007 | Wham et al. | |

(56) References Cited

U.S. PATENT DOCUMENTS

| | | |
|---|---|---|
| 7,303,526 B2 | 12/2007 | Sharkey et al. |
| 7,311,705 B2 | 12/2007 | Sra |
| 7,317,950 B2 | 1/2008 | Lee |
| 7,335,196 B2 | 2/2008 | Swanson et al. |
| 7,468,062 B2 | 12/2008 | Oral et al. |
| 7,481,808 B2 | 1/2009 | Koyfman et al. |
| 7,496,394 B2 | 2/2009 | Ahmed et al. |
| 7,507,252 B2 | 3/2009 | Lashinski et al. |
| 7,530,980 B2 | 5/2009 | Hooven |
| 7,660,452 B2 | 2/2010 | Zwirn et al. |
| 7,736,388 B2 | 6/2010 | Goldfarb et al. |
| 7,738,967 B2 | 6/2010 | Salo |
| 7,740,584 B2 | 6/2010 | Donaldson |
| 7,826,881 B1 | 11/2010 | Beatty et al. |
| 7,877,128 B2 | 1/2011 | Schwartz |
| 8,012,149 B2 | 9/2011 | Jackson |
| 8,097,926 B2 | 1/2012 | De Graff et al. |
| 8,103,338 B2 | 1/2012 | Harlev et al. |
| D654,588 S | 2/2012 | Taube et al. |
| 8,118,853 B2 | 2/2012 | Grewe |
| 8,147,486 B2 | 4/2012 | Honour et al. |
| 8,150,499 B2 | 4/2012 | Gelbart et al. |
| D660,967 S | 5/2012 | Braido et al. |
| 8,216,228 B2 | 7/2012 | Pachon Mateos et al. |
| 8,224,432 B2 | 7/2012 | Macadam et al. |
| 8,386,057 B2 | 2/2013 | Flach et al. |
| 8,398,623 B2 | 3/2013 | Warnking et al. |
| 8,398,631 B2 | 3/2013 | Ganz |
| 8,486,063 B2 | 7/2013 | Werneth et al. |
| 8,500,731 B2 | 8/2013 | Byrd et al. |
| 8,538,501 B2 | 9/2013 | Venkatachalam et al. |
| 8,562,559 B2 | 10/2013 | Bishop |
| 8,617,156 B2 | 12/2013 | Werneth et al. |
| 8,617,228 B2 | 12/2013 | Wittenberger et al. |
| 8,712,550 B2 | 4/2014 | Grunewald |
| 8,771,267 B2 | 7/2014 | Kunis et al. |
| 8,864,745 B2 | 10/2014 | Ciavarella |
| D717,954 S | 11/2014 | Hjelle et al. |
| 8,939,970 B2 | 1/2015 | Stone et al. |
| 9,037,259 B2 | 5/2015 | Mathur |
| 9,044,254 B2 | 6/2015 | Ladtkow et al. |
| 9,101,365 B2 | 8/2015 | Highsmith |
| 9,108,052 B2 | 8/2015 | Jarrard |
| 9,198,713 B2 | 12/2015 | Wallace et al. |
| 9,289,606 B2 | 3/2016 | Paul et al. |
| 9,345,540 B2 | 5/2016 | Mallin et al. |
| 9,474,486 B2 | 10/2016 | Eliason et al. |
| 9,522,035 B2 | 12/2016 | Highsmith |
| 9,526,568 B2 | 12/2016 | Ohri et al. |
| 9,713,730 B2 | 7/2017 | Mathur et al. |
| 9,730,600 B2 | 8/2017 | Thakur et al. |
| 9,737,227 B2 | 8/2017 | Thakur et al. |
| 9,855,421 B2 | 1/2018 | Garai et al. |
| 9,883,908 B2 | 2/2018 | Madjarov et al. |
| 9,907,603 B2 | 3/2018 | Sklar et al. |
| 9,907,609 B2 | 3/2018 | Cao et al. |
| 9,924,994 B2 | 3/2018 | Sklar et al. |
| 9,924,995 B2 | 3/2018 | Sklar et al. |
| 9,968,783 B2 | 5/2018 | Bullinga et al. |
| 2001/0003158 A1 | 6/2001 | Kensey et al. |
| 2001/0005787 A1 | 6/2001 | Oz et al. |
| 2001/0018611 A1 | 8/2001 | Solem et al. |
| 2001/0020126 A1 | 9/2001 | Swanson et al. |
| 2001/0021867 A1 | 9/2001 | Kordis et al. |
| 2002/0002329 A1 | 1/2002 | Avitall |
| 2002/0016628 A1 | 2/2002 | Langberg et al. |
| 2002/0087156 A1 | 7/2002 | Maguire et al. |
| 2002/0087157 A1 | 7/2002 | Sliwa, Jr. et al. |
| 2002/0087173 A1 | 7/2002 | Alferness et al. |
| 2002/0099415 A1 | 7/2002 | Panescu et al. |
| 2002/0107478 A1 | 8/2002 | Wendlandt |
| 2002/0107511 A1 | 8/2002 | Collins et al. |
| 2002/0107530 A1 | 8/2002 | Saucer et al. |
| 2002/0115941 A1 | 8/2002 | Whayne et al. |
| 2002/0115944 A1 | 8/2002 | Mendes et al. |
| 2002/0169504 A1 | 11/2002 | Alferness et al. |
| 2002/0173784 A1 | 11/2002 | Sliwa, Jr. et al. |
| 2002/0177782 A1 | 11/2002 | Penner |
| 2002/0183836 A1 | 12/2002 | Liddicoat et al. |
| 2002/0183841 A1 | 12/2002 | Cohn et al. |
| 2002/0188170 A1 | 12/2002 | Santamore et al. |
| 2003/0028118 A1 | 2/2003 | Dupree et al. |
| 2003/0028183 A1 | 2/2003 | Sanchez et al. |
| 2003/0050685 A1 | 3/2003 | Nikolic et al. |
| 2003/0055420 A1 | 3/2003 | Kadhiresan et al. |
| 2003/0069570 A1 | 4/2003 | Witzel et al. |
| 2003/0069636 A1 | 4/2003 | Solem et al. |
| 2003/0078465 A1 | 4/2003 | Pai et al. |
| 2003/0078671 A1 | 4/2003 | Lesniak et al. |
| 2003/0105384 A1 | 6/2003 | Sharkey et al. |
| 2003/0105520 A1 | 6/2003 | Alferness et al. |
| 2003/0109770 A1 | 6/2003 | Sharkey et al. |
| 2003/0176810 A1 | 9/2003 | Maahs et al. |
| 2003/0181819 A1 | 9/2003 | Desai |
| 2003/0229395 A1 | 12/2003 | Cox |
| 2004/0002626 A1 | 1/2004 | Feld et al. |
| 2004/0054279 A1 | 3/2004 | Hanley |
| 2004/0082915 A1 | 4/2004 | Kadan |
| 2004/0133220 A1 | 7/2004 | Lashinski et al. |
| 2004/0133273 A1 | 7/2004 | Cox |
| 2004/0138744 A1 | 7/2004 | Lashinski et al. |
| 2004/0153146 A1 | 8/2004 | Lashinski et al. |
| 2004/0158321 A1 | 8/2004 | Reuter et al. |
| 2004/0176797 A1 | 9/2004 | Opolski |
| 2004/0181139 A1 | 9/2004 | Falwell et al. |
| 2004/0186566 A1 | 9/2004 | Hindrichs et al. |
| 2004/0193103 A1 | 9/2004 | Kumar |
| 2004/0215232 A1 | 10/2004 | Belhe et al. |
| 2004/0243170 A1 | 12/2004 | Suresh et al. |
| 2004/0249408 A1 | 12/2004 | Murphy et al. |
| 2004/0249453 A1 | 12/2004 | Cartledge et al. |
| 2004/0267358 A1 | 12/2004 | Reitan |
| 2005/0004668 A1 | 1/2005 | Aklog et al. |
| 2005/0015109 A1 | 1/2005 | Lichtenstein |
| 2005/0054938 A1 | 3/2005 | Wehman et al. |
| 2005/0055089 A1 | 3/2005 | Macoviak et al. |
| 2005/0060030 A1 | 3/2005 | Lashinski et al. |
| 2005/0064665 A1 | 3/2005 | Han |
| 2005/0065420 A1 | 3/2005 | Collins et al. |
| 2005/0065504 A1 | 3/2005 | Melsky et al. |
| 2005/0080402 A1 | 4/2005 | Santamore et al. |
| 2005/0096047 A1 | 5/2005 | Haberman et al. |
| 2005/0096647 A1 | 5/2005 | Steinke et al. |
| 2005/0107723 A1 | 5/2005 | Wehman et al. |
| 2005/0107871 A1 | 5/2005 | Realyvasquez et al. |
| 2005/0125030 A1 | 6/2005 | Forsberg et al. |
| 2005/0148892 A1 | 7/2005 | Desai |
| 2005/0149014 A1 | 7/2005 | Hauck et al. |
| 2005/0149159 A1 | 7/2005 | Andreas et al. |
| 2005/0154252 A1 | 7/2005 | Sharkey et al. |
| 2005/0182365 A1 | 8/2005 | Hennemann et al. |
| 2005/0187491 A1 | 8/2005 | Burbank |
| 2005/0187620 A1 | 8/2005 | Pai et al. |
| 2005/0197593 A1 | 9/2005 | Burbank et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0203558 A1 | 9/2005 | Maschke |
| 2005/0209636 A1 | 9/2005 | Widomski et al. |
| 2005/0216054 A1 | 9/2005 | Widomski et al. |
| 2005/0240249 A1 | 10/2005 | Tu et al. |
| 2005/0245892 A1 | 11/2005 | Elkins |
| 2005/0251116 A1 | 11/2005 | Steinke et al. |
| 2005/0251132 A1 | 11/2005 | Oral et al. |
| 2005/0256521 A1 | 11/2005 | Kozel |
| 2005/0261580 A1 | 11/2005 | Willis et al. |
| 2005/0267458 A1 | 12/2005 | Paul et al. |
| 2005/0267463 A1 | 12/2005 | Vanney |
| 2005/0267574 A1 | 12/2005 | Cohn et al. |
| 2006/0009755 A1 | 1/2006 | Sra |
| 2006/0009756 A1 | 1/2006 | Francischelli et al. |
| 2006/0014998 A1 | 1/2006 | Sharkey et al. |
| 2006/0015002 A1 | 1/2006 | Moaddeb et al. |
| 2006/0015003 A1 | 1/2006 | Moaddes et al. |

(56) References Cited

U.S. PATENT DOCUMENTS

| | | |
|---|---|---|
| 2006/0015038 A1 | 1/2006 | Weymarn-Scharli |
| 2006/0015096 A1 | 1/2006 | Hauck et al. |
| 2006/0025800 A1 | 2/2006 | Suresh |
| 2006/0030881 A1 | 2/2006 | Sharkey et al. |
| 2006/0085049 A1 | 4/2006 | Cory et al. |
| 2006/0089637 A1 | 4/2006 | Werneth et al. |
| 2006/0100618 A1 | 5/2006 | Chan et al. |
| 2006/0106298 A1 | 5/2006 | Ahmed et al. |
| 2006/0135968 A1 | 6/2006 | Schaller |
| 2006/0135970 A1 | 6/2006 | Schaller |
| 2006/0184242 A1 | 8/2006 | Lichtenstein |
| 2006/0199995 A1 | 9/2006 | Vijay |
| 2006/0229491 A1 | 10/2006 | Sharkey et al. |
| 2006/0235286 A1 | 10/2006 | Stone et al. |
| 2006/0235314 A1 | 10/2006 | Migliuolo et al. |
| 2006/0264980 A1 | 11/2006 | Khairkhahan et al. |
| 2006/0281965 A1 | 12/2006 | Khairkhahan et al. |
| 2006/0293698 A1 | 12/2006 | Douk |
| 2006/0293725 A1 | 12/2006 | Rubinsky et al. |
| 2007/0016068 A1 | 1/2007 | Grunwald et al. |
| 2007/0027533 A1 | 2/2007 | Douk |
| 2007/0038208 A1 | 2/2007 | Kefer |
| 2007/0083168 A1 | 4/2007 | Whiting |
| 2007/0083193 A1 | 4/2007 | Werneth et al. |
| 2007/0083195 A1 | 4/2007 | Werneth et al. |
| 2007/0088362 A1 | 4/2007 | Bonutti et al. |
| 2007/0115390 A1 | 5/2007 | Makara et al. |
| 2007/0118215 A1 | 5/2007 | Moaddeb |
| 2007/0129717 A1 | 6/2007 | Brown, III et al. |
| 2007/0161846 A1 | 7/2007 | Nikolic et al. |
| 2007/0198058 A1 | 8/2007 | Gelbart et al. |
| 2007/0213578 A1 | 9/2007 | Khairkhahan et al. |
| 2007/0213815 A1 | 9/2007 | Khairkhahan et al. |
| 2007/0232858 A1 | 10/2007 | Macnamara et al. |
| 2007/0249999 A1 | 10/2007 | Sklar et al. |
| 2007/0270688 A1 | 11/2007 | Gelbart et al. |
| 2007/0299343 A1 | 12/2007 | Waters |
| 2008/0004534 A1 | 1/2008 | Gelbart et al. |
| 2008/0004643 A1 | 1/2008 | To et al. |
| 2008/0004697 A1 | 1/2008 | Lichtenstein et al. |
| 2008/0045778 A1 | 2/2008 | Lichtenstein et al. |
| 2008/0071298 A1 | 3/2008 | Khairkhahan et al. |
| 2008/0161799 A1 | 7/2008 | Stangenes et al. |
| 2008/0262337 A1* | 10/2008 | Falwell ............. A61B 18/1492 606/41 |
| 2008/0281322 A1 | 11/2008 | Sherman et al. |
| 2008/0312713 A1 | 12/2008 | Wilfley et al. |
| 2009/0018617 A1 | 1/2009 | Skelton et al. |
| 2009/0024138 A1 | 1/2009 | Saleh |
| 2009/0069704 A1 | 3/2009 | MacAdam et al. |
| 2009/0131930 A1 | 5/2009 | Gelbart et al. |
| 2009/0157058 A1 | 6/2009 | Ferren et al. |
| 2009/0171274 A1* | 7/2009 | Harlev ................ A61B 5/6859 604/95.04 |
| 2009/0182405 A1 | 7/2009 | Arnault De La Menardiere |
| 2009/0192441 A1 | 7/2009 | Gelbart et al. |
| 2009/0270737 A1 | 10/2009 | Thornton |
| 2009/0287271 A1 | 11/2009 | Blum et al. |
| 2009/0287304 A1 | 11/2009 | Dahlgren et al. |
| 2010/0121147 A1 | 5/2010 | Oskin et al. |
| 2010/0204560 A1* | 8/2010 | Salahieh ................ A61B 5/01 606/41 |
| 2010/0211052 A1 | 8/2010 | Brown et al. |
| 2010/0249771 A1 | 9/2010 | Pearson et al. |
| 2010/0268059 A1 | 10/2010 | Ryu et al. |
| 2011/0125172 A1 | 5/2011 | Gelbart et al. |
| 2011/0172658 A1 | 7/2011 | Gelbart et al. |
| 2011/0213231 A1 | 9/2011 | Hall et al. |
| 2011/0282491 A1 | 11/2011 | Prisco et al. |
| 2012/0071870 A1 | 3/2012 | Salahieh |
| 2012/0158016 A1 | 6/2012 | Gelbart et al. |
| 2012/0165829 A1 | 6/2012 | Chen et al. |
| 2012/0271135 A1 | 10/2012 | Burke et al. |
| 2013/0165916 A1 | 6/2013 | Mathur et al. |
| 2013/0172883 A1 | 7/2013 | Lopes et al. |
| 2013/0178850 A1 | 7/2013 | Lopes et al. |
| 2013/0178851 A1 | 7/2013 | Lopes et al. |
| 2013/0184705 A1 | 7/2013 | Gelbart et al. |
| 2013/0184706 A1 | 7/2013 | Gelbart et al. |
| 2013/0190587 A1 | 7/2013 | Lopes et al. |
| 2013/0190741 A1 | 7/2013 | Moll et al. |
| 2013/0197513 A1 | 8/2013 | Lopes et al. |
| 2013/0241929 A1 | 9/2013 | Massarwa et al. |
| 2013/0304065 A1 | 11/2013 | Lopes et al. |
| 2013/0310828 A1 | 11/2013 | Reinders et al. |
| 2014/0114307 A1 | 4/2014 | Moisa et al. |
| 2014/0350552 A1 | 11/2014 | Highsmith |
| 2015/0032103 A1 | 1/2015 | Mclawhorn et al. |
| 2015/0045660 A1 | 2/2015 | Gelbart et al. |
| 2015/0066010 A1 | 3/2015 | Mclawhorn et al. |
| 2015/0126993 A1 | 5/2015 | Gelbart et al. |
| 2015/0157400 A1 | 6/2015 | Gelbart et al. |
| 2015/0245798 A1 | 9/2015 | Gelbart et al. |
| 2015/0250539 A1 | 9/2015 | Gelbart et al. |
| 2015/0351836 A1 | 12/2015 | Prutchi |
| 2015/0351837 A1 | 12/2015 | Gelbart et al. |
| 2016/0008059 A1 | 1/2016 | Prutchi |
| 2016/0008062 A1 | 1/2016 | Gelbart et al. |
| 2016/0100884 A1 | 4/2016 | Fay et al. |
| 2016/0143686 A1 | 5/2016 | Tunay et al. |
| 2016/0175009 A1 | 6/2016 | Davies et al. |
| 2016/0242667 A1 | 8/2016 | Fay et al. |
| 2016/0262647 A1 | 9/2016 | Berenfeld |
| 2016/0302858 A1 | 10/2016 | Bencini |
| 2016/0317223 A1 | 11/2016 | Avitall |
| 2016/0331259 A1 | 11/2016 | Harlev et al. |
| 2016/0361111 A1 | 12/2016 | Seidel |
| 2016/0367315 A1 | 12/2016 | Moisa et al. |
| 2017/0027465 A1 | 2/2017 | Blauer et al. |
| 2017/0035486 A1 | 2/2017 | Lopes et al. |
| 2017/0065198 A1 | 3/2017 | Ruppersberg |
| 2017/0065339 A1 | 3/2017 | Mickelsen |
| 2017/0065812 A1 | 3/2017 | Goedeke et al. |
| 2017/0071661 A1 | 3/2017 | Hoitink et al. |
| 2017/0100189 A1 | 4/2017 | Clark et al. |
| 2017/0156791 A1 | 6/2017 | Govari |
| 2017/0164858 A1 | 6/2017 | Basu |
| 2017/0215947 A1 | 8/2017 | Rioux et al. |
| 2017/0281193 A1 | 10/2017 | Asirvatham et al. |
| 2017/0296084 A1 | 10/2017 | Blauer et al. |
| 2017/0312028 A1 | 11/2017 | Harlev et al. |
| 2017/0333124 A1 | 11/2017 | Gelbart et al. |
| 2018/0008343 A1 | 1/2018 | Gelbart et al. |
| 2018/0020916 A1 | 1/2018 | Ruppersberg |
| 2018/0036074 A1 | 2/2018 | Gelbart et al. |
| 2018/0036075 A1 | 2/2018 | Gelbart et al. |
| 2018/0036076 A1 | 2/2018 | Gelbart et al. |
| 2018/0036077 A1 | 2/2018 | Gelbart et al. |
| 2018/0042667 A1 | 2/2018 | Pappone et al. |
| 2018/0042671 A1 | 2/2018 | Gelbart et al. |
| 2018/0055565 A1 | 3/2018 | Gelbart et al. |
| 2018/0056074 A1 | 3/2018 | Clark et al. |
| 2018/0071017 A1 | 3/2018 | Bar-Tal et al. |
| 2018/0092688 A1 | 4/2018 | Tegg |
| 2018/0116595 A1 | 5/2018 | Ruppersberg |
| 2018/0117304 A1 | 5/2018 | Koop et al. |
| 2018/0153437 A1 | 6/2018 | Schwartz et al. |
| 2018/0235692 A1 | 8/2018 | Efimov et al. |
| 2018/0236221 A1 | 8/2018 | Opie et al. |
| 2018/0280070 A1 | 10/2018 | Pasquino et al. |
| 2019/0046265 A1 | 2/2019 | Moisa et al. |
| 2019/0223950 A1 | 7/2019 | Gelbart et al. |
| 2019/0239948 A1 | 8/2019 | Gelbart et al. |
| 2020/0375659 A1 | 12/2020 | Gelbart |
| 2021/0000537 A1 | 1/2021 | Gelbart |
| 2021/0059750 A1 | 3/2021 | Gelbart |

FOREIGN PATENT DOCUMENTS

| | | |
|---|---|---|
| DE | 102011085720 A1 | 5/2013 |
| EP | 0723467 A1 | 7/1996 |
| EP | 1169974 A1 | 1/2002 |
| EP | 1233718 B1 | 8/2006 |
| EP | 1923095 A2 | 5/2008 |

(56) References Cited

FOREIGN PATENT DOCUMENTS

| | | |
|---|---|---|
| EP | 1814450 B1 | 1/2013 |
| EP | 2101642 B1 | 7/2014 |
| EP | 2231060 B1 | 5/2015 |
| EP | 2395933 B1 | 5/2016 |
| EP | 2566565 B1 | 10/2017 |
| EP | 3318211 A2 | 5/2018 |
| EP | 3102136 B1 | 6/2018 |
| EP | 2765939 B1 | 9/2018 |
| EP | 2793725 B1 | 9/2018 |
| EP | 3375365 A2 | 9/2018 |
| WO | 9510320 A1 | 4/1995 |
| WO | 95/20349 A1 | 8/1995 |
| WO | 97/17892 A1 | 5/1997 |
| WO | 0108575 A2 | 2/2001 |
| WO | 02/087437 A1 | 11/2002 |
| WO | 03015611 A2 | 2/2003 |
| WO | 03077800 A1 | 9/2003 |
| WO | 2004012629 A1 | 2/2004 |
| WO | 2004047679 A1 | 6/2004 |
| WO | 2004084746 A2 | 10/2004 |
| WO | 2004100803 A1 | 11/2004 |
| WO | 2005070330 A1 | 8/2005 |
| WO | 2005102181 A1 | 11/2005 |
| WO | 2006017809 A2 | 2/2006 |
| WO | 2006105121 A2 | 10/2006 |
| WO | 2006135747 A2 | 12/2006 |
| WO | 2006135749 A2 | 12/2006 |
| WO | 2007021647 A2 | 2/2007 |
| WO | 2007115390 A1 | 10/2007 |
| WO | 2008002606 A2 | 1/2008 |
| WO | 2009011721 A1 | 1/2009 |
| WO | 2009065042 A2 | 5/2009 |
| WO | 2012050877 A1 | 4/2012 |
| WO | 2012/100184 A2 | 7/2012 |
| WO | 2012/100185 A2 | 7/2012 |
| WO | 2013064576 A1 | 5/2013 |
| WO | 2013/173917 A1 | 11/2013 |
| WO | 2016181316 A1 | 11/2016 |
| WO | 2017041889 A2 | 3/2017 |
| WO | 2017041891 A1 | 3/2017 |
| WO | 2017042623 A1 | 3/2017 |
| WO | 2017056056 A1 | 4/2017 |
| WO | 2017070252 A1 | 4/2017 |
| WO | 2017136262 A1 | 8/2017 |
| WO | 2018067540 A1 | 4/2018 |
| WO | 2018075396 A1 | 4/2018 |
| WO | 2018081225 A1 | 5/2018 |
| WO | 2018144765 A1 | 8/2018 |
| WO | 2018146613 A2 | 8/2018 |

OTHER PUBLICATIONS

Gabriel et al., "The Dielectric Properties of Biological Tissues: I. Literature Survey," Phys. Med. Biol. 41:2231-2249, 1996.
Konings et al., "Development of an Intravascular Impedance Catheter for Detection of Fatty Lesions in Arteries," IEEE Transactions on Medical Imaging, 16(4):439-446, 1997.
Mack, "New Techniques for Percutaneous Repair of the Mitral Valve," Heart Failure Review, 11:259-268, 2006.
Otasevic et al., "First-in-Man Implantation of Left Ventricular Partitioning Device in a Patient With Chronic Heart Failure: Twelve-Month Follow-up," Journal of Cardiac Failure 13(7):517-520, 2007.
Sharkey et al., "Left Ventricular Apex Occluder. Description of a Ventricular Partitioning Device," EuroIntervention 2:125-127, 2006.
Stiles, et al., "Simulated Characterization of Atherosclerotic Lesions in the Coronary Arteries by Measurement of Bioimpedance," IEE Transactions on Biomedical Engineering, 50(7):916-921,2003.
Tanaka et al., "Artificial SMA Valve for Treatment of Urinary Incontinence: Upgrading of Valve and Introduction of Transcutaneous Transformer," Bio-Medical Materials and Engineering 9:97-112, 1999.
Timek et al.., "Septal-Lateral Annular Cinching ('SLAC') Reduces Mitral Annular Size Without Perturbing Normal Annular Dynamics," Journal of Heart Valve Disease 11 (1):2-10, 2002.
Timek et al., "Septal-Lateral Annular Cinching Abolishes Acute Ischemic Mitral Regurgitation," Journal of Thoracic and Cardiovascular Surgery, 123(5):881-888, 2002.
Valvano et al., "Thermal Conductivity and Diffusivity of Biomaterials Measured with Self-Heated Thermistors," International Journal of Thermodynamics, 6(3):301-311, 1985.
Gelbart et al., "Automatic Atherectomy System," Office Action dated Mar. 4, 2009 for U.S. Appl. No. 11/436,584, 7 pages.
Gelbart et al., "Automatic Atherectomy System," Amendment filed Aug. 4, 2009 for U.S. Appl. No. 11/436,584, 35 pages.
Gelbart et al., "Automatic Atherectomy System," Office Action dated Dec. 1, 2009 for U.S. Appl. No. 11/436,584, 10 pages.
Gelbart et al., "Automatic Atherectomy System," Amendment filed Mar. 30, 2010 for U.S. Appl. No. 11/436,584, 20 pages.
Gelbart et al., "Automatic Atherectomy System," Amendment filed Oct. 25, 2010 for U.S. Appl. No. 11/436,584, 9 pages.
Gelbart et al., "Automatic Atherectomy System," Office Action dated Dec. 14, 2010 for U.S. Appl. No. 11/436,584, 12 pages.
Gelbart et al., "Intra-Cardiac Mapping and Ablation Method," Preliminary Amendment filed Aug. 29, 2007 for U.S. Appl. No. 11/475,950,42 pages.
Gelbart et al., "Intra-Cardiac Mapping and Ablation Method," Amendment filed Mar. 5, 2008 for U.S. Appl. No. 11/475,950, 11 pages.
Gelbart et al., "Intra-Cardiac Mapping and Ablation Method," Office Action dated Jun. 23, 2010 for U.S. Appl. No. 11/475,950, 18 pages.
Gelbart et al., "Intra-Cardiac Mapping and Ablation Method," Amendment filed Aug. 16, 2010 for U.S. Appl. No. 11/475,950, 22 pages.
Gelbart et al., "Intra-Cardiac Mapping and Ablation Method," Office Action dated Nov. 23, 2010 for U.S. Appl. No. 11/475,950, 25 pages.
Gelbart et al., "Intra-Cardiac Mapping and Ablation Method," Amendment filed Feb. 23, 2011 for U.S. Appl. No. 11/475,950, 28 pages.
Gelbart et al., "Automatic Atherectomy System," Office Action dated Jun. 15, 2011, for U.S. Appl. No. 12/950,871, 16 pages.
Gelbart et al., "Liposuction System," Office Action dated Mar. 16, 2011 for U.S. Appl. No. 12/010,458, 12 pages.
Gelbart et al., "Liposuction System," Amendment filed Jun. 10, 2011 for U.S. Appl. No. 12/010,458, 10 pages.
Lichtenstein "Method and Apparatus for Percutaneous Reduction of Anterior-Posterior Diameter of Mitral Valve," U.S. Appl. No. 10/690,131, filed Oct. 20, 2003, 31 pages.
International Search Report, dated Dec. 5, 2007, for PCT/US2007/014902, 5 pages.
International Preliminary Report on Patentability, dated Jan. 6, 2009, for PCT/US2007/014902, 8 pages.
International Search Report, dated Dec. 2, 2009, for PCT/US2008/083644, 5 pages.
Written Opinion, dated Dec. 5, 2007, for PCT/US2007/014902, 7 pages.
Written Opinion, dated Dec. 2, 2009, for PCT/US2008/083644, 9 pages.
Gelbart et al., "Automatic Atherectomy System," Amendment filed Sep. 15, 2011 for U.S. Appl. No. 12/950,871, 21 pages.
Gelbart et al., "Liposuction System, " Amendment filed Dec. 7, 2011 for U.S. Appl. No. 12/010,458, 15 pages.
Gelbart et al., "Liposuction System," Office Action dated Sep. 14, 2011 for U.S. Appl. No. 12/010,458, 9 pages.
Notice of Allowance issued in U.S. Appl. No. 13/782,889, dated Aug. 25, 2016.
Communication pursuant to Article 94(3) EPC issued in European Appln. No. 19189222.3 dated Nov. 17, 2022.
Non-Final Office Action issued in copending U.S. Appl. No. 17/072,262 dated Dec. 1, 2022.
Final Office Action issued in copending U.S. Appl. No. 16/521,745 dated Dec. 9, 2022.
Response After Final Action filed in copending U.S. Appl. No. 16/521,745 dated Jan. 13, 2023.
Preliminary Amendment filed in copending U.S. Appl. No. 15/697,744 dated Sep. 21, 2017.

(56) References Cited

OTHER PUBLICATIONS

Amendment filed in U.S. Appl. No. 14/564,463 dated Oct. 17, 2017.
Notice of Allowance issued in U.S. Appl. No. 14/713,114 dated Nov. 1, 2017.
Notice of Allowance issued in U.S. Appl. No. 14/564,463 dated Nov. 9, 2017.
Preliminary Amendment filed in copending U.S. Appl. No. 15/784,555 dated Nov. 7, 2017.
Preliminary Amendment filed in copending U.S. Appl. No. 15/784,775 dated Nov. 7, 2017.
Preliminary Amendment filed in copending U.S. Appl. No. 15/784,722 dated Nov. 7, 2017.
Preliminary Amendment filed in copending U.S. Appl. No. 15/725,731 dated Oct. 24, 2017.
Preliminary Amendment filed in copending U.S. Appl. No. 15/784,647 dated Nov. 7, 2017.
Preliminary Amendment filed in copending U.S. Appl. No. 15/725,662 dated Oct. 24, 2017.
Office Action issued in U.S. Appl. No. 14/804,924 dated Nov. 17, 2017.
Response to Office Action filed in U.S. Appl. No. 13/785,910 dated Nov. 30, 2017.
Amendment filed in U.S. Appl. No. 13/785,910 dated Feb. 27, 2018.
Examination Report issued in European Application No. 13793216.6 dated Nov. 24, 2017.
Office Action issued in Chinese Application No. 201510432392.3 dated Nov. 17, 2017. Concise Explanation of Relevance and English translation provided.
Examination Report issued in European Application No. 15188407.9 dated Dec. 11, 2017.
Office Action issued in U.S. Appl. No. 13/785,910 dated Jan. 12, 2018.
Amendment filed in U.S. Appl. No. 14/804,924 dated Feb. 27, 2018.
Office Action issued in U.S. Appl. No. 14/804,810 dated Nov. 30, 2017.
Amendment filed in U.S. Appl. No. 14/804,810 dated Feb. 27, 2018.
Notice of Allowance issued in U.S. Appl. No. 14/804,924 dated Mar. 27, 2018.
Notice of Allowance issued in U.S. Appl. No. 14/804,810 dated Mar. 30, 2018.
Office Action issued in Chinese Application No. 201510432392.3 dated May 18, 2018. Concise Explanation of Relevance provided.
Amendment filed in U.S. Appl. No. 14/713,114, filed Aug. 23, 2017.
Notice of Allowance issued in U.S. Appl. No. 14/713,190 dated Aug. 28, 2017.
Office Action issued in U.S. Appl. No. 13/785,910 dated Aug. 30, 2017.
Office Action issued in copending U.S. Appl. No. 16/658,820 mailed Oct. 22, 2021.
Copending U.S. Appl. No. 17/513,070, filed Oct. 28, 2021 (a copy is not yet available to the public and the Examiner has ready access to the cited application).
Office Action issued in copending U.S. Appl. No. 16/662,537 dated Oct. 29, 2021.
Amendment filed in copending U.S. Appl. No. 16/521,712 dated Nov. 1, 2021.
Preliminary Amendment filed in copending U.S. Appl. No. 17/513,070 dated Nov. 8, 2021.
Office Action issued in copending U.S. Appl. No. 15/299,640 dated Nov. 12, 2021.
Notice of Allowance issued in copending U.S. Appl. No. 15/287,988 dated Nov. 15, 2021.
Extended European Search Report issued in European Application No. 19215957.2 dated Mar. 26, 2020.
Bard, "Mesh Ablator Catheter", Brochure, 2008, 4 pgs, Bard Electrophysiology Division, C.R. Bard Inc., 55 Technology Drive Lowell, MA 07851 USA.

Biotronik's "AlCath Flutter Gold Cath for Atrial Flutter Available in EU", Sep. 19, 2013, medGadget, 3 pgs, http://www.medgadget.com/2013/09/biotroniks-alcath-flutter-gold-cath-for-atrial-flutter-unveiled-in-europe.html [Jun. 24, 2014 2:37:09 PM].
"Constellation Mapping Catheters", Brochure, Boston Scientific Corp., 2 pgs © 2007 Boston Scientific Corporation.
"Waveforms and Segments", Ensite System Instructions for use, 54-06154-001 Rev02, Chapter 7 pp. 85-90 © 2007 St. Jude Medical.
Extended European Search Report and EP search opinion for EP 12736677.1, dated Mar. 28, 2014, corresponding to PCT/US2012/022061.
Extended European Search Report and EP search opinion for EP 12736962.7, dated Mar. 28, 2014, corresponding to PCT/US2012/022062.
Extended European Search Report dated Aug. 20, 2013 issued in EP Patent Application No. 13172848.7.
Written Opinion dated Aug. 22, 2012 for PCT/US2012/022061, 6 pgs.
International Search Report and Written Opinion dated Aug. 2, 2013 issued in PCT/CA2013/050350.
International Search Report and Written Opinion dated Sep. 17, 2013 issued in PCT/US2013/039982.
International Search Report and Written Opinion dated Sep. 27, 2013 issued in PCT/US2013/039977.
International Search Report dated Jul. 30, 2012 for PCT/US2012/022062, 5 pgs.
Written Opinion dated Jul. 30, 2012 for PCT/US2012/022062, 5 pgs.
International Search Report dated Aug. 22, 2012 for PCT/US2012/022061, 5 pgs.
"Phased RF Catheter Ablation System", 2014 Medtronic Inc., 2 pgs, http://www.medtronic.eu/your-health/atrial-fibrillation/about-the-therapy/our-phased-rf-ablation-system/[Jun. 24, 2014 2:38:05 PM].
"ThermoCool® Irrigated Tip Catheter", Brochure, Biosense Webster, 4 pgs , Biosense Webster, Inc. 3333 Diamond Canyon Road Diamond Bar, CA 91765, USA, © Biosense Webster, Inc. 2009 All rights reserved. 1109003.0.
Gelbart "Medical Device for Use in Bodily Lumens, for Example an Atrium", OA mailed Jul. 25, 2011 for U.S. Appl. No. 11/941,819, now published as US 2009-0131930 A1.
Gelbart et al., "Apparatus and Method for Intra-Cardiac Mapping and Ablation", Notice of Allowance dated Oct. 23, 2014 for U.S. Appl. No. 11/475,950, 10 pgs.
Gelbart et al., "Medical Device for Use in Bodily Lumens, for Example an Atrium", Notice of Allowance dated Nov. 13, 2014 for U.S. Appl. No. 13/070,215, 54 pages.
International Search Report dated Mar. 10, 2015, for International Application PCT/CA2014/051144; 10 pages.
Written Opinion dated Mar. 10, 2015, for International Application PCT/CA2014/051144; 4 pages.
Official Action issued in CN201280004400.9, dated Dec. 3, 2014.
Non-final Office Action issued in U.S. Appl. No. 13/782,867, dated Apr. 15, 2015.
Non-final Office Action issued in U.S. Appl. No. 13/782,903, dated Apr. 28, 2015.
Lopes et al., "Enhanced Medical Device for Use in Bodily Cavities, for Example an Atrium", Office Action dated May 22, 2015 for U.S. Appl. No. 13/782,889, 86 pages.
Lopes et al., "High-Density Electrode-Based Medical Device System", Office Action dated Jul. 10, 2015 for U.S. Appl. No. 13/793,076, 98 pages.
Lopes et al., "High-Density Electrode-Based Medical Device System", Office Action dated Jul. 9, 2015 for U.S. Appl. No. 13/793,213, 99 pages.
Gelbart et al., "Apparatus and Method for Intra-Cardiac Mapping and Ablation", Office Action dated Aug. 5, 2015 for U.S. Appl. No. 13/785,910, 79 pages.
Lopes et al., "Enhanced Medical Device for Use in Bodily Cavities, for Example an Atrium", Amendment filed Aug. 24, 2015 for U.S. Appl. No. 13/782,889, 21 pages.
Lopes et al., "Enhanced Medical Device for Use in Bodily Cavities, for Example an Atrium", Amendment filed Aug. 28, 2015 for U.S. Appl. No. 13/782,903, 19 pages.

(56) References Cited

OTHER PUBLICATIONS

Lopes et al., "Enhanced Medical Device for Use in Bodily Cavities, for Example an Atrium", Amendment filed Sep. 14, 2015 for U.S. Appl. No. 13/782,867, 25 pages.
Lopes et al., "High-Density Electrode-Based Medical Device System ", Amendment filed Oct. 9, 2015 for U.S. Appl. No. 13/793,213, 26 pages.
Lopes et al., "High-Density Electrode-Based Medical Device System ", Amendment filed Oct. 9, 2015 for U.S. Appl. No. 13/793,076, 14 pages.
Examination Report issued in EP13172848.7, dated Sep. 21, 2015.
Extended European Search Report issued in EP13793216.6, dated Oct. 30, 2015.
Moisa et al., "Catheter System ", Office Action dated Nov. 16, 2015 for U.S. Appl. No. 14/136,946, 92 pages.
Office Action issued in U.S. Appl. No. 13/782,889, dated Dec. 18, 2015.
Office Action issued in U.S. Appl. No. 13/782,903, dated Dec. 18, 2015.
Extended European Search Report issued in EP15188407.9, dated Jan. 21, 2016.
Lopes et al. "Enhanced Medical Device for Use in Bodily Cavities, for Example an Atrium", Office Action dated Jan. 25, 2016 for U.S. Appl. No. 13/782,867, 49 pages.
Notice of Allowance issued in U.S. Appl. No. 13/793,076, dated Feb. 10, 2016.
Final Office Action issued in U.S. Appl. No. 13/793,213, dated Feb. 26, 2016.
Non-Final Office Action issued in U.S. Appl. No. 29/509,719, dated Feb. 25, 2016.
Quayle issued in U.S. Appl. No. 29/509,621, dated Feb. 26, 2016.
Quayle issued in U.S. Appl. No. 29/509,636, dated Feb. 26, 2016.
Non-Final Office Action issued in U.S. Appl. No. 13/785,910 dated Apr. 8, 2016.
Non-Final Office Action issued in U.S. Appl. No. 14/229,250 dated Apr. 28, 2016.
Notice of Allowance issued in U.S. Appl. No. 13/793,076 dated Jul. 7, 2016.
Extended European Search Report issued in European Application No. 19189222.3 dated Nov. 29, 2019.
Notice of Allowance issued in copending U.S. Appl. No. 16/369,528 dated May 12, 2022.
Notice of Allowance issued in copending U.S. Appl. No. 16/381,317 dated May 16, 2022.
Notice of Allowance issued in copending U.S. Appl. No. 16/381,344 dated May 16, 2022.
Copending U.S. Appl. No. 17/716,303, filed Apr. 8, 2022 (a copy is not yet available to the public and the Examiner has ready access to the cited application).
Amendment filed in copending U.S. Appl. No. 17/500,186 dated Apr. 28, 2022.
Notice of Allowance issued in copending U.S. Appl. No. 17/500,186 dated May 18, 2022.
Office Action issued in copending U.S. Appl. No. 15/784,722 dated Mar. 23, 2020.
Office Action issued in copending U.S. Appl. No. 15/784,775 dated Mar. 23, 2020.
Office Action issued in German Patent Appln. No. 112008003108.8 dated Oct. 28, 2019. English machine translation provided.
Copending U.S. Appl. No. 16/658,820, filed Oct. 21, 2019 (a copy is not yet available to the public and the Examiner has ready access to the cited application).
Copending U.S. Appl. No. 16/662,537, filed Oct. 24, 2019 (a copy is not yet available to the public and the Examiner has ready access to the cited application).
Preliminary Amendment filed in copending U.S. Appl. No. 16/658,820 dated Nov. 7, 2019.
Preliminary Amendment filed in copending U.S. Appl. No. 16/662,537 dated Nov. 19, 2019.
Lopes et al., "Intra-Cardiac Procedure Device", Amendment filed in U.S. Appl. No. 29/509,636, filed Jul. 22, 2016, 5 pgs.
Lopes et al., "Intra-Cardiac Procedure Device", Amendment filed in U.S. Appl. No. 29/509,636 dated Nov. 17, 2016, 3 pgs.
Notice of Allowance issued in U.S. Appl. No. 29/509,636 dated Sep. 27, 2016.
Lopes et al., "Intra-Cardiac Procedure Device", Amendment filed in U.S. Appl. No. 29/509,621 dated Jul. 22, 2016, 5 pgs.
Lopes et al., "Intra-Cardiac Procedure Device", Amendment filed in U.S. Appl. No. 29/509,621 dated Nov. 17, 2016, 3 pgs.
Notice of Allowance issued in U.S. Appl. No. 29/509,621 dated Sep. 27, 2016.
Lopes et al., "Enhanced Medical Device for Use in Bodily Cavities, for Example an Atrium", Preliminary Amendment filed in co-pending U.S. Appl. No. 15/299,640 dated Oct. 21, 2016, 4 pgs.
Lopes et al., "Enhanced Medical Device for Use in Bodily Cavities, for Example an Atrium", Preliminary Amendment filed in co-pending U.S. Appl. No. 15/299,640 dated Dec. 9, 2016, 11 pgs.
Gelbart et al., "Intra-Cardiac Mapping and Ablation Method", Amendment filed in U.S. Appl. No. 11/475,950 dated Feb. 12, 2013, 4 pgs.
Moisa et al., "Catheter System", Preliminary Amendment filed in co-pending U.S. Appl. No. 15/254,130 dated Sep. 19, 2016, 22 pgs.
Gelbart et al., "Apparatus and Method for Intra-Cardiac Mapping and Ablation", Preliminary Amendment filed in U.S. Appl. No. 14/804,924 dated Jul. 30, 2015, 5 pgs.
Gelbart et al., "Apparatus and Method for Intra-Cardiac Mapping and Ablation", Preliminary Amendment filed in U.S. Appl. No. 14/804,810 dated Jul. 30, 2015, 10 pgs.
Gelbart et al., "Medical Device for Use in Bodily Lumens, for Example an Atrium", Preliminary Amendment filed in U.S. Appl. No. 14/713,190 dated May 15, 2015, 3 pgs.
Gelbart et al., "Medical Device for Use in Bodily Lumens, for Example an Atrium", Preliminary Amendment filed in U.S. Appl. No. 14/713,190 dated Jun. 16, 2015, 7 pgs.
Gelbart et al., "Medical Device for Use in Bodily Lumens, for Example an Atrium", Preliminary Amendment filed in U.S. Appl. No. 14/713,114 dated Jun. 16, 2015, 8 pgs.
Office Action issued in U.S. Appl. No. 14/521,692 dated Jan. 10, 2017.
Gelbart et al., "Medical Device for Use in Bodily Lumens, for Example an Atrium", Amendment filed in U.S. Appl. No. 14/229,305 dated Sep. 27, 2016, 15 pgs.
Notice of Allowance issued in U.S. Appl. No. 14/229,305 dated Nov. 8, 2016.
Gelbart et al., "Medical Device for Use in Bodily Lumens, for Example an Atrium", Amendment filed in U.S. Appl. No. 14/229,250 dated Sep. 27, 2016, 13 pgs.
Notice of Allowance issued in U.S. Appl. No. 14/229,250 dated Dec. 7, 2016.
Moisa et al., "Catheter System", Amendment filed in U.S. Appl. No. 14/136,946 dated Apr. 18, 2016, 19 pgs.
Lopes et al., "Enhanced Medical Device for Use in Bodily Cavities, for Example an Atrium", Amendment filed in U.S. Appl. No. 13/942,354 dated Jan. 4, 2017, 23 pgs.
Lopes et al., "High-Density Electrode-Based Medical Device System", Preliminary Amendment filed in U.S. Appl. No. 13/793,076 dated May 26, 2016, 15 pgs.
Lopes et al., "High-Density Electrode-Based Medical Device System", Amendment filed in U.S. Appl. No. 13/793,076 dated May 9, 2016, 15 pgs.
Gelbart et al., "Apparatus and Method for Intracardiac Mapping and Ablation", Preliminary Amendment filed in U.S. Appl. No. 13/785,931 dated Mar. 5, 2013, 2 pgs.
Gelbart et al., "Apparatus and Method for Intra-Cardiac Mapping and Ablation", Amendment filed in U.S. Appl. No. 13/785,910 dated Feb. 9, 2016, 11 pgs.
Gelbart et al., "Apparatus and Method for Intra-Cardiac Mapping and Ablation", Amendment filed in U.S. Appl. No. 13/785,910 dated Jan. 5, 2016, 15 pgs.
Gelbart et al., "Apparatus and Method for Intra-Cardiac Mapping and Ablation", Amendment filed in U.S. Appl. No. 13/785,910 dated Aug. 8, 2016, 18 pgs.

(56) References Cited

OTHER PUBLICATIONS

Office Action issued in U.S. Appl. No. 13/785,910 dated Nov. 2, 2016.
Lopes et al., "Enhanced Medical Device for Use in Bodily Cavities, for Example an Atrium", Amendment filed in U.S. Appl. No. 13/782,889 dated May 17, 2016, 51 pgs.
Lopes et al., "Enhanced Medical Device for Use in Bodily Cavities, for Example an Atrium", Amendment filed in U.S. Appl. No. 13/782,867 dated May 17, 2016, 39 pgs.
Lopes et al., "High-Density Electrode-Based Medical Device System" Amendment filed in U.S. Appl. No. 13/793,213 dated May 26, 2016, 39 pgs.
Office Action issued in U.S. Appl. No. 14/564,463 dated Feb. 28, 2017.
Notice of Allowance issued in U.S. Appl. No. 13/942,354 dated Feb. 10, 2017.
Decision to Refuse a European Patent Application issued in European Patent Application No. 13172848.7 dated Feb. 22, 2017.
Gelbart et al., "Apparatus and Method for Intra-Cardiac Mapping and Ablation", Amendment filed In U.S. Appl. No. 13/785,910 dated Mar. 24, 2017, 30 pgs.
Gelbart et al., "Medical Device for Use in Bodily Lumens, for Example an Atrium", Amendment filed in U.S. Appl. No. 14/521,692 dated Mar. 31, 2017, 9 pgs.
Office Action issued in Chinese Patent Application No. 201510432392.3 dated Mar. 8, 2017. English concise Explanation of Relevance provided.
Notice of Allowance issued in U.S. Appl. No. 14/521,692 dated May 19, 2017.
Office Action issued in U.S. Appl. No. 14/713,114 dated Jun. 1, 2017.
Quayle Action issued in U.S. Appl. No. 14/713,190 dated May 30, 2017.
Office Action issued in German Application No. 112008003108.8 dated May 8, 2017. English translation provided.
Amendment filed in U.S. Appl. No. 14/564,463, filed May 25, 2017.
European Search Report issued in European Patent Application No. 14871405.8 dated Jul. 5, 2017.
Office Action issued in U.S. Appl. No. 14/564,463 dated Jul. 17, 2017.
Response to Quayle Action filed in U.S. Appl. No. 14/713,190 dated Jul. 24, 2017.
Preliminary Amendment filed in U.S. Appl. No. 14/521,692 dated Oct. 23, 2014.
Preliminary Amendment filed in copending U.S. Appl. No. 15/663,077 dated Aug. 8, 2017.
Non-Final Office Action issued in copending U.S. Appl. No. 16/369,528 dated Dec. 6, 2021.
Notice of Allowance issued in Chinese Application No. 201810941271.5 dated Dec. 22, 2021.
Non-Final Office Action issued in copending U.S. Appl. No. 16/381,317 dated Jan. 10, 2022.
Notice of Allowance issued in copending U.S. Appl. No. 16/521,712 dated Jan. 11, 2022.
Amendment filed in copending U.S. Appl. No. 16/658,820 dated Jan. 17, 2022.
Amendment filed in copending U.S. Appl. No. 16/662,537 dated Jan. 18, 2022.
Non-Final Office Action issued in copending U.S. Appl. No. 16/381,344 dated Feb. 1, 2022.
Preliminary Amendment filed in copending U.S. Appl. No. 17/584,705 dated Feb. 2, 2022.
Copending U.S. Appl. No. 17/584,705, filed Jan. 26, 2022 (a copy is not yet available to the public and the Examiner has ready access to the cited application).
Non-Final Office Action issued in copending U.S. Appl. No. 17/500,186 dated Feb. 9, 2022.
Amendment filed in copending U.S. Appl. No. 15/299,640 dated Feb. 8, 2022.
Notice of Allowance issued in copending U.S. Appl. No. 16/662,537 dated Feb. 14, 2022.
Notice of Allowance issued in copending U.S. Appl. No. 16/161,319 dated Feb. 16, 2022.
Office Action issued in copending European Application No. 19172980.5 dated Jan. 21, 2022.
Notice of Allowance issued in U.S. Appl. No. 13/785,910 dated Jun. 15, 2018.
Examination Report issued in European Appln. No. 14871405.8 dated Jul. 6, 2018.
Notice of Intention to Grant issued in EP Appln. No. 14871405.8 dated Jan. 22, 2019.
Notice of Intention to Grant issued in EP Appln. No. 15188407.9 dated Mar. 20, 2019.
Copending U.S. Appl. No. 16/381,317, filed Apr. 11, 2019 (a copy is not included because the cited application is not yet available to the public and the Examiner has ready access to the cited application).
Preliminary Amendment filed in copending U.S. Appl. No. 16/369,528 dated Apr. 24, 2019.
Preliminary Amendment filed in copending U.S. Appl. No. 16/381,317 dated Apr. 24, 2019.
Preliminary Amendment filed in copending U.S. Appl. No. 16/381,344 dated Apr. 24, 2019.
Office Action issued in copending U.S. Appl. No. 15/254,130 dated May 28, 2019.
Copending U.S. Appl. No. 16/407,379, filed May 9, 2019 (a copy is not included because the cited application is not yet available to the public and the Examiner has ready access to the cited application).
Preliminary Amendment filed in copending U.S. Appl. No. 16/407,379 dated Jun. 12, 2019.
Notice of Intention to Grant issued in EP Appln. No. 13793216.6 dated Jul. 15, 2019.
Copending U.S. Appl. No. 16/521,712, filed Jul. 25, 2019 (a copy is not included because the cited application is not yet available to the public and the Examiner has ready access to the cited application).
Copending U.S. Appl. No. 16/521,732, filed Jul. 25, 2019 (a copy is not included because the cited application is not yet available to the public and the Examiner has ready access to the cited application).
Copending U.S. Appl. No. 16/521,745, filed Jul. 25, 2019 (a copy is not included because the cited application is not yet available to the public and the Examiner has ready access to the cited application).
Preliminary Amendment filed in copending U.S. Appl. No. 16/521,712 dated Jul. 25, 2019.
Preliminary Amendment filed in copending U.S. Appl. No. 16/521,732 dated Jul. 25, 2019.
Preliminary Amendment filed in copending U.S. Appl. No. 16/521,745 dated Jul. 25, 2019.
Amendment filed in copending U.S. Appl. No. 15/254,130 dated Aug. 13, 2019.
Second Preliminary Amendment filed in copending U.S. Appl. No. 16/521,712 dated Aug. 15, 2019.
Second Preliminary Amendment filed in copending U.S. Appl. No. 16/521,732 dated Aug. 15, 2019.
Second Preliminary Amendment filed in copending U.S. Appl. No. 16/521,745 dated Aug. 15, 2019.
Notice of Allowance issued in U.S. Appl. No. 15/254,130 dated Sep. 12, 2019.
Notice of Allowance issued in U.S. Appl. No. 15/663,077 dated Sep. 24, 2019.
Extended European Search Report issued in European Appln. No. 19172980.5 dated Aug. 21, 2019.
Office Action issued in copending U.S. Appl. No. 15/697,744 dated Feb. 28, 2020.
Office Action issued in copending U.S. Appl. No. 15/784,647 dated Feb. 28, 2020.
Office Action issued in copending U.S. Appl. No. 15/784,555 dated Mar. 9, 2020.

(56) References Cited

OTHER PUBLICATIONS

Notice of Allowance issued in copending U.S. Appl. No. 15/784,775 dated Aug. 7, 2020.
Notice of Allowance issued in copending U.S. Appl. No. 15/784,555 dated Aug. 11, 2020.
Amendment and Statement on the Substance of the Interview filed in copending U.S. Appl. No. 15/725,662 dated Aug. 13, 2020.
Amendment and Statement on the Substance of the Interview filed in copending U.S. Appl. No. 15/725,731 dated Aug. 13, 2020.
Notice of Allowance issued in copending U.S. Appl. No. 15/784,722 dated Aug. 14, 2020.
Amendment filed in copending U.S. Appl. No. 16/407,379 dated Mar. 23, 2021.
Office Action issued in copending U.S. Appl. No. 16/407,379 dated Dec. 24, 2020.
Notice of Allowance issued in copending U.S. Appl. No. 15/725,662 dated Sep. 3, 2020.
Notice of Allowance issued in copending U.S. Appl. No. 15/725,731 dated Sep. 3, 2020.
Notice of Allowance issued in copending U.S. Appl. No. 15/697,744 dated Sep. 18, 2020.
Preliminary Amendment filed in copending U.S. Appl. No. 16/995,159 dated Sep. 25, 2020.
Preliminary Amendment filed in copending U.S. Appl. No. 16/995,222 dated Sep. 25, 2020.
Preliminary Amendment filed in copending U.S. Appl. No. 17/182,732 dated Mar. 11, 2021.
Preliminary Amendment filed in copending U.S. Appl. No. 17/072,262 dated Dec. 1, 2020.
Office Action issued in Chinese Appln. No. 201810941271.5 dated Nov. 3, 2020. English translation provided.
Copending U.S. Appl. No. 17/182,732, filed Feb. 23, 2021 (a copy is not yet available to the public and the Examiner has ready access to the cited application).
Preliminary Amendment filed in copending U.S. Appl. No. 17/182,732 dated Feb. 23, 2021.
Notice of Allowance issued in copending U.S. Appl. No. 16/407,379 dated Apr. 1, 2021.
Office Action issued in Chinese Application No. 201810941271.5 dated Jun. 3, 2021. English language Statement of Relevance provided.
Amendment filed in copending U.S. Appl. No. 15/287,988 dated Jul. 28, 2021.
Non-Final Office Action issued in copending U.S. Appl. No. 16/521,712 dated Sep. 30, 2021.
Copending U.S. Appl. No. 17/500,186, filed Oct. 13, 2021 (a copy is not yet available to the public and the Examiner has ready access to the cited application).
Preliminary Amendment filed in copending U.S. Appl. No. 17/500,186, filed Oct. 19, 2021.
Notice of Allowance issued in copending U.S. Appl. No. 15/299,640 dated Jun. 1, 2022.
Amendment and Statement on the Substance of the Interview filed in copending U.S. Appl. No. 17/584,705 dated Jun. 6, 2022.
Non-Final Office Action issued in copending U.S. Appl. No. 16/521,732 dated Jun. 10, 2022.
Notice of Allowance issued in copending U.S. Appl. No. 17/584,705 dated Jun. 22, 2022.
Non-Final Office Action issued in copending U.S. Appl. No. 16/521,745 dated Jun. 24, 2022.
Examination Report issued in Indian Application No. 9902/DELNP/2014 dated Jun. 19, 2020. English translation provided.
Office Action issued in copending U.S. Appl. No. 15/697,744 dated Jul. 8, 2020.
Amendment and Statement on the Substance of the Interview filed in copending U.S. Appl. No. 15/784,722 dated Jul. 9, 2020.
Amendment and Statement on the Substance of the Interview filed in copending U.S. Appl. No. 15/784,775 dated Jul. 9, 2020.
Amendment filed in copending U.S. Appl. No. 15/784,555 dated Jun. 3, 2020.
Notice of Allowance issued in copending U.S. Appl. No. 15/784,647 dated Jul. 23, 2020.
Supplemental Amendment filed in copending U.S. Appl. No. 15/299,640 dated Mar. 1, 2022.
Amendment filed in copending U.S. Appl. No. 16/369,528 dated Mar. 2, 2022.
Notice of Allowance issued in copending U.S. Appl. No. 16/658,820 dated Mar. 11, 2022.
Non-Final Office Action issued in copending U.S. Appl. No. 17/584,705 dated Mar. 29, 2022.
Amendment filed in copending U.S. Appl. No. 16/381,317 dated Apr. 4, 2022.
Amendment filed in copending U.S. Appl. No. 16/381,344 dated Apr. 4, 2022.
Response to Examination Opinion filed Mar. 18, 2021 for Chinese Patent Application No. 201810941271.5.
Office Action issued in copending U.S. Appl. No. 15/287,988 dated May 5, 2021.
Becker R. et al, "Ablation of Atrial Fibrillation: Energy Sources and Navigation Tools: A Review", Journal of Electrocardiology, 37 (Supplement 2004): 55-62, 2004.
Calkins, Hugh, "Radiofrequency Catheter Ablation of Supraventricular Arrhythmias", Heart, 85:594-600, 2001.
De Ponti et al., "Non-Fluoroscopic Mapping Systems for Electrophysiology: The 'Tool or Toy' Dilemma After 10 Years",European Heart Journal 27:1134-1136, 2006.
Gelbart et al, "Apparatus and Method for Intra-Cardiac Mapping and Ablation", Office Action dated Dec. 13, 2013; Notice of Allowance dated Jul. 25, 2014 for U.S. Appl. No. 11/475,950, 19 pgs.
Gelbart et al., "Medical Device for Use in Bodily Lumens, for Example an Atrium", Office Action dated Jan. 3, 2012; Office Action dated Apr. 3, 2014; Notice of Allowance dated Aug. 26, 2014 for U.S. Appl. No. 11/941,819, 35 pgs.
Gelbart et al, "Apparatus and Method for Intra-Cardiac Mapping and Ablation", Amendment filed Apr. 10, 2014; Supplemental Amendment filed Feb. 12, 2013 for U.S. Appl. No. 11/475,950, 21 pgs.
Gelbart et al, "Apparatus and Method for Intra-Cardiac Mapping and Ablation", Preliminary Amendment filed Aug. 22, 2014; Preliminary Amendment filed Mar. 5, 2013 for U.S. Appl. No. 13/785,910, 10 pgs.
Gelbart et al, "Apparatus and Method for Intra-Cardiac Mapping and Ablation", Preliminary Amendment filed Aug. 22, 2014; Preliminary Amendment filed Mar. 5, 2013 for U.S. Appl. No. 13/785,931, 10 pgs.
Lopes et al., "Enhanced Medical Device for Use in Bodily Cavities, for Example an Atrium", Preliminary Amendment filed Oct. 22, 2013 for U.S. Appl. No. 13/942,354, 13 pgs.
Lopes et al, "Enhanced Medical Device for Use in Bodily Cavities, for Example an Atrium", Preliminary Amendment filed Aug. 20, 2014 for U.S. Appl. No. 13/782,889, 11 pgs.
Lopes et al, "Enhanced Medical Device for Use in Bodily Cavities, for Example an Atrium", Preliminary Amendment filed Mar. 14, 2013 for U.S. Appl. No. 13/782,867, 8 pgs.
Gelbart et al., "Medical Device for Use in Bodily Lumens, for Example an Atrium", Amendment filed Jul. 3, 2014; Amendment filed Apr. 2, 2012; Amendment filed Mar. 1, 2012; Amendment filed Nov. 23, 2011; Replacement drawings filed Feb. 13, 2008 for U.S. Appl. No. 11/941,819, 78 pgs.
Gelbart et al., "Medical Device for Use in Bodily Lumens, for Example an Atrium", Preliminary Amendment filed May 12, 2014; Preliminary Amendment filed May 2, 2014 for U.S. Appl. No. 14/229,305, 12 pgs.
Gelbart et al., "Medical Device for Use in Bodily Lumens, for Example an Atrium", Preliminary Amendment filed May 12, 2014; Preliminary Amendment filed May 2, 2014 for U.S. Appl. No. 14/229,250, 10 pgs.
Gelbart et al., Medical Device for Use in Bodily Lumens, for Example an Atrium, Amendment filed Sep. 22, 2014, for U.S. Appl. No. 13/070,215, 18 pgs.

(56) References Cited

OTHER PUBLICATIONS

Gelbart et al., Medical Device for Use in Bodily Lumens, for Example an Atrium, Office Action dated Jun. 20, 2014, for U.S. Appl. No. 13/070,215, 8 pgs.
Gelbart et al., "Medical Device for Use in Bodily Lumens, for Example an Atrium", Supplemental Notice of Allowance dated Oct. 6, 2014 for U.S. Appl. No. 11/941,819, 4 pgs.
Notice of Allowance issued in U.S. Appl. No. 13/793,213 dated Aug. 10, 2016.
Non-Final Office Action issued in U.S. Appl. No. 13/942,354 dated Aug. 4, 2016.
Notice of Allowance issued in U.S. Appl. No. 14/136,946 dated May 12, 2016.
Notice of Allowance issued in U.S. Appl. No. 13/782,867 dated Aug. 12, 2016.
Notice of Allowance issued in U.S. Appl. No. 13/782,903 dated Jul. 6, 2016.
Corrected Notice of Allowance issued in U.S. Appl. No. 13/782,903 dated Jul. 19, 2016.
Non-Final Office Action issued in U.S. Appl. No. 14/229,305, dated Apr. 29, 2016.
Office Action issued in copending U.S. Appl. No. 15/725,662 dated May 13, 2020.
Office Action issued in copending U.S. Appl. No. 15/725,731 dated May 15, 2020.
Amendment filed in copending U.S. Appl. No. 15/784,647 dated May 27, 2020.
Amendment filed in copending U.S. Appl. No. 15/697,744 dated May 27, 2020.
Amendment filed in copending U.S. Appl. No. 16/521,732 dated Aug. 26, 2022.
Amendment filed in copending U.S. Appl. No. 16/521,745 dated Aug. 18, 2022.
Notice of Allowance issued in copending U.S. Appl. No. 16/521,732 dated Nov. 8, 2022.
Office Action issued in copending U.S. Appl. No. 16/995,159 dated Nov. 15, 2022.
Office Action issued in copending U.S. Appl. No. 16/995,222 dated Nov. 17, 2022.
Amendment filed in copending U.S. Appl. No. 16/995,159 dated Jan. 24, 2023.
Amendment filed in copending U.S. Appl. No. 16/995,222 dated Jan. 24, 2023.
Notice of Allowance issued in copending U.S. Appl. No. 16/521,745 dated Feb. 1, 2023.
Response filed in copending U.S. Appl. No. 17/072,262 dated Feb. 13, 2023.
Non-Final Office Action issued in copending U.S. Appl. No. 16/995,222 dated Feb. 22, 2023.
Non-Final Office Action issued in copending U.S. Appl. No. 17/072,262 dated Feb. 23, 2023.
Notice of Allowance issued in copending U.S. Appl. No. 16/995,159 dated Feb. 23, 2023.
Response filed in copending U.S. Appl. No. 16/995,222, dated Mar. 14, 2023.
Communication under Rule 71(3) EPC issued in European Application No. 13172848.7, dated Mar. 24, 2023.
Response filed in copending U.S. Appl. No. 17/072,262, dated May 2, 2023.
Final Office Action issued in copending U.S. Appl. No. 17/072,262, dated Jun. 26, 2023.
Notice of Allowance issued in copending U.S. Appl. No. 16/995,222, dated Jul. 6, 2023.
Notice of Allowance issued in copending U.S. Appl. No. 17/072,262, dated Sep. 7, 2023.

* cited by examiner

HIGH-DENSITY ELECTRODE-BASED MEDICAL DEVICE SYSTEM

CROSS-REFERENCE TO RELATED APPLICATIONS

This application is a continuation of U.S. patent application Ser. No. 15/287,988, filed Oct. 7, 2016, now U.S. Pat. No. 11,259,867, issued Mar. 1, 2022, which is a continuation of U.S. patent application Ser. No. 13/793,213, filed Mar. 11, 2013, now U.S. Pat. No. 9,480,525, issued Nov. 1, 2016, which:

(a) is a continuation-in-part of prior International Application No. PCT/US2012/022061, which has an international filing date of Jan. 20, 2012, and which claims the benefit of each of U.S. Provisional Application No. 61/435,213, filed Jan. 21, 2011; U.S. Provisional Application No. 61/485,987, filed May 13, 2011; U.S. Provisional Application No. 61/488,639, filed May 20, 2011; and U.S. Provisional Application No. 61/515,141, filed Aug. 4, 2011;

(b) is a continuation-in-part of prior International Application No. PCT/US2012/022062, which has an international filing date of Jan. 20, 2012, and which claims the benefit of each of U.S. Provisional Application No. 61/435,213, filed Jan. 21, 2011; U.S. Provisional Application No. 61/485,987, filed May 13, 2011; U.S. Provisional Application No. 61/488,639, filed May 20, 2011; and U.S. Provisional Application No. 61/515,141, filed Aug. 4, 2011; and (c) claims the benefit of each of U.S. Provisional Application No. 61/649,734, filed May 21, 2012; U.S. Provisional Application No. 61/670,881, filed Jul. 12, 2012; U.S. Provisional Application No. 61/723,311, filed Nov. 6, 2012; and U.S. Provisional Application No. 61/734,750, filed Dec. 7, 2012. The entire disclosure of each of the applications cited in this Cross-Reference to Related Applications Section is hereby incorporated herein by reference.

TECHNICAL FIELD

Aspects of this disclosure generally are related to a medical device system including a high-density arrangement of transducers. In some embodiments, the transducers are configured to ablate or sense characteristics of tissue inside a bodily cavity.

BACKGROUND

Cardiac surgery was initially undertaken using highly invasive open procedures. A sternotomy, which is a type of incision in the center of the chest that separates the sternum was typically employed to allow access to the heart. In the past several decades, more and more cardiac operations are performed using intravascular or percutaneous techniques, where access to inner organs or other tissue is gained via a catheter.

Intravascular or percutaneous surgeries benefit patients by reducing surgery risk, complications and recovery time. However, the use of intravascular or percutaneous technologies also raises some particular challenges. Medical devices used in intravascular or percutaneous surgery need to be deployed via catheter systems which significantly increase the complexity of the device structure. As well, doctors do not have direct visual contact with the medical devices once the devices are positioned within the body.

One example of where intravascular or percutaneous medical techniques have been employed is in the treatment of a heart disorder called atrial fibrillation. Atrial fibrillation is a disorder in which spurious electrical signals cause an irregular heartbeat. Atrial fibrillation has been treated with open heart methods using a technique known as the "Cox-Maze procedure". During this procedure, physicians create specific patterns of lesions in the left and right atria to block various paths taken by the spurious electrical signals. Such lesions were originally created using incisions, but are now typically created by ablating the tissue with various techniques including radio-frequency (RF) energy, microwave energy, laser energy and cryogenic techniques. The procedure is performed with a high success rate under the direct vision that is provided in open procedures, but is relatively complex to perform intravascularly or percutaneously because of the difficulty in creating the lesions in the correct locations. Various problems, potentially leading to severe adverse results, may occur if the lesions are placed incorrectly. It is particularly important to know the position of the various transducers which will be creating the lesions relative to cardiac features such as the pulmonary veins and mitral valve. The continuity, transmurality, and placement of the lesion patterns that are formed can impact the ability to block paths taken within the heart by spurious electrical signals. Other requirements for various ones of the transducers to perform additional functions such as, but not limited to, mapping various anatomical features, mapping electrophysiological activity, sensing tissue characteristics such as impedance and temperature and tissue stimulation can also complicate the operation of the employed medical device.

However, conventional transducer-based intra-bodily-cavity devices have relatively few transducers due to conventional technological limitations and, consequently, have difficulty gathering adequate information and performing proper lesion formation. Accordingly, a need in the art exists for improved intra-bodily-cavity transducer-based devices.

SUMMARY

At least the above-discussed need is addressed and technical solutions are achieved by various embodiments of the present invention. In some embodiments, device systems exhibit enhanced capabilities for the deployment and the activation of various transducers, which may be located within a bodily cavity, such as an intra-cardiac cavity. In some embodiments, systems or a portion thereof may be percutaneously or intravascularly delivered to position the various transducers within the bodily cavity. Various ones of the transducers may be activated to distinguish tissue from blood and may be used to deliver positional information of the device relative to various anatomical features in the bodily cavity, such as the pulmonary veins and mitral valve in an atrium. Various ones of the transducers may employ characteristics such as blood flow detection, impedance change detection or deflection force detection to discriminate between blood and tissue. Various ones of the transducers may be used to treat tissue within a bodily cavity. Treatment may include tissue ablation by way of non-limiting example. Various ones of the transducers may be used to stimulate tissue within the bodily cavity. Stimulation can include pacing by way of non-limiting example. Other advantages will become apparent from the teaching herein to those of skill in the art.

In some embodiments, a medical device system may be summarized as including a structure that includes a plurality of elongate members, each of the elongate members including a proximal end, a distal end, and an intermediate portion between the proximal and distal ends. The medical device system further includes a plurality of electrodes located on the structure, the plurality of electrodes positionable in a bodily cavity. A first group of the electrodes is located on a first elongate member of the plurality of elongate members and a second group of the electrodes is located on a second elongate member of the plurality of elongate members. The structure is selectively moveable between a delivery configuration in which the structure is sized to be percutaneously delivered to the bodily cavity and a deployed configuration in which the structure is expanded to have a size too large to be percutaneously delivered to the bodily cavity. The intermediate portions of the elongate members are angularly arranged with respect to one another about a first axis when the structure is in the deployed configuration. Each electrode of the first group of the electrodes is intersected by a first plane having no thickness and each electrode of the second group of the electrodes is intersected by a second plane having no thickness when the structure is in the deployed configuration. The first and the second planes are non-parallel planes that intersect each other along a second axis, and at least a first electrode of the plurality of electrodes is intersected by each of the first plane and the second plane when the structure is in the deployed configuration. The first electrode is not intersected by each of the first axis and the second axis when the structure is in the deployed configuration.

In some embodiments, the second axis is parallel to the first axis. In some embodiments, the first axis and the second axis are collinear. In some embodiments, the first axis intersects at least one other electrode of the plurality of electrodes that does not include the first electrode when the structure is in the deployed configuration. In some embodiments, the second axis intersects at least one other electrode of the plurality of electrodes that does not include the first electrode when the structure is in the deployed configuration.

Each of the plurality of elongate members may include a curved portion having a curvature configured to cause the curved portion to extend along at least a portion of a respective curved path, the curvature configured to cause the curved path to intersect the first axis at each of a respective at least two spaced apart locations along the first axis when the structure is in the deployed configuration. At least some of the plurality of electrodes may be radially spaced about the first axis when the structure is in the deployed configuration. At least some of the plurality of electrodes may be circumferentially arranged about the first axis when the structure is in the deployed configuration. The intermediate portion of the first elongate member may overlap the intermediate portion of the second elongate member at a location on the structure passed through by the first axis when the structure is in the deployed configuration. The intermediate portion of the first elongate member may overlap the intermediate portion of the second elongate member at each of a first location on the structure passed through by the first axis and a second location on the structure passed through by the second axis when the structure is in the deployed configuration. Each of the plurality of elongate members may be arranged to be advanced distal end-first into the bodily cavity when the structure is in the delivery configuration. The intermediate portion of the first elongate member may be adjacent the intermediate portion of the second elongate member when the structure is in the deployed configuration.

In some embodiments, the first group of the electrodes may include a pair of adjacent ones of the electrodes located on the first elongate member. A region of space associated with a physical portion of the structure may be located between the respective electrodes of the pair of adjacent ones of the electrodes located on the first elongate member, the region of space intersected by the first plane when the structure is in the deployed configuration. The respective electrodes of the first group of the electrodes may be spaced along a length of a portion of the first elongate member, the length of the portion of the first elongate member extending along the first elongate member between the proximal and the distal ends of the first elongate member. The entirety of the length of the portion of the elongate member may be intersected by the first plane when the structure is in the deployed configuration. The first group of the electrodes, the second group of the electrodes, or each of both the first and the second groups of the electrodes may include three or more of the plurality of electrodes.

In some embodiments, the first plane may intersect every electrode that is located on the first elongate member when the structure is in the deployed configuration. In some embodiments, the second plane may intersect every electrode that is located on the second elongate member when the structure is in the deployed configuration. In some embodiments, the first group of the electrodes includes the first electrode and the second group of the electrodes does not include the first electrode. At least some of the plurality of electrodes may be arranged in a plurality of concentric ringed arrangements when the structure is in the deployed configuration, a first one of the plurality of concentric ringed arrangements having a fewer number of the electrodes than a second one of the plurality of concentric ringed arrangements. The first one of the plurality of concentric ringed arrangements may include the first electrode.

The first elongate member may include an edge interrupted by a notch, the notch located to expose at least a portion of at least a second electrode located on the second elongate member as viewed towards the second electrode along a direction parallel to a direction that the first axis extends along when the structure is in the deployed configuration. The second group of the electrodes may include the second electrode. The second electrode may be adjacent the first electrode when the structure is in the deployed configuration.

In some embodiments, the first elongate member may include a surface interrupted by a channel, the channel located to expose at least a portion of at least a second electrode located on the second elongate member as viewed towards the second electrode along a direction parallel to a direction that the first axis extends along when the structure is in the deployed configuration. In some embodiments, the first elongate member may include a jogged portion, the jogged portion undergoing at least one change in direction as the jogged portion extends between the proximal and the distal ends of the first elongate member. The jogged portion may be located to expose at least a portion of at least a second electrode located on the second elongate member as viewed towards the second electrode along a direction parallel to a direction that the first axis extends along when the structure is in the deployed configuration. In some embodiments, the intermediate portion of each elongate member of the plurality of elongate members includes a front surface and a back surface opposite across a thickness of the elongate member from the front surface. Each intermediate portion further includes a respective pair of side edges of the front surface, the back surface, or both the front surface and the back surface of the intermediate portion. The side edges of each pair of side edges are opposite to one another, each of the side edges of each pair of side edges extending between the proximal end and the distal end of the respective elongate member. The first elongate member may be positioned such that a first edge of the pair of side edges of the first elongate member crosses a second side edge of the pair of side edges of the second elongate member of the plurality of elongate members when the structure is in the deployed configuration. A portion of the first edge may form a recessed portion of the first elongate member that exposes at least a portion of a second electrode located on a portion of the front surface of the second elongate member as viewed normally to the portion of the front surface of the second elongate member when the structure is in the deployed configuration. The second group of the electrodes may include the second electrode.

In some embodiments, each of the respective intermediate portions of the elongate members each may include a thickness, a front surface, and a back surface opposite across the thickness from the front surface. The respective intermediate portions of the plurality of elongate members may be arranged front surface-toward-back surface in a stacked array when the structure is in the delivery configuration. The structure may further include a proximal portion and a distal portion, each of the proximal and the distal portions including a respective part of each of the plurality of elongate members, the proximal portion of the structure forming a first domed shape and the distal portion of the structure forming a second domed shape when the structure is in the deployed configuration.

The structure may include a proximal portion and a distal portion with the structure arranged to be advanced distal portion first into the bodily cavity when the structure is in the delivery configuration. In some embodiments, the proximal portion of the structure forms a first domed shape and the distal portion of the structure forms a second domed shape when the structure is in the deployed configuration, the proximal and the distal portions of the structure arranged in a clam shell configuration when the structure is in the deployed configuration.

In some embodiments, the intermediate portions of at least some of the plurality of elongate members are, when the structure is in the deployed configuration, sufficiently spaced from the first axis to position each of at least some of the plurality of the electrodes at respective locations suitable for contact with a tissue wall of the bodily cavity.

Various systems may include combinations and subsets of the systems summarized above.

In some embodiments, a medical device system may be summarized as including a plurality of transducers positionable in a bodily cavity and a structure on which the transducers are located. The structure includes a plurality of elongate members, each of the elongate members including a proximal end, a distal end, an intermediate portion positioned between the proximal end and the distal end, and a thickness. Each intermediate portion includes a front surface and a back surface opposite across the thickness of the elongate member from the front surface, and each intermediate portion further includes a respective pair of side edges of the front surface, the back surface, or both the front surface and the back surface. The side edges of each pair of side edges are opposite to one another, and the side edges of each pair of side edges extend between the proximal end and the distal end of the respective elongate member. The structure is selectively moveable between a delivery configuration in which the structure is sized for percutaneous delivery to a bodily cavity, and a deployed configuration in which the structure is sized too large for percutaneous delivery to the bodily cavity. At least a first elongate member of the plurality of elongate members is positioned such that a first edge of the pair of side edges of the first elongate member crosses a second side edge of the pair of side edges of a second elongate member of the plurality of elongate members when the structure is in the deployed configuration. A portion of the first edge forms a recessed portion of the first elongate member that exposes at least a portion of a transducer located on a portion of the front surface of the second elongate member as viewed normally to the portion of the front surface of the second elongate member when the structure is in the deployed configuration.

The recessed portion of the first elongate member may form at least a portion of a notch in the intermediate portion of the first elongate member, the notch extending towards a second edge of the pair of side edges of the first elongate member. The first elongate member may include a jogged portion, the jogged portion undergoing at least one change in direction as the jogged portion extends between the proximal and the distal ends of the first elongate member, the recessed portion of the first elongate member forming at least part of the jogged portion.

The intermediate portions of the elongate members may be angularly arranged with respect to one another about an axis when the structure is in the deployed configuration. At least some of the plurality of transducers may be radially spaced about an axis when the structure is in the deployed configuration. At least some of the plurality of transducers may be circumferentially arranged about an axis when the structure is in the deployed configuration. At least some of the plurality of transducers may be arranged in a plurality of concentric ringed arrangements when the structure is in the deployed configuration, a first one of the plurality of concentric ringed arrangements having a fewer number of the transducers than a second one of the plurality of concentric ringed arrangements. The first one of the plurality of concentric ringed arrangements may not include any of the plurality of transducers located on the second elongate member. The second one of the plurality of concentric ringed arrangements may include the transducer located on the portion of the front surface of the second elongate member. The first one of the plurality of concentric ringed arrangements may be adjacent the second one of the plurality of concentric ringed arrangements.

Each of the plurality of elongate members may be arranged to be advanced distal end-first into the bodily cavity when the structure is in the delivery configuration. The respective intermediate portions of the plurality of elongate members may be arranged front surface-toward-back surface in a stacked array when the structure is in the delivery configuration. The structure may further include a proximal portion and a distal portion, each of the proximal and the distal portions including a respective part of each of the plurality of elongate members, the proximal portion of the structure forming a first domed shape and the distal portion of the structure forming a second domed shape when the structure is in the deployed configuration.

The structure may include a proximal portion and a distal portion, with the structure arranged to be advanced distal portion first into the bodily cavity when the structure is in the delivery configuration. In some embodiments, the proximal portion of the structure forms a first domed shape and the distal portion of the structure forms a second domed shape when the structure is in the deployed configuration, the proximal and the distal portions of the structure arranged in a clam shell configuration when the structure is in the deployed configuration.

Various systems may include combinations and subsets of the systems summarized above.

In some embodiments, a medical device system may be summarized as including a plurality of electrodes positionable in a bodily cavity and a structure on which the electrodes are located. The structure includes a plurality of elongate members. The plurality of electrodes include a plurality of sets of the electrodes, each respective set of the electrodes located on a respective one of the elongate members. Each of the elongate members includes a proximal end, a distal end, an intermediate portion positioned between the proximal end and the distal end, and a thickness. Each intermediate portion includes a front surface and a back surface opposite across the thickness of the elongate member from the front surface. The structure is selectively moveable between a delivery configuration in which the structure is sized for percutaneous delivery to the bodily cavity and a deployed configuration in which the structure is sized too large for percutaneous delivery to the bodily cavity. A first elongate member of the plurality of elongate members is positioned such that a portion of the front surface of the first elongate member overlaps a portion of the respective front surface of each of at least a second elongate member of the plurality of elongate members as viewed normally to the portion of the front surface of the first elongate member when the structure is in the deployed configuration. At least a first electrode of the plurality of electrodes is located at least on the portion of the front surface of the first elongate member, and the portion of the front surface of the second elongate member faces the back surface of the first elongate member at least when the structure is in the deployed configuration.

Each of the front surfaces of the plurality of elongate members may face an outward direction of the structure when the structure is in the deployed configuration. The portion of the front surface of the second elongate member may face the back surface of the first elongate member when the structure is in the delivery configuration. The portion of the front surface of the second elongate member may contact the back surface of the first elongate member when the structure is in the deployed configuration. Each electrode in each set of the plurality of electrodes may be located solely on the front surface of a respective one of the elongate members.

The intermediate portions of the elongate members may be angularly arranged with respect to one another about an axis when the structure is in the deployed configuration. At least some of the plurality of electrodes may be radially spaced about the axis when the structure is in the deployed configuration. At least some of the plurality of electrodes may be circumferentially arranged about the axis when the structure is in the deployed configuration. The intermediate portion of the first elongate member may cross the intermediate portion of the second elongate member at a location on the structure intersected by the axis when the structure is in the deployed configuration. Each of the portion of the front surface of the first elongate member and the portion of the front surface of the second elongate member may be intersected by the axis when the structure is in the deployed configuration. The intermediate portion of the first elongate member may be adjacent the intermediate portion of the second elongate member when the structure is in the deployed configuration. At least one electrode of the plurality of electrodes may be intersected by the axis when the structure is in the deployed configuration. A particular electrode of the at least one electrode may be located adjacently to the first electrode on the portion of the front surface of the first elongate member. At least some of the plurality of electrodes may be arranged in a plurality of concentric ringed arrangements when the structure is in the deployed configuration, a first one of the plurality of concentric ringed arrangements having a fewer number of the electrodes than a second one of the plurality of concentric ringed arrangements. The first one of the plurality of concentric ringed arrangements may include the first electrode.

Each intermediate portion may further include a respective pair of side edges of the front surface, the back surface, or both the front surface and the back surface of the intermediate portion. The side edges of each pair of side edges are opposite to one another, and each of the side edges of each pair of side edges extend between the proximal end and the distal end of the respective elongate member. The first elongate member may be positioned such that a first edge of the pair of side edges of the first elongate member crosses a second side edge of the pair of side edges of the second elongate member when the structure is in the deployed configuration. A portion of the first edge may form a recessed portion of the first elongate member that exposes at least a portion of a second electrode located on the portion of the front surface of the second elongate member as viewed normally to the portion of the front surface of the second elongate member when the structure is in the deployed configuration.

Each of the plurality of elongate members may be arranged to be advanced distal end-first into the bodily cavity when the structure is in the delivery configuration. The respective intermediate portions of the plurality of elongate members may be arranged front surface-toward-back surface in a stacked array when the structure is in the delivery configuration. The structure may further include a proximal portion and a distal portion, each of the proximal and the distal portions including a respective part of each of the plurality of elongate members. In some embodiments, the proximal portion of the structure forms a first domed shape and the distal portion of the structure forms a second domed shape when the structure is in the deployed configuration.

The structure may include a proximal portion and a distal portion, with the structure arranged to be advanced distal portion first into the bodily cavity when the structure is in the delivery configuration. In some embodiments, the proximal portion of the structure forms a first domed shape and the distal portion of the structure forms a second domed shape when the structure is in the deployed configuration, the proximal and the distal portions of the structure arranged in a clam shell configuration when the structure is in the deployed configuration.

Various systems may include combinations and subsets of the systems summarized above.

In some embodiments, a medical device system may be summarized as including a plurality of electrodes positionable in a bodily cavity and a structure on which the electrodes are located. The structure includes a plurality of elongate members, each of the elongate members including a proximal end, a distal end, an intermediate portion positioned between the proximal end and the distal end, and a thickness. Each intermediate portion includes a front surface and a back surface opposite across the thickness of the elongate member from the front surface. Each intermediate portion further includes a respective pair of side edges of the front surface, the back surface, or both the front surface and the back surface. The side edges of each pair of side edges opposite to one another. The side edges of each pair of side edges extend between the proximal end and the distal end of the respective elongate member. The structure is selectively moveable between a delivery configuration in which the structure is sized for percutaneous delivery to a bodily cavity and a deployed configuration in which the structure is sized too large for percutaneous delivery to the bodily cavity. At least a first elongate member of the plurality of elongate members is positioned such that a first side edge of the pair of side edges of the first elongate member crosses a first side edge of the pair of side edges of a second elongate member of the plurality of elongate members at a first location and crosses a second side edge of the pair of side edges of the second elongate member at a second location when the structure is in the deployed configuration. Each of one or more of the plurality of electrodes is wholly located on a portion of the second elongate member, the portion of the second elongate member located between a first transverse line and a second transverse line when the structure is in the deployed configuration, the first transverse line extending across a first width of the second elongate member at the first location, and the second transverse line extending across a second width of the second elongate member at the second location.

The first width may be different than the second width. The first width and the second width may be widths of the front surface of the second elongate member. The one or more electrodes may include two or more of the plurality of electrodes. At least a portion of an electrode of the plurality of electrodes may be located on the portion of the second elongate member.

A first electrode of the one or more of the plurality of electrodes may include a first electrode edge that forms part of a periphery of an electrically conductive surface of the first electrode, the first electrode edge arranged to follow a portion of the first side edge of the first elongate member between the first location and the second location when the structure is in the deployed configuration. The first electrode may include a second electrode edge opposite across the electrically conductive surface from the first electrode edge, the second electrode edge forming part of the periphery of the electrically conductive surface of the first electrode. The second electrode edge may be arranged to follow a portion of one of the pair of side edges of the second elongate member.

The intermediate portions of the elongate members may be angularly arranged with respect to one another about an axis when the structure is in the deployed configuration. At least some of the plurality of electrodes may be radially spaced about the axis when the structure is in the deployed configuration. At least some of the plurality of electrodes may be circumferentially arranged about the axis when the structure is in the deployed configuration. The intermediate portion of the first elongate member may cross the intermediate portion of the second elongate member at a location on the structure intersected by the axis when the structure is in the deployed configuration. The intermediate portion of the first elongate member may be adjacent the intermediate portion of the second elongate member when the structure is in the deployed configuration. A particular one of the plurality of electrodes may be intersected by the axis when the structure is in the deployed configuration. The one or more electrodes may include a first electrode, the first electrode located on the structure adjacent the particular one of the plurality of electrodes when the structure is in the deployed configuration. The one or more electrodes may include a first electrode, and at least some of the plurality of electrodes may be arranged in a plurality of concentric ringed arrangements when the structure is in the deployed configuration. In some embodiments, a first one of the plurality of concentric ringed arrangements has a fewer number of the electrodes than a second one of the plurality of concentric ringed arrangements. The first one of the plurality of concentric ringed arrangements may include the first electrode.

A portion of the first side edge of the first elongate member extending between the first location and the second location may form a recessed portion of the first elongate member that exposes at least a portion of a particular electrode of the one or more electrodes as viewed normally to a surface of the exposed portion of the particular electrode of the one or more electrodes when the structure is in the deployed configuration.

Each of the plurality of elongate members may be arranged to be advanced distal end-first into the bodily cavity when the structure is in the delivery configuration. The respective intermediate portions of the plurality of elongate members may be arranged front surface-toward-back surface in a stacked array when the structure is in the delivery configuration. The structure may further include a proximal portion and a distal portion, each of the proximal and the distal portions including a respective part of each of the plurality of elongate members. In some embodiments, the proximal portion of the structure forms a first domed shape and the distal portion of the structure forms a second domed shape when the structure is in the deployed configuration.

The structure may include a proximal portion and a distal portion, with the structure arranged to be advanced distal portion first into the bodily cavity when the structure is in the delivery configuration. In some embodiments, the proximal portion of the structure forms a first domed shape and the distal portion of the structure forms a second domed shape when the structure is in the deployed configuration, the proximal and the distal portions of the structure arranged in a clam shell configuration when the structure is in the deployed configuration.

Various systems may include combinations and subsets of all the systems summarized above.

BRIEF DESCRIPTION OF THE DRAWINGS

It is to be understood that the attached drawings are for purposes of illustrating aspects of various embodiments and may include elements that are not to scale.

DETAILED DESCRIPTION

Figure 1:
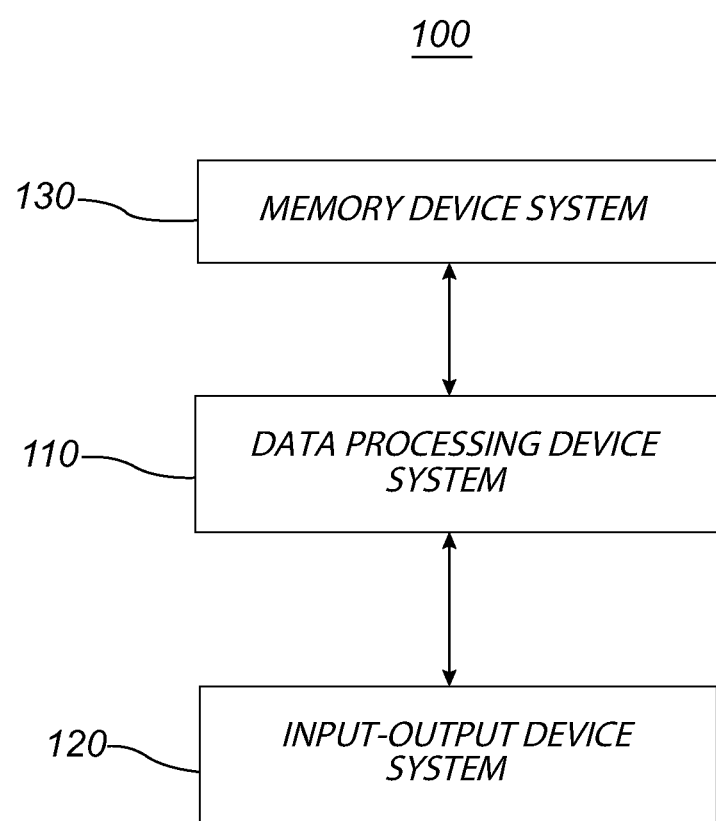
FIG. 1 is a schematic representation of a transducer-activation system according to example embodiments, the transducer-activation system including a data processing device system, an input-output device system, and a memory device system.

In the following description, certain specific details are set forth in order to provide a thorough understanding of various embodiments of the invention. However, one skilled in the art will understand that the invention may be practiced without one or more of these details. In other instances, well-known structures (e.g., structures associated with radio-frequency (RF) ablation and electronic controls such as multiplexers) have not been shown or described in detail to avoid unnecessarily obscuring descriptions of various embodiments of the invention.

Reference throughout this specification to "one embodiment" or "an embodiment" or "an example embodiment" or "an illustrated embodiment" or "a particular embodiment" and the like means that a particular feature, structure or characteristic described in connection with the embodiment is included in at least one embodiment. Thus, the appearances of the phrases "in one embodiment" or "in an embodiment" or "in an example embodiment" or "in this illustrated embodiment" or "in this particular embodiment" and the like in various places throughout this specification are not necessarily all referring to the same embodiment. Furthermore, the particular features, structures or characteristics of different embodiments may be combined in any suitable manner to form one or more other embodiments.

It is noted that, unless otherwise explicitly noted or required by context, the word "or" is used in this disclosure in a non-exclusive sense. In addition, unless otherwise explicitly noted or required by context, the word "set" is intended to mean one or more.

Further, the phrase "at least" is used herein at times to emphasize the possibility that other elements can exist besides those explicitly listed. However, unless otherwise explicitly noted (such as by the use of the term "only") or required by context, non-usage herein of the phrase "at least" does not exclude the possibility that other elements can exist besides those explicitly listed. For example, the phrase, "activation of at least transducer A" includes activation of transducer A by itself, as well as activation of transducer A and activation of one or more other additional elements besides transducer A. In the same manner, the phrase, "activation of transducer A" includes activation of transducer A by itself, as well as activation of transducer A and activation of one or more other additional elements besides transducer A. However, the phrase, "activation of only transducer A" includes only activation of transducer A, and excludes activation of any other elements besides transducer A.

The word "ablation" as used in this disclosure should be understood to include any disruption to certain properties of tissue. Most commonly, the disruption is to the electrical conductivity and is achieved by heating, which can be generated with resistive or radio-frequency (RF) techniques for example. Other properties, such as mechanical or chemical, and other means of disruption, such as optical, are included when the term "ablation" is used.

The word "fluid" as used in this disclosure should be understood to include any fluid that can be contained within a bodily cavity or can flow into or out of, or both into and out of a bodily cavity via one or more bodily openings positioned in fluid communication with the bodily cavity. In the case of cardiac applications, fluid such as blood will flow into and out of various intra-cardiac cavities (e.g., a left atrium or right atrium).

The words "bodily opening" as used in this disclosure should be understood to include a naturally occurring bodily opening or channel or lumen; a bodily opening or channel or lumen formed by an instrument or tool using techniques that can include, but are not limited to, mechanical, thermal, electrical, chemical, and exposure or illumination techniques; a bodily opening or channel or lumen formed by trauma to a body; or various combinations of one or more of the above. Various elements having respective openings, lumens or channels and positioned within the bodily opening (e.g., a catheter sheath or catheter introducer) may be present in various embodiments. These elements may provide a passageway through a bodily opening for various devices employed in various embodiments.

The words "bodily cavity" as used in this disclosure should be understood to mean a cavity in a body. The bodily cavity may be a cavity provided in a bodily organ (e.g., an intra-cardiac cavity of a heart).

The word "tissue" as used in some embodiments in this disclosure should be understood to include any surface-forming tissue that is used to form a surface of a body or a surface within a bodily cavity, a surface of an anatomical feature or a surface of a feature associated with a bodily opening positioned in fluid communication with the bodily cavity. The tissue can include part or all of a tissue wall or membrane that defines a surface of the bodily cavity. In this regard, the tissue can form an interior surface of the cavity that surrounds a fluid within the cavity. In the case of cardiac applications, tissue can include tissue used to form an interior surface of an intra-cardiac cavity such as a left atrium or right atrium. In some embodiments, the word tissue can refer to a tissue having fluidic properties (e.g., blood).

The term "transducer" as used in this disclosure should be interpreted broadly as any device capable of distinguishing between fluid and tissue, sensing temperature, creating heat, ablating tissue, measuring electrical activity of a tissue surface, stimulating tissue, or any combination thereof. A transducer can convert input energy of one form into output energy of another form. Without limitation, a transducer can include an electrode that functions as, or as part of, a sensing device included in the transducer, an energy delivery device included in the transducer, or both a sensing device and an energy delivery device included in the transducer. A transducer may be constructed from several parts, which may be discrete components or may be integrally formed.

The term "activation" as used in this disclosure should be interpreted broadly as making active a particular function as related to various transducers disclosed in this disclosure. Particular functions can include, but are not limited to, tissue ablation, sensing electrophysiological activity, sensing temperature and sensing electrical characteristics (e.g., tissue impedance). For example, in some embodiments, activation of a tissue ablation function of a particular transducer is initiated by causing energy sufficient for tissue ablation from an energy source device system to be delivered to the particular transducer. Alternatively, in this example, the activation can be deemed to be initiated when the particular transducer causes a temperature sufficient for the tissue ablation due to the energy provided by the energy source device system. Also in this example, the activation can last for a duration of time concluding when the ablation function is no longer active, such as when energy sufficient for the tissue ablation is no longer provided to the particular transducer. Alternatively, in this example, the activation period can be deemed to be concluded when the temperature caused by the particular transducer is below the temperature sufficient for the tissue ablation. In some contexts, however, the word "activation" can merely refer to the initiation of the activating of a particular function, as opposed to referring to both the initiation of the activating of the particular function and the subsequent duration in which the particular function is active. In these contexts, the phrase or a phrase similar to "activation initiation" may be used.

The term "program" in this disclosure should be interpreted as a set of instructions or modules that can be executed by one or more components in a system, such as a controller system or data processing device system, in order to cause the system to perform one or more operations. The set of instructions or modules can be stored by any kind of memory device, such as those described subsequently with respect to the memory device system 130 shown in FIG. 1. In addition, instructions or modules of a program may be described as being configured to cause the performance of a function. The phrase "configured to" in this context is intended to include at least (a) instructions or modules that are presently in a form executable by one or more data processing devices to cause performance of the function (e.g., in the case where the instructions or modules are in a compiled and unencrypted form ready for execution), and (b) instructions or modules that are presently in a form not executable by the one or more data processing devices, but could be translated into the form executable by the one or more data processing devices to cause performance of the function (e.g., in the case where the instructions or modules are encrypted in a non-executable manner, but through performance of a decryption process, would be translated into a form ready for execution). The word "module" can be defined as a set of instructions.

The word "device" and the phrase "device system" both are intended to include one or more physical devices or subdevices (e.g., pieces of equipment) that interact to perform one or more functions, regardless of whether such devices or subdevices are located within a same housing or different housings. In this regard, for example, the phrase "catheter device" could equivalently be referred to as a "catheter device system".

In some contexts, the term "adjacent" is used in this disclosure to refer to objects that do not have another substantially similar object between them. For example, object A and object B could be considered adjacent if they contact each other (and, thus, it could be considered that no other object is between them), or if they do not contact each other, but no other object that is substantially similar to object A, object B, or both objects A and B, depending on context, is between them.

Further, the phrase "in response to" might be used in the following context, where an event A occurs in response to the occurrence of an event B. In this regard, such phrase can include, for example, that at least the occurrence of the event B causes or triggers the event A.

FIG. 1 schematically illustrates a system 100 for activating transducers, according to some embodiments. The system 100 includes a data processing device system 110, an input-output device system 120, and a processor-accessible memory device system 130. The processor-accessible memory device system 130 and the input-output device system 120 are communicatively connected to the data processing device system 110.

Figure 2:
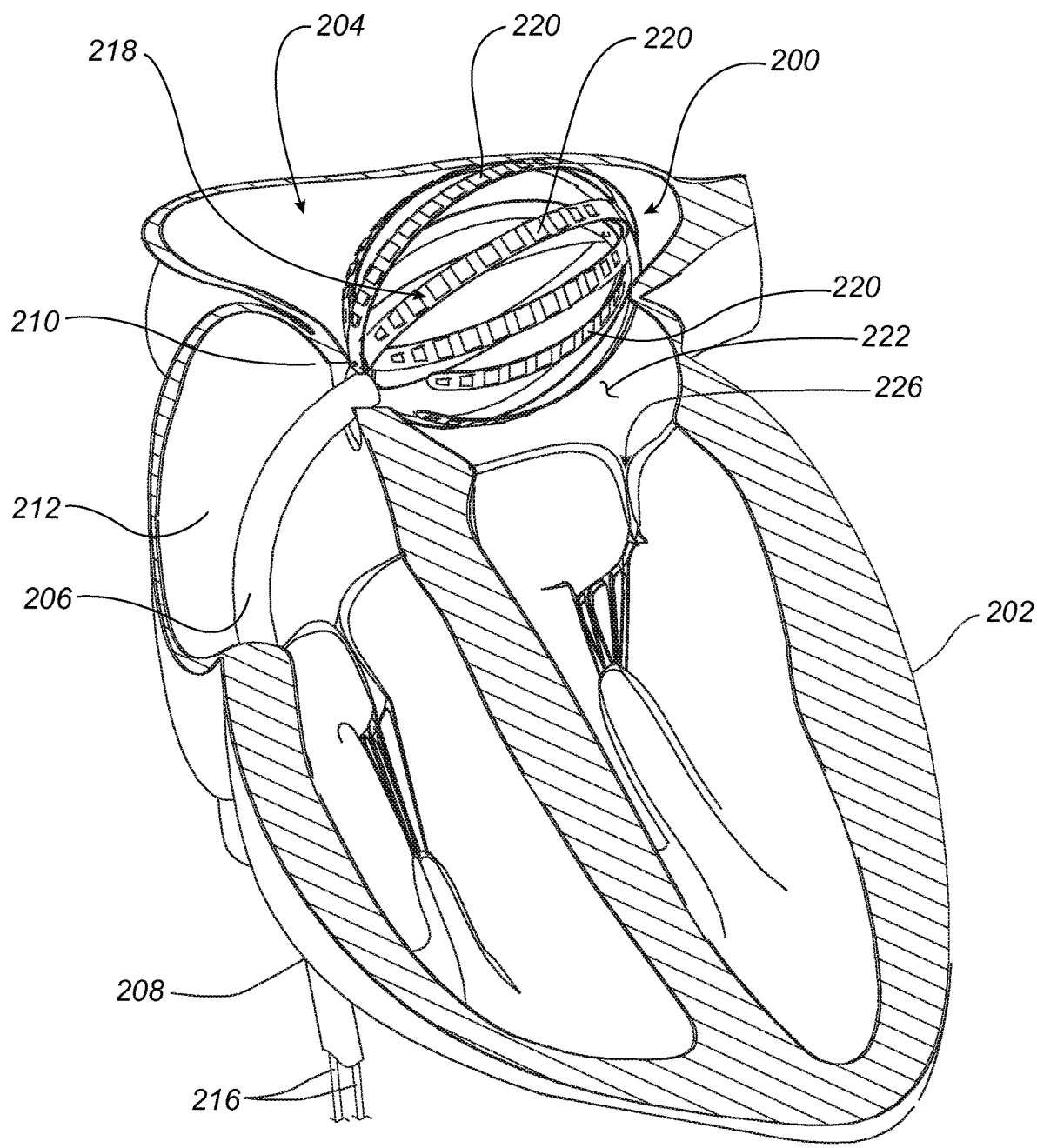
FIG. 2 is a cutaway diagram of a heart showing a transducer-based device percutaneously placed in a left atrium of the heart according to example embodiments.
Figure 3A:
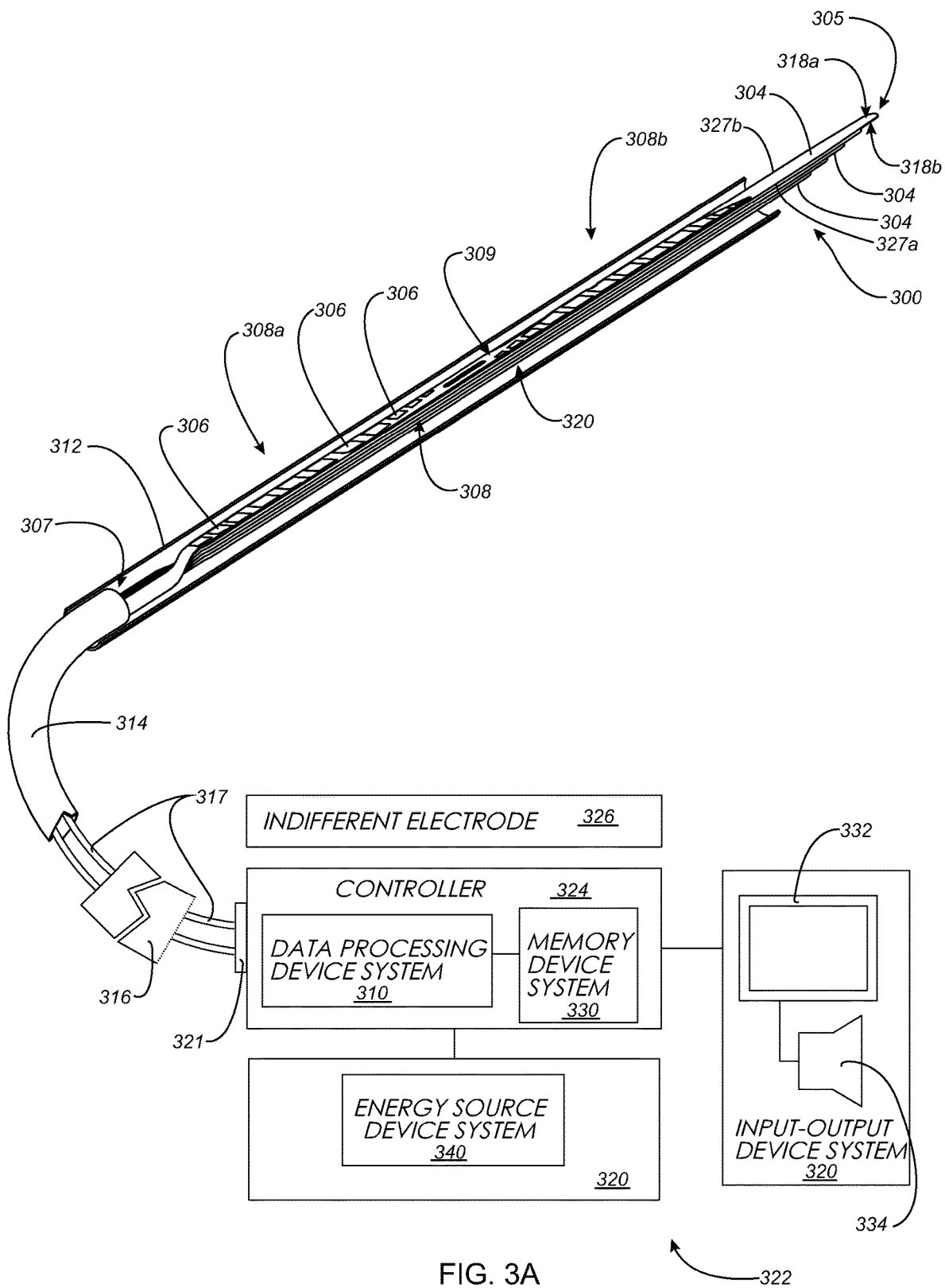
FIG. 3A is a partially schematic representation of a medical device system according to example embodiments, the medical device system including a data processing device system, an input-output device system, a memory device system, and a transducer-based device having a plurality of transducers and an expandable structure shown in a delivery or unexpanded configuration.
Figure 3B:
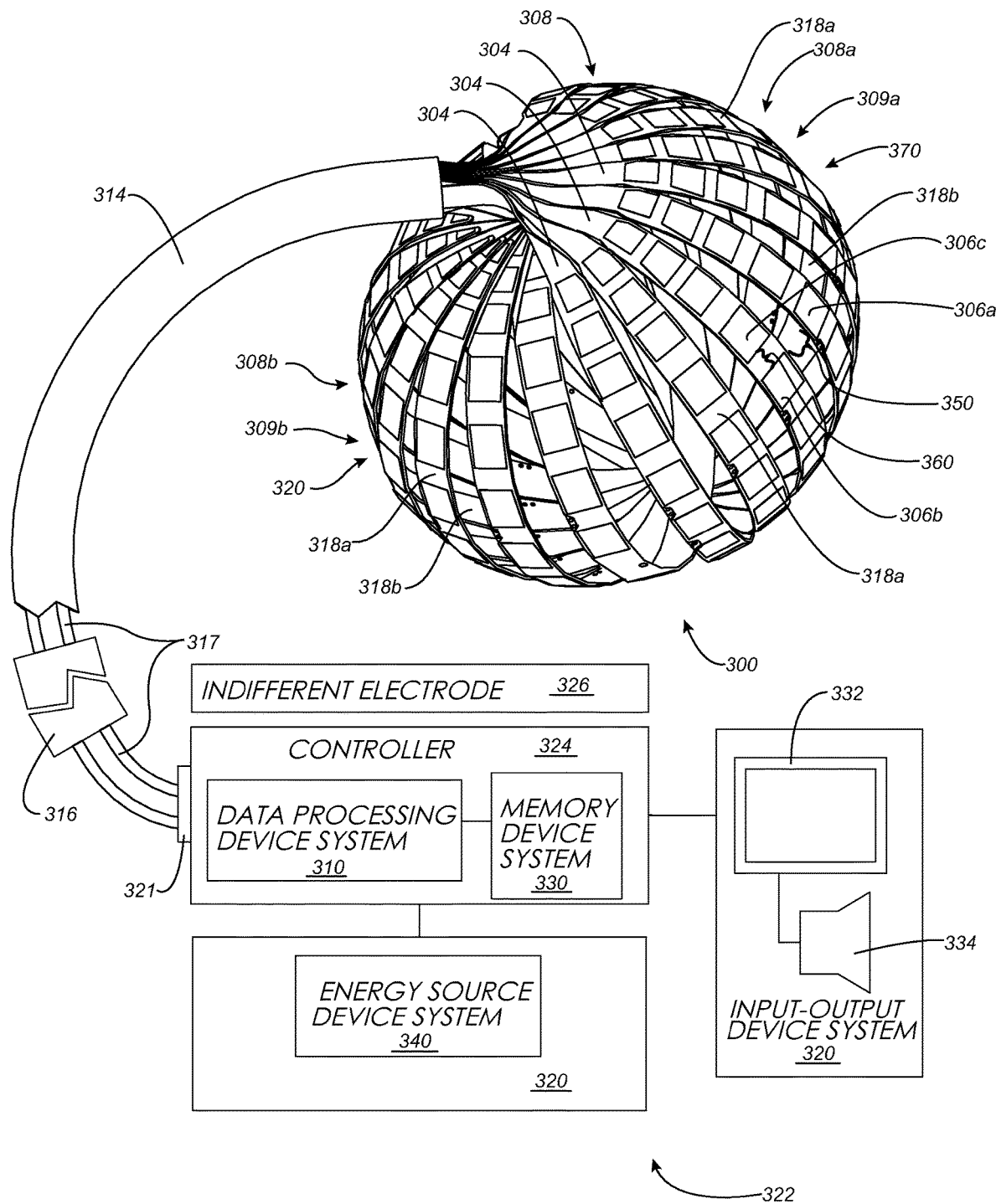
FIG. 3B is the medical device system of FIG. 3A with the expandable structure shown in a deployed or expanded configuration.
Figure 3C:
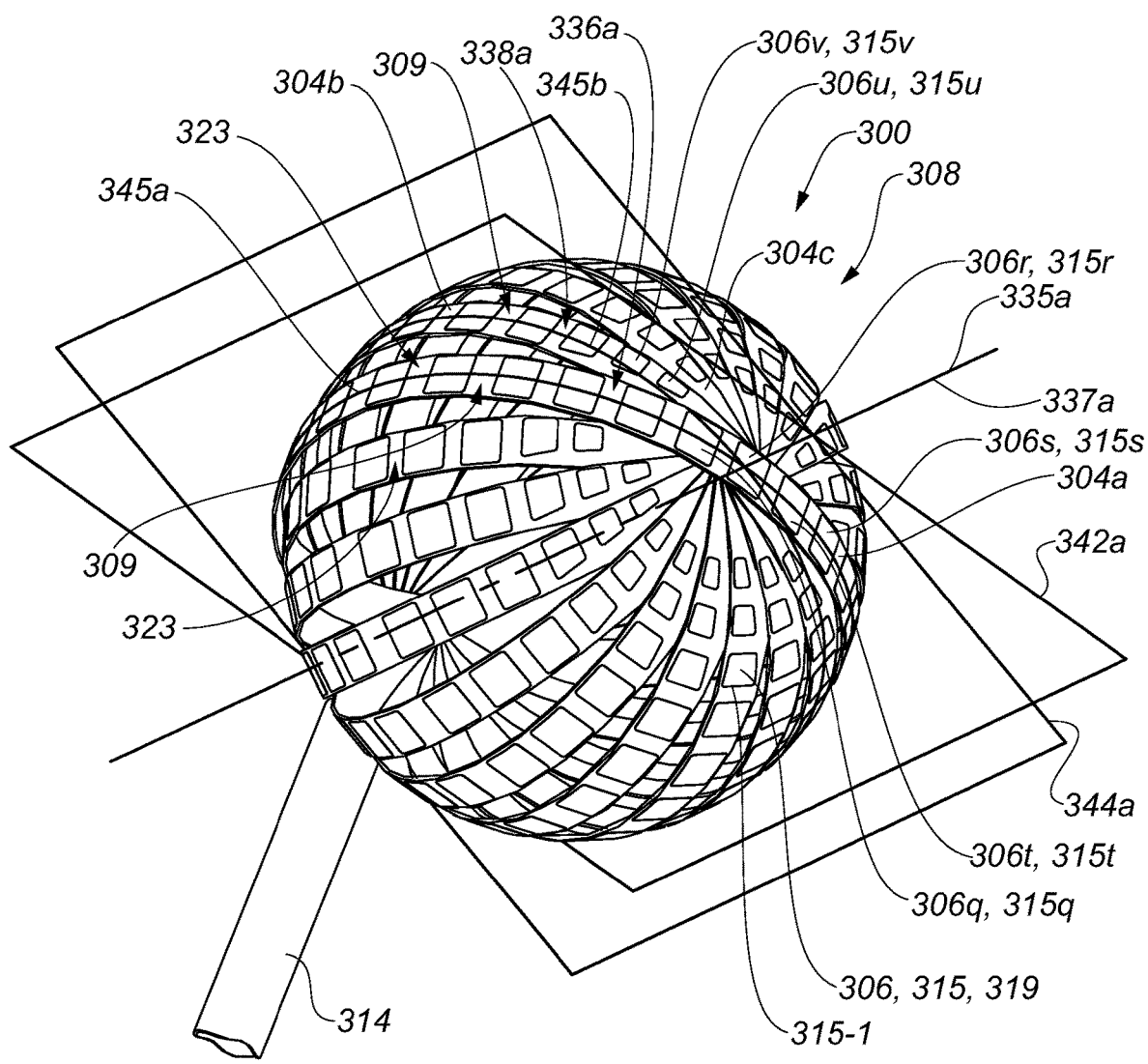
FIG. 3C is a representation of the expandable structure of the medical device system of FIG. 3A in the deployed configuration, as viewed from a different viewing angle than that employed in FIG. 3B.
Figure 3D:
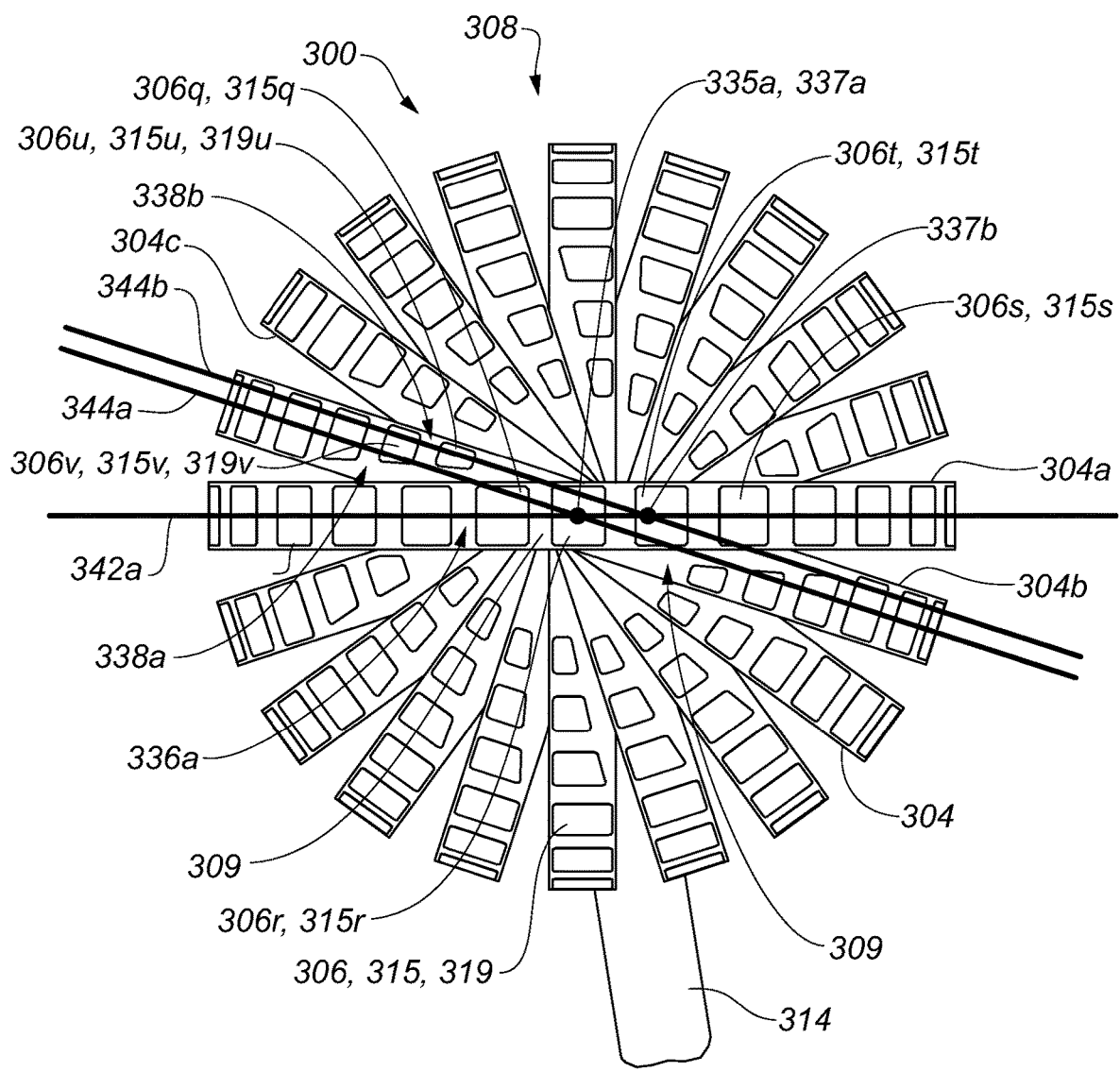
FIG. 3D is a plan view of the expandable structure of FIG. 3C.
Figure 3E:
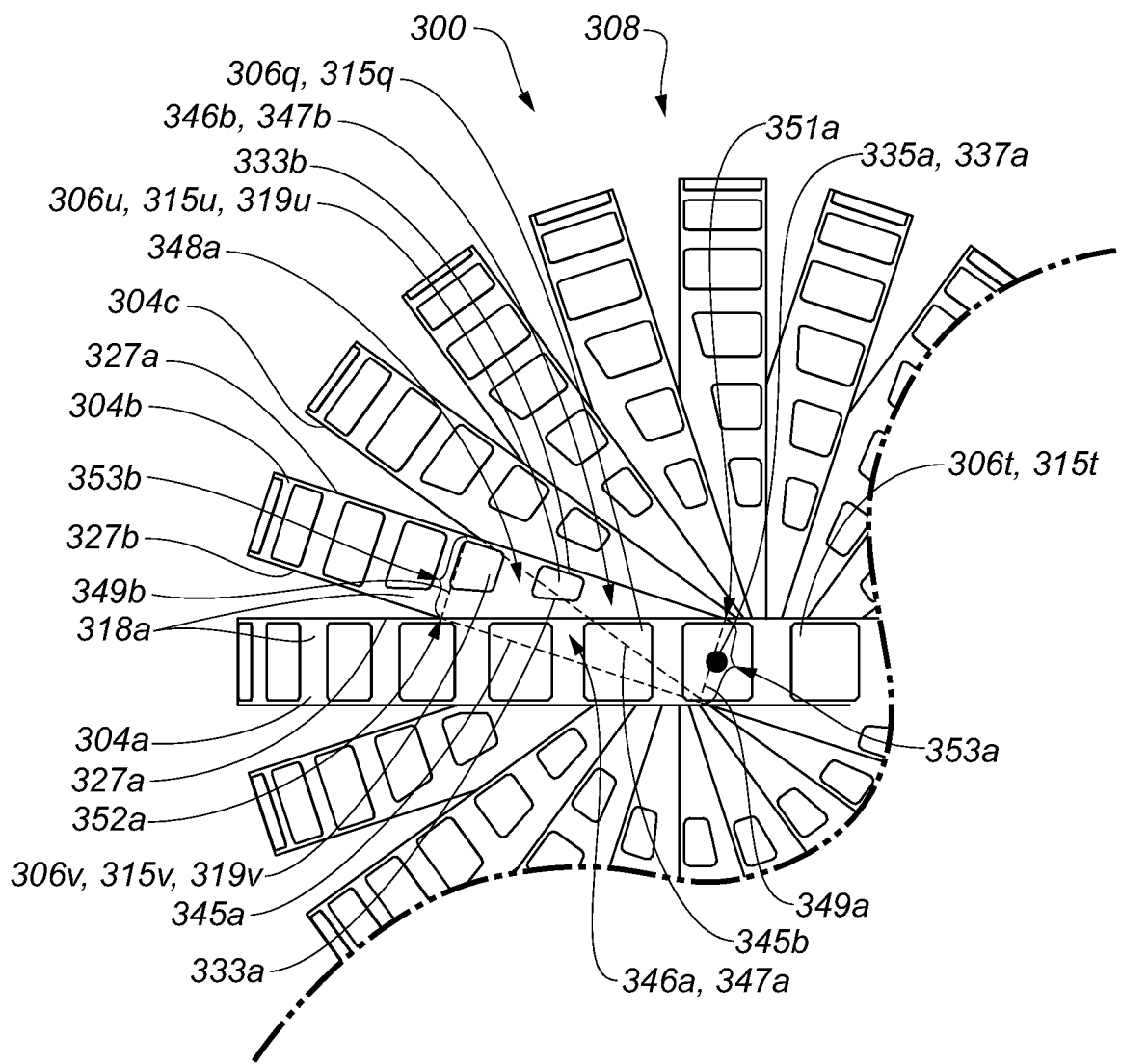
FIG. 3E is an enlarged view of a portion of the expandable structure of FIG. 3D.
Figure 3F:
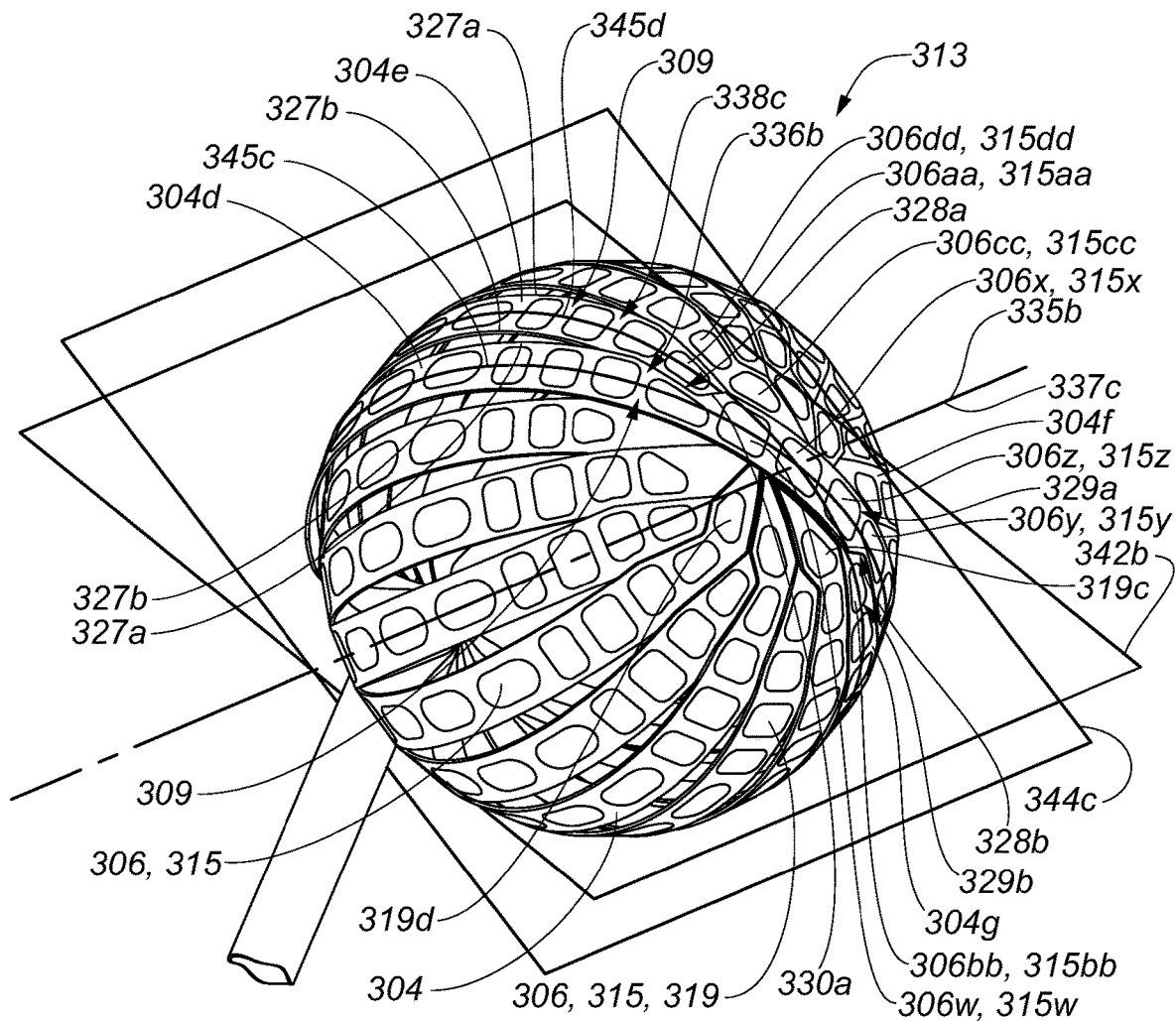
FIG. 3F is a representation of an expandable structure of a transducer-based device system according to various example embodiments, the expandable structure in a deployed configuration.
Figure 3G:
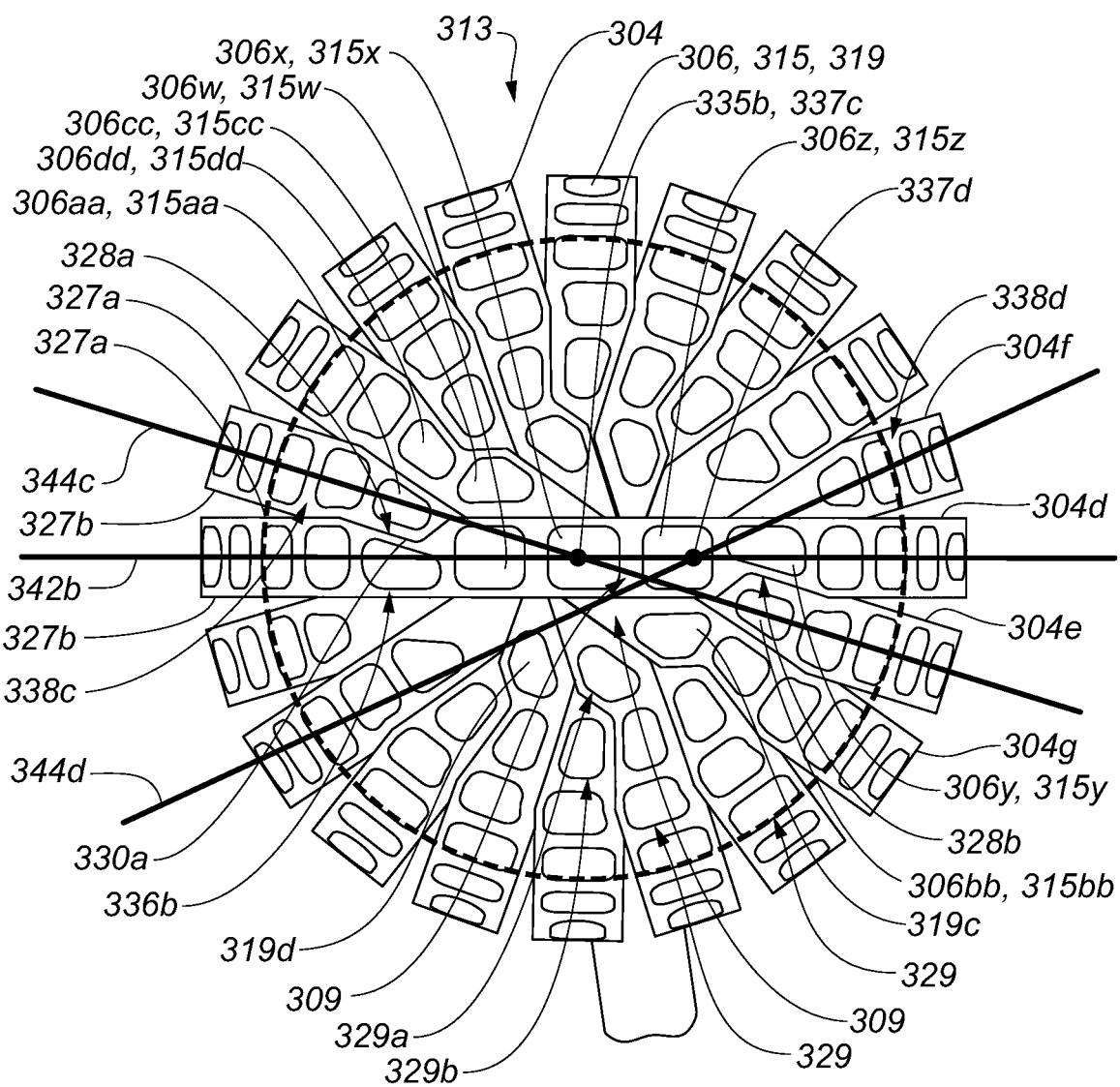
FIG. 3G is a plan view of the expandable structure of FIG. 3F.
Figure 3H:
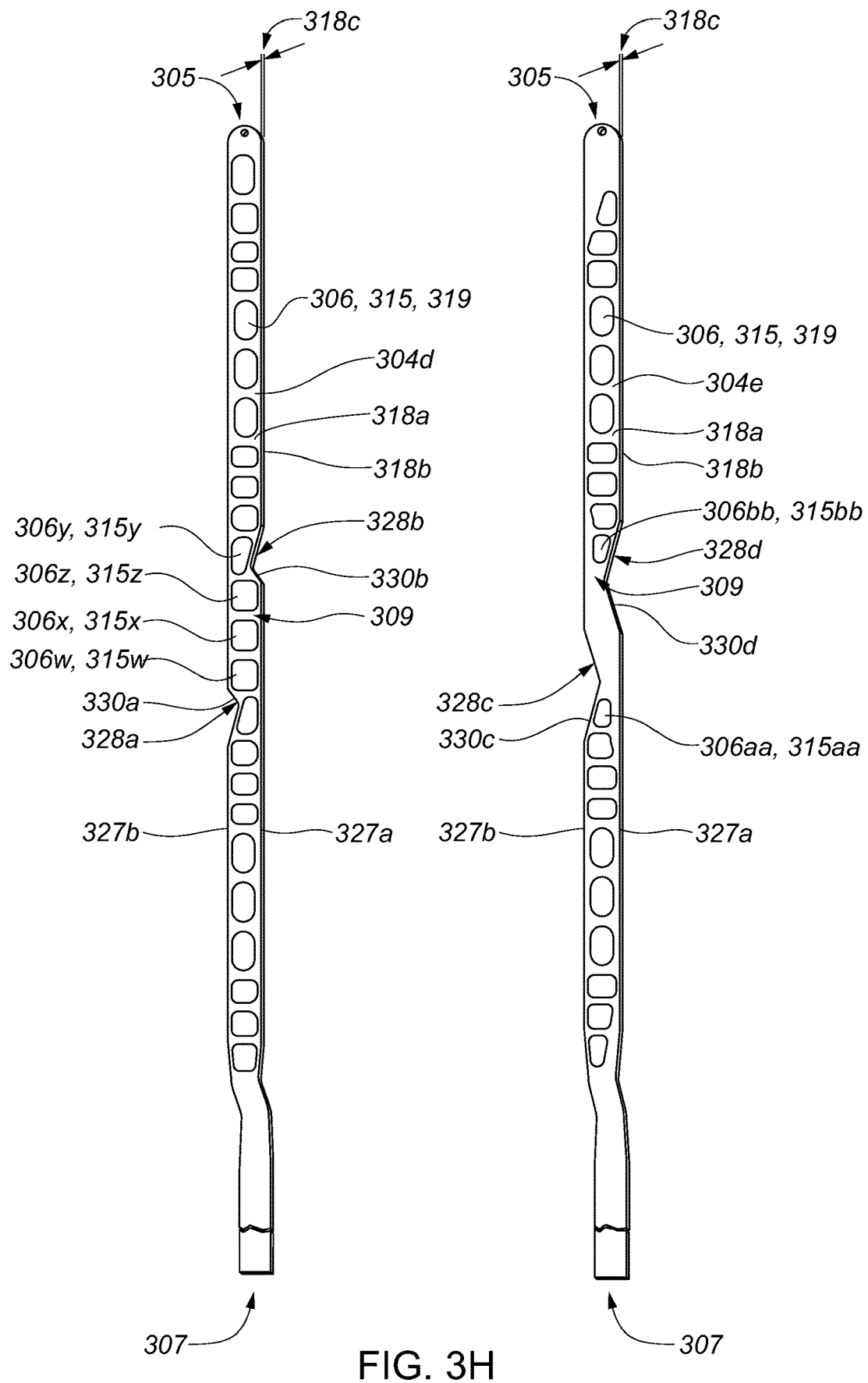
FIG. 3H is a perspective view of two of the elongate members of the expandable structure of FIGS. 3F and 3G, each of the elongate members shown in a flattened configuration.
Figure 3I:
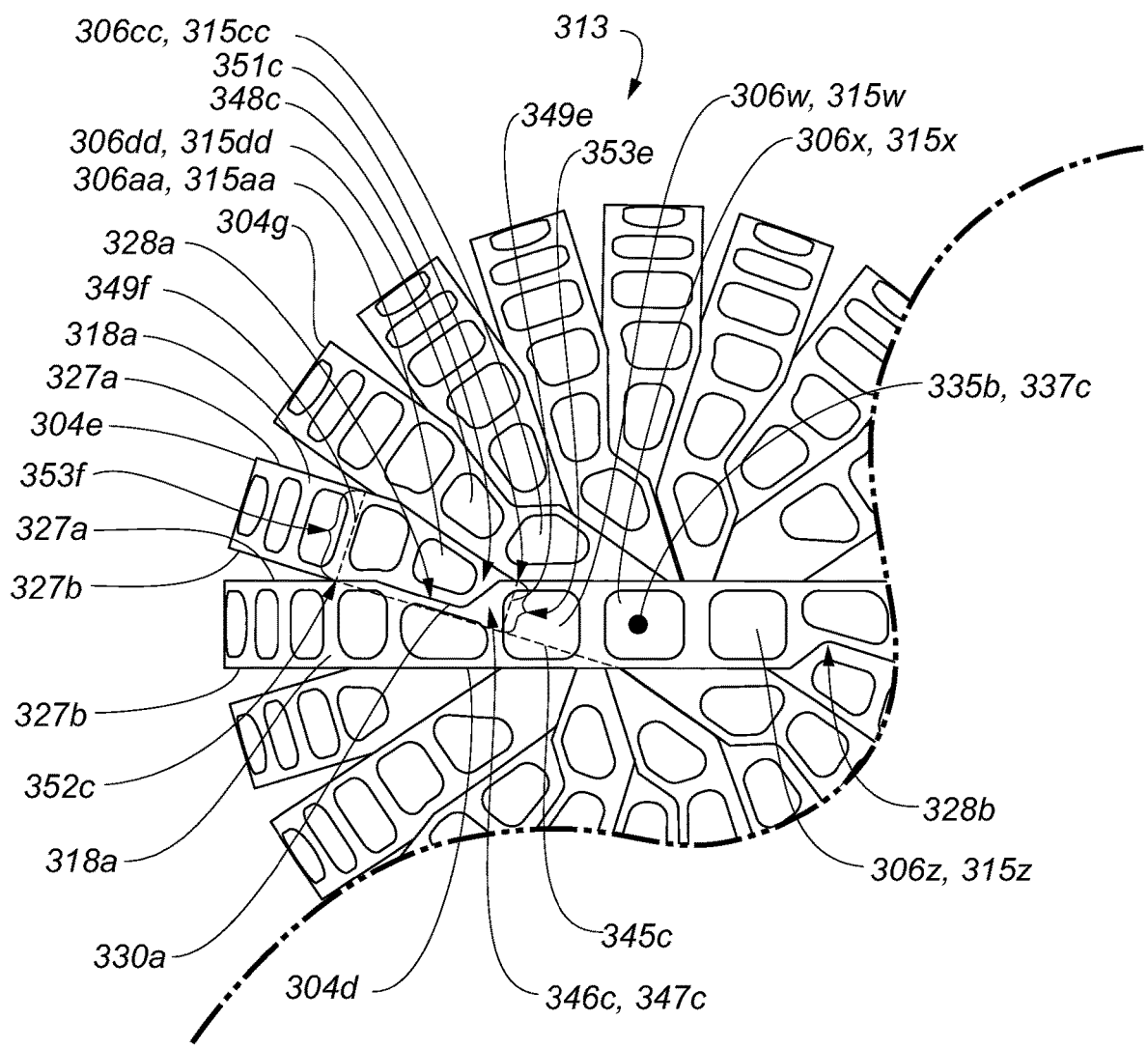
FIG. 3I is an enlarged view of a portion of the expandable structure of FIG. 3G.
Figure 3J:
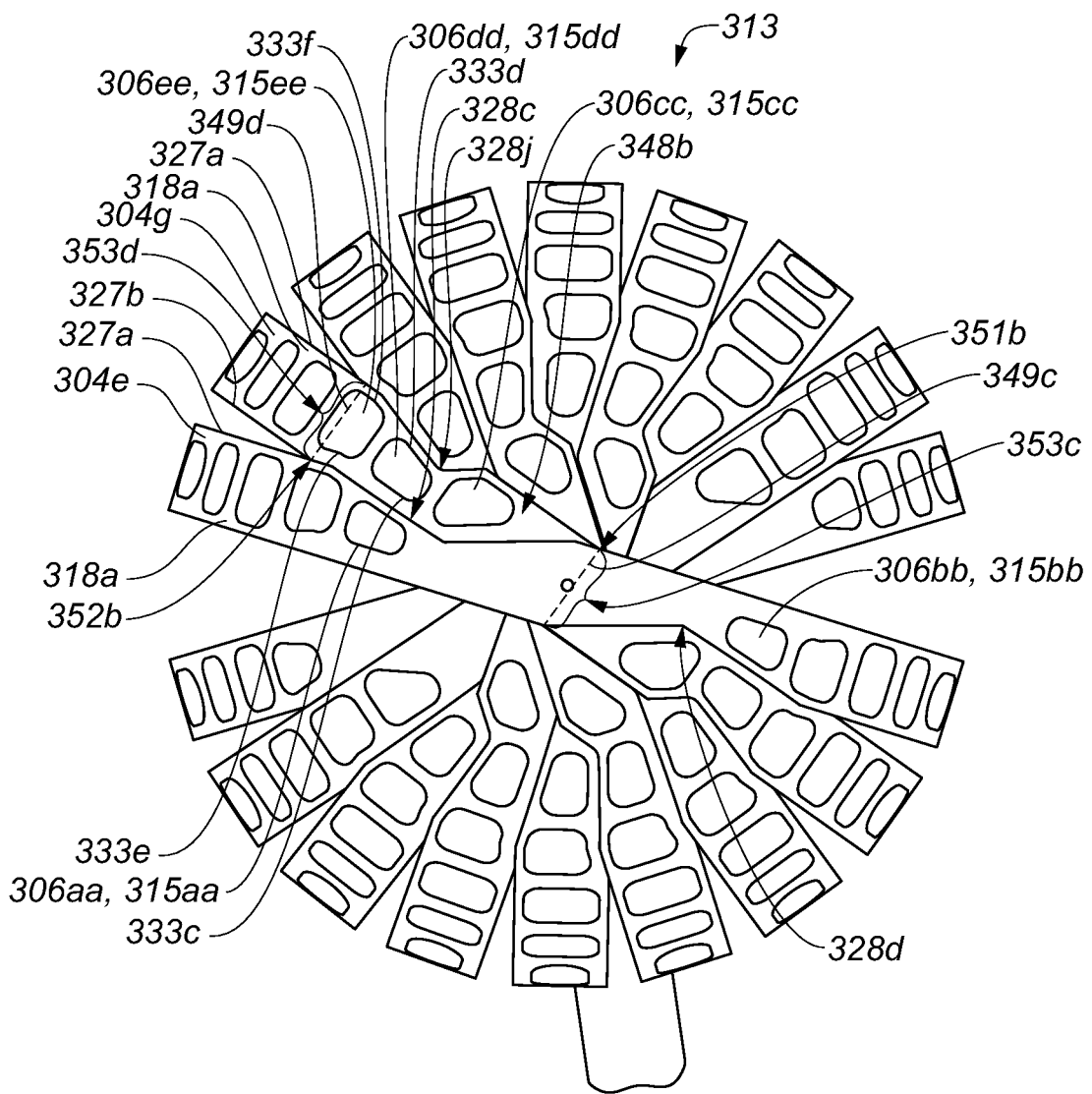
FIG. 3J is a plan view of the expandable structure of FIG. 3F with an elongate member of the structure omitted for clarity.
Figure 3K:
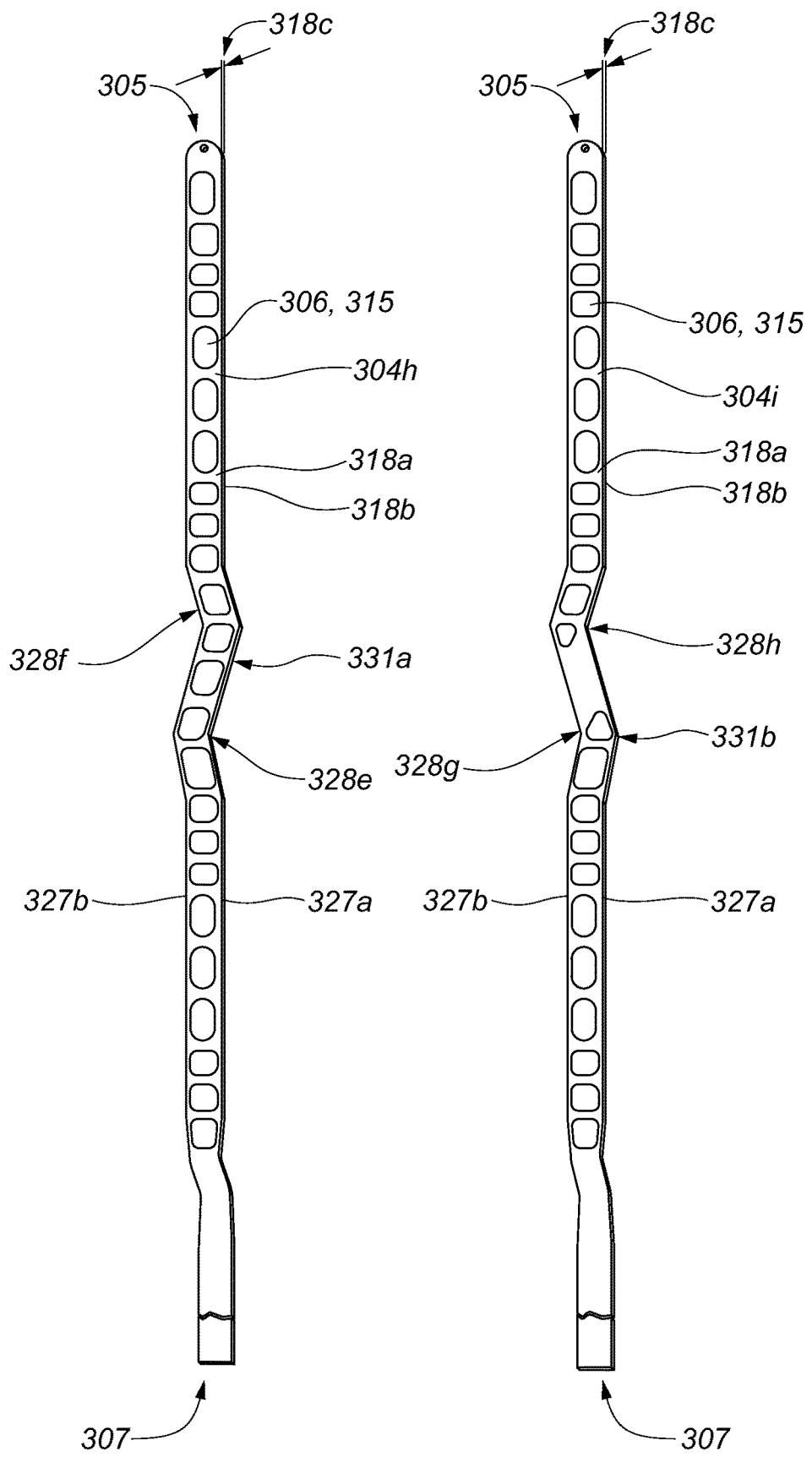
FIG. 3K is a perspective view of two elongate members of an expandable structure of a transducer-based device system according to various embodiments, each of the elongate members shown in a flattened configuration.
Figure 4:
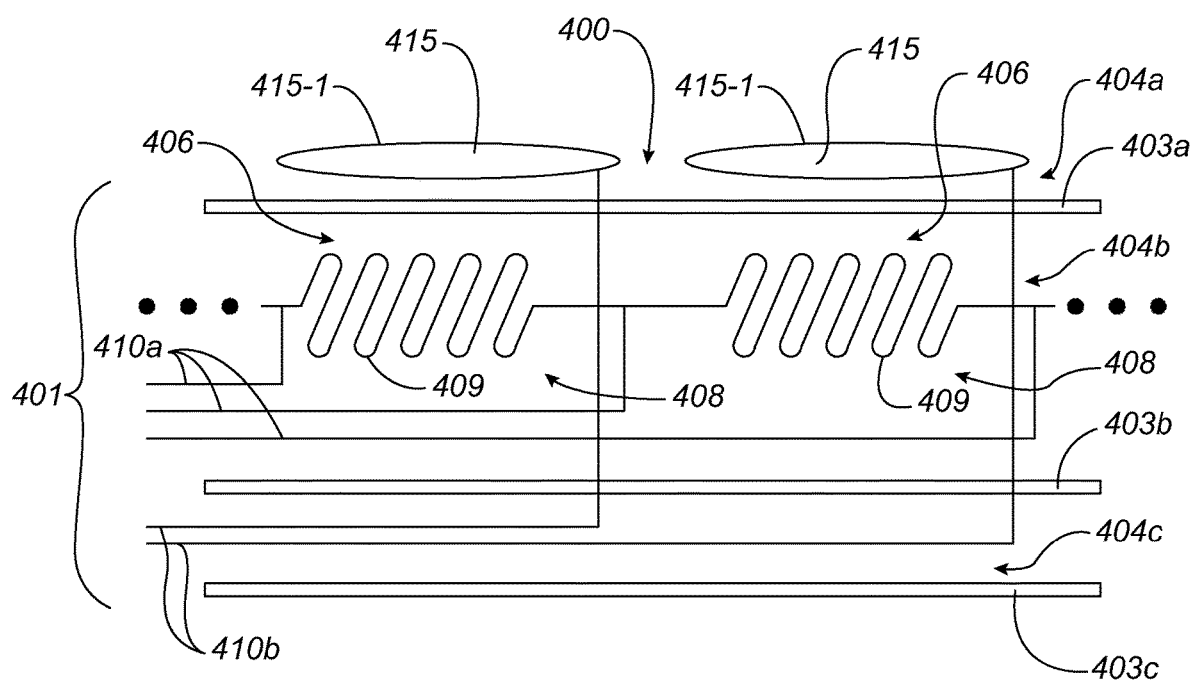
FIG. 4 is a schematic representation of a transducer-based device that includes a flexible circuit structure according to at least one example embodiment.

The data processing device system 110 includes one or more data processing devices that implement methods by controlling or interacting with various structural components described herein, including, but not limited to, various structural components illustrated in the other FIGS. 2-4. Each of the phrases "data processing device", "data processor", "processor", and "computer" is intended to include any data processing device, such as a central processing unit ("CPU"), a desktop computer, a laptop computer, a mainframe computer, a tablet computer, a personal digital assistant, a cellular phone, and any other device for processing data, managing data, or handling data, whether implemented with electrical, magnetic, optical, biological components, or otherwise.

The memory device system 130 includes one or more processor-accessible memory devices configured to store information, including the information needed to execute the methods implemented by the data processing device system 110. The memory device system 130 may be a distributed processor-accessible memory device system including multiple processor-accessible memory devices communicatively connected to the data processing device system 110 via a plurality of computers and/or devices. On the other hand, the memory device system 130 need not be a distributed processor-accessible memory system and, consequently, may include one or more processor-accessible memory devices located within a single housing or data processing device.

Each of the phrases "processor-accessible memory" and "processor-accessible memory device" is intended to include any processor-accessible data storage device, whether volatile or nonvolatile, electronic, magnetic, optical, or otherwise, including but not limited to, registers, floppy disks, hard disks, Compact Discs, DVDs, flash memories, ROMs, and RAMs. In some embodiments, each of the phrases "processor-accessible memory" and "processor-accessible memory device" is intended to include a non-transitory computer-readable storage medium. And in some embodiments, the memory device system 130 can be considered a non-transitory computer-readable storage medium system.

The phrase "communicatively connected" is intended to include any type of connection, whether wired or wireless, between devices, data processors, or programs in which data may be communicated. Further, the phrase "communicatively connected" is intended to include a connection between devices or programs within a single data processor, a connection between devices or programs located in different data processors, and a connection between devices not located in data processors at all. In this regard, although the memory device system 130 is shown separately from the data processing device system 110 and the input-output device system 120, one skilled in the art will appreciate that the memory device system 130 may be located completely or partially within the data processing device system 110 or the input-output device system 120. Further in this regard, although the input-output device system 120 is shown separately from the data processing device system 110 and the memory device system 130, one skilled in the art will appreciate that such system may be located completely or partially within the data processing system 110 or the memory device system 130, depending upon the contents of the input-output device system 120. Further still, the data processing device system 110, the input-output device system 120, and the memory device system 130 may be located entirely within the same device or housing or may be separately located, but communicatively connected, among different devices or housings. In the case where the data processing device system 110, the input-output device system 120, and the memory device system 130 are located within the same device, the system 100 of FIG. 1 can be implemented by a single application-specific integrated circuit (ASIC) in some embodiments.

The input-output device system 120 may include a mouse, a keyboard, a touch screen, another computer, or any device or combination of devices from which a desired selection, desired information, instructions, or any other data is input to the data processing device system 110. The input-output device system may include a user-activatable control system that is responsive to a user action. The input-output device system 120 may include any suitable interface for receiving information, instructions or any data from other devices and systems described in various ones of the embodiments. In this regard, the input-output device system 120 may include various ones of other systems described in various embodiments. For example, the input-output device system 120 may include at least a portion of a transducer-based device system. The phrase "transducer-based device system" is intended to include one or more physical systems that include one or more physical devices that include transducers.

The input-output device system 120 also may include an image generating device system, a display device system, a processor-accessible memory device, or any device or combination of devices to which information, instructions, or any other data is output by the data processing device system 110. In this regard, if the input-output device system 120 includes a processor-accessible memory device, such memory device may or may not form part or all of the memory device system 130. The input-output device system 120 may include any suitable interface for outputting information, instructions or data to other devices and systems described in various ones of the embodiments. In this regard, the input-output device system may include various other devices or systems described in various embodiments. For example, the input-output device system may include a portion of a transducer-based device system.

Various embodiments of transducer-based devices are described herein. Some of the described devices are medical devices that are percutaneously or intravascularly deployed. Some of the described devices are moveable between a delivery or unexpanded configuration in which a portion of the device is sized for passage through a bodily opening leading to a bodily cavity, and an expanded or deployed configuration in which the portion of the device has a size too large for passage through the bodily opening leading to the bodily cavity. An example of an expanded or deployed configuration is when the portion of the transducer-based device is in its intended-deployed-operational state inside the bodily cavity. Another example of the expanded or deployed configuration is when the portion of the transducer-based device is being changed from the delivery configuration to the intended-deployed-operational state to a point where the portion of the device now has a size too large for passage through the bodily opening leading to the bodily cavity.

In some example embodiments, the device includes transducers that sense characteristics (e.g., convective cooling, permittivity, force) that distinguish between fluid, such as a fluidic tissue (e.g., blood), and tissue forming an interior surface of the bodily cavity. Such sensed characteristics can allow a medical device system to map the cavity, for example using positions of openings or ports into and out of the cavity to determine a position or orientation (i.e., pose), or both of the portion of the device in the bodily cavity. In some example embodiments, the described devices are capable of ablating tissue in a desired pattern within the bodily cavity. In some example embodiments, the devices are capable of sensing characteristics (e.g., electrophysiological activity) indicative of whether an ablation has been successful. In some example embodiments, the devices are capable of providing stimulation (e.g., electrical stimulation) to tissue within the bodily cavity. Electrical stimulation may include pacing.

FIG. 2 shows a transducer-based device 200, which may be all or part of a medical device system, useful in investigating or treating a bodily organ, for example a heart 202, according to some example embodiments.

Transducer-based device 200 can be percutaneously or intravascularly inserted into a portion of the heart 202, such as an intra-cardiac cavity like left atrium 204. In this example, the transducer-based device 200 is part of a catheter 206 inserted via the inferior vena cava 208 and penetrating through a bodily opening in transatrial septum 210 from right atrium 212. In other embodiments, other paths may be taken.

Catheter 206 includes an elongated flexible rod or shaft member appropriately sized to be delivered percutaneously or intravascularly. Various portions of catheter 206 may be steerable. Catheter 206 may include one or more lumens (not shown). The lumen(s) may carry one or more communications or power paths, or both. For example, the lumens(s) may carry one or more electrical conductors 216 (two shown in this embodiment). Electrical conductors 216 provide electrical connections to device 200 that are accessible externally from a patient in which the transducer-based device 200 is inserted.

Transducer-based device 200 includes a frame or structure 218 which assumes an unexpanded configuration for delivery to left atrium 204. Structure 218 is expanded (i.e., shown in a deployed or expanded configuration in FIG. 2) upon delivery to left atrium 204 to position a plurality of transducers 220 (three called out in FIG. 2) proximate the interior surface formed by tissue 222 of left atrium 204. In some embodiments, at least some of the transducers 220 are used to sense a physical characteristic of a fluid (i.e., blood) or tissue 222, or both, that may be used to determine a position or orientation (i.e., pose), or both, of a portion of a device 200 within, or with respect to left atrium 204. For example, transducers 220 may be used to determine a location of pulmonary vein ostia (not shown) or a mitral valve 226, or both. In some embodiments, at least some of the transducers 220 may be used to selectively ablate portions of the tissue 222. For example, some of the transducers 220 may be used to ablate a pattern or path around various ones of the bodily openings, ports or pulmonary vein ostia, for instance to reduce or eliminate the occurrence of atrial fibrillation.

FIGS. 3A, 3B, 3C, 3D and 3E show a transducer-based device system (i.e., a portion thereof shown schematically) that includes a transducer-based device 300 according to one illustrated embodiment. Transducer-based device 300 includes a plurality of elongate members 304 (three called out in each of FIGS. 3A and 3B, and three are called out in each of FIGS. 3C, 3D and 3E as 304a, 304b and 304c) and a plurality of transducers 306 (three called out in FIG. 3A, three called out in FIG. 3B as 306a, 306b and 306c, and seven called out in each of FIGS. 3C and 3D, six of the seven identified as 306q, 306r, 306s, 306t, 306u and 306v). As will become apparent, the plurality of transducers 306 are positionable within a bodily cavity. For example, in some embodiments, the transducers 306 are able to be positioned in a bodily cavity by movement into, within, or into and within the bodily cavity, with or without a change in a configuration of the plurality of transducers 306. In some embodiments, the plurality of transducers 306 are arrangeable to form a two- or three-dimensional distribution, grid or array of the transducers capable of mapping, ablating or stimulating an inside surface of a bodily cavity or lumen without requiring mechanical scanning As shown for example, in FIG. 3A, the plurality of transducers 306 are arranged in a distribution receivable in a bodily cavity (not shown in FIG. 3A). As shown for example, in FIG. 3A, the plurality of transducers 306 are arranged in a distribution suitable for delivery to a bodily cavity (not shown in FIG. 3A). (It should also be noted, for example, that the expanded or deployed configuration (e.g., FIGS. 2, 3B-3G, 3I, and 3J) also provide transducers 306 arranged in a distribution receivable in a bodily cavity.)

The elongate members 304 are arranged in a frame or structure 308 that is selectively movable between an unexpanded or delivery configuration (i.e., as shown in FIG. 3A) and an expanded or deployed configuration (i.e., as shown in FIG. 3B) that may be used to position elongate members 304 against a tissue surface within the bodily cavity or position the elongate members 304 in the vicinity of or in contact with the tissue surface. In some embodiments, structure 308 has a size in the unexpanded or delivery configuration suitable for percutaneous delivery through a bodily opening (i.e., via catheter sheath 312, not shown in FIG. 3B) to the bodily cavity. In some embodiments, structure 308 has a size in the expanded or deployed configuration too large for percutaneous delivery through a bodily opening (i.e., via catheter sheath 312) to the bodily cavity. The elongate members 304 may form part of a flexible circuit structure (i.e., also known as a flexible printed circuit board (PCB) circuit). The elongate members 304 can include a plurality of different material layers, and each of the elongate members 304 can include a plurality of different material layers. The structure 308 can include a shape memory material, for instance Nitinol. The structure 308 can include a metallic material, for instance stainless steel, or non-metallic material, for instance polyimide, or both a metallic and non metallic material by way of non-limiting example. The incorporation of a specific material into structure 308 may be motivated by various factors including the specific requirements of each of the unexpanded or delivery configuration and expanded or deployed configuration, the required position or orientation (i.e., pose) or both of structure 308 in the bodily cavity, or the requirements for successful ablation of a desired pattern.

FIG. 4 is a schematic side elevation view of at least a portion of a transducer-based device 400 that includes a flexible circuit structure 401 that is employed to provide a plurality of transducers 406 (two called out) according to an example embodiment. In some embodiments, the flexible circuit structure 401 may form part of a structure (e.g., structure 308) that is selectively movable between a delivery configuration sized for percutaneous delivery and expanded or deployed configurations sized too large for percutaneous delivery. In some embodiments, the flexible circuit structure 401 may be located on, or form at least part of, of a structural component (e.g., elongate member 304) of a transducer-based device system.

The flexible circuit structure 401 can be formed by various techniques including flexible printed circuit techniques. In some embodiments, the flexible circuit structure 401 includes various layers including flexible layers 403a, 403b and 403c (i.e., collectively flexible layers 403). In some embodiments, each of flexible layers 403 includes an electrical insulator material (e.g., polyimide). One or more of the flexible layers 403 can include a different material than another of the flexible layers 403. In some embodiments, the flexible circuit structure 401 includes various electrically conductive layers 404a, 404b and 404c (collectively electrically conductive layers 404) that are interleaved with the flexible layers 403. In some embodiments, each of the electrically conductive layers 404 is patterned to form various electrically conductive elements. For example, electrically conductive layer 404a is patterned to form a respective electrode 415 of each of the transducers 406. Electrodes 415 have respective electrode edges 415-1 that form a periphery of an electrically conductive surface associated with the respective electrode 415. FIG. 3C shows another example of electrode edges 315-1 and illustrates that the electrode edges can define electrically-conductive-surface-peripheries of various shapes.

Returning to FIG. 4, electrically conductive layer 404b is patterned, in some embodiments, to form respective temperature sensors 408 for each of the transducers 406 as well as various leads 410a arranged to provide electrical energy to the temperature sensors 408. In some embodiments, each temperature sensor 408 includes a patterned resistive member 409 (two called out) having a predetermined electrical resistance. In some embodiments, each resistive member 409 includes a metal having relatively high electrical conductivity characteristics (e.g., copper). In some embodiments, electrically conductive layer 404c is patterned to provide portions of various leads 410b arranged to provide an electrical communication path to electrodes 415. In some embodiments, leads 410b are arranged to pass though vias (not shown) in flexible layers 403a and 403b to connect with electrodes 415. Although FIG. 4 shows flexible layer 403c as being a bottom-most layer, some embodiments may include one or more additional layers underneath flexible layer 403c, such as one or more structural layers, such as a steel or composite layer. These one or more structural layers, in some embodiments, are part of the flexible circuit structure 401 and can be part of, e.g., elongate member 304. In addition, although FIG. 4 shows only three flexible layers 403a-403c and only three electrically conductive layers 404a-404c, it should be noted that other numbers of flexible layers, other numbers of electrically conductive layers, or both, can be included.

In some embodiments, electrodes 415 are employed to selectively deliver RF energy to various tissue structures within a bodily cavity (not shown) (e.g., an intra-cardiac cavity). The energy delivered to the tissue structures may be sufficient for ablating portions of the tissue structures. The energy delivered to the tissue may be delivered to cause monopolar tissue ablation, bipolar tissue ablation or blended monopolar-bipolar tissue ablation by way of non-limiting example. In some embodiments, each electrode 415 is employed to sense an electrical potential in the tissue proximate the electrode 415. In some embodiments, each electrode 415 is employed in the generation of an intra-cardiac electrogram. In some embodiments, each resistive member 409 is positioned adjacent a respective one of the electrodes 415. In some embodiments, each of the resistive members 409 is positioned in a stacked or layered array with a respective one of the electrodes 415 to form a respective one of the transducers 406. In some embodiments, the resistive members 409 are connected in series to allow electrical current to pass through all of the resistive members 409. In some embodiments, leads 410a are arranged to allow for a sampling of electrical voltage in between each resistive members 409. This arrangement allows for the electrical resistance of each resistive member 409 to be accurately measured. The ability to accurately measure the electrical resistance of each resistive member 409 may be motivated by various reasons including determining temperature values at locations at least proximate the resistive member 409 based at least on changes in the resistance caused by convective cooling effects (e.g., as provided by blood flow). In some embodiments in which the transducer-based device is deployed in a bodily cavity (e.g., when the transducer-based device takes the form of a catheter device arranged to be percutaneously or intravascularly delivered to a bodily cavity), it may be desirable to perform various mapping procedures in the bodily cavity. For example, when the bodily cavity is an intra-cardiac cavity, a desired mapping procedure can include mapping electrophysiological activity in the intra-cardiac cavity. Other desired mapping procedures can include mapping of various anatomical features within a bodily cavity. An example of the mapping performed by devices according to various embodiments may include locating the position of the ports of various bodily openings positioned in fluid communication with a bodily cavity. For example, in some embodiments, it may be desired to determine the locations of various ones of the pulmonary veins or the mitral valve that each interrupts an interior surface of an intra-cardiac cavity such as a left atrium.

In some example embodiments, the mapping is based at least on locating bodily openings by differentiating between fluid and tissue (e.g., tissue defining a surface of a bodily cavity). There are many ways to differentiate tissue from a fluid such as blood or to differentiate tissue from a bodily opening in case a fluid is not present. Four approaches may include by way of non-limiting example:

1. The use of convective cooling of heated transducer elements by fluid. An arrangement of slightly heated transducers that is positioned adjacent to the tissue that forms the interior surface(s) of a bodily cavity and across the ports of the bodily cavity will be cooler at the areas which are spanning the ports carrying the flow of fluid.

2. The use of tissue impedance measurements. A set of transducers positioned adjacently to tissue that forms the interior surface(s) of a bodily cavity and across the ports of the bodily cavity can be responsive to electrical tissue impedance. Typically, heart tissue will have higher associated tissue impedance values than the impedance values associated with blood.

3. The use of the differing change in dielectric constant as a function of frequency between blood and tissue. A set of transducers positioned around the tissue that forms the interior surface(s) of the atrium and across the ports of the atrium monitors the ratio of the dielectric constant from 1 KHz to 100 KHz. Such can be used to determine which of those transducers are not proximate to tissue, which is indicative of the locations of the ports.

4. The use of transducers that sense force (i.e., force sensors). A set of force detection transducers positioned around the tissue that forms the interior surface(s) of a bodily cavity and across the bodily openings or ports of the bodily cavity can be used to determine which of the transducers are not engaged with the tissue, which may be indicative of the locations of the ports.

Referring to FIGS. 3A, 3B, transducer-based device 300 can communicate with, receive power from or be controlled by a transducer-activation system 322. In some embodiments, elongate members 304 can form a portion of an elongated cable 316 of control leads 317, for example by stacking multiple layers, and terminating at a connector 321 or other interface with transducer-activation system 322. The control leads 317 may correspond to the electrical connectors 216 in FIG. 2 in some embodiments. The transducer-activation device system 322 may include a controller 324 that includes a data processing device system 310 (e.g., from FIG. 1) and a memory device system 330 (e.g., from FIG. 1) that stores data and instructions that are executable by the data processing device system 310 to process information received from transducer-based device 300 or to control operation of transducer-based device 300, for example activating various selected transducers 306 to ablate tissue. Controller 324 may include one or more controllers.

Transducer-activation device system 322 includes an input-output device system 320 (e.g., an example of 120 from FIG. 1) communicatively connected to the data processing device system 310 (i.e., via controller 324 in some embodiments). Input-output device system 320 may include a user-activatable control that is responsive to a user action. Input-output device system 320 may include one or more user interfaces or input/output (I/O) devices, for example one or more display device systems 332, speaker device systems 334, keyboards, mice, joysticks, track pads, touch screens or other transducers to transfer information to, from, or both to and from a user, for example a care provider such as a physician or technician. For example, output from a mapping process may be displayed on a display device system 332.

Transducer-activation device system 322 may also include an energy source device system 340 including one or more energy source devices connected to transducers 306. In this regard, although FIG. 3A shows a communicative connection between the energy source device system 340 and the controller 324 (and its data processing device system 310), the energy source device system 340 may also be connected to the transducers 306 via a communicative connection that is independent of the communicative connection with the controller 324 (and its data processing device system 310). For example, the energy source device system 340 may receive control signals via the communicative connection with the controller 324 (and its data processing device system 310), and, in response to such control signals, deliver energy to, receive energy from, or both deliver energy to and receive energy from one or more of the transducers 306 via a communicative connection with such transducers 306 (e.g., via one or more communication lines through catheter body 314, elongated cable 316 or catheter sheath 312) that does not pass through the controller 324. In this regard, the energy source device system 340 may provide results of its delivering energy to, receiving energy from, or both delivering energy to and receiving energy from one or more of the transducers 306 to the controller 324 (and its data processing device system 310) via the communicative connection between the energy source device system 340 and the controller 324.

In any event, the number of energy source devices in the energy source device system 340 is fewer than the number of transducers in some embodiments. The energy source device system 340 may, for example, be connected to various selected transducers 306 to selectively provide energy in the form of electrical current or power (e.g., RF energy), light or low temperature fluid to the various selected transducers 306 to cause ablation of tissue. The energy source device system 340 may, for example, selectively provide energy in the form of electrical current to various selected transducers 306 and measure a temperature characteristic, an electrical characteristic, or both at a respective location at least proximate each of the various transducers 306. The energy source device system 340 may include as its energy source devices various electrical current sources or electrical power sources. In some embodiments, an indifferent electrode 326 is provided to receive at least a portion of the energy transmitted by at least some of the transducers 306. Consequently, although not shown in FIG. 3A, the indifferent electrode 326 may be communicatively connected to the energy source device system 340 via one or more communication lines in some embodiments. In addition, although shown separately in FIG. 3A, indifferent electrode 326 may be considered part of the energy source device system 340 in some embodiments.

It is understood that input-output device system 320 may include other systems. In some embodiments, input-output device system 320 may optionally include energy source device system 340, transducer-based device 300 or both energy source device system 340 and transducer-based device 300 by way of non-limiting example.

Structure 308 can be delivered and retrieved via a catheter member, for example a catheter sheath 312. In some embodiments, a structure provides expansion and contraction capabilities for a portion of a medical device (e.g., an arrangement, distribution or array of transducers 306). The transducers 306 can form part of, be positioned or located on, mounted or otherwise carried on the structure and the structure may be configurable to be appropriately sized to slide within catheter sheath 312 in order to be deployed percutaneously or intravascularly. FIG. 3A shows one embodiment of such a structure. In some embodiments, each of the elongate members 304 includes a respective distal end 305 (only one called out), a respective proximal end 307 (only one called out) and an intermediate portion 309 (only one called out) positioned between the proximal end 307 and the distal end 305. The respective intermediate portion 309 of each elongate member 304 includes a first or front surface 318a that is positionable to face an interior tissue surface within a bodily cavity (not shown) and a second or back surface 318b opposite across a thickness of the intermediate portion 309 from the front surface 318a. In various embodiments, the intermediate portion 309 of each of the elongate members 304 includes a respective pair of side edges of the front surface 318a, the back surface 318b, or both the front surface 318a and the back surface 318b, the side edges of each pair of side edges opposite to one another, the side edges of each pair of side edges extending between the proximal end 307 and the distal end 305 of the respective elongate member 304. In some embodiments, each pair of side edges includes a first side edge 327a (only one called out in FIG. 3A) and a second side edge 327b (only one called out in FIG. 3A). In some embodiments, each of the elongate members 304, including each respective intermediate portion 309, is arranged front surface 318a-toward-back surface 318b in a stacked array during an unexpanded or delivery configuration similar to that described in co-assigned International Application No.: PCT/US2012/022061 and co-assigned International Application No.: PCT/US2012/022062. In many cases a stacked array allows the structure 308 to have a suitable size for percutaneous or intravascular delivery. In some embodiments, the elongate members 304 are arranged to be introduced into a bodily cavity (again not shown in FIG. 3A) distal end 305 first. For clarity, not all of the elongate members 304 of structure 308 are shown in FIG. 3A. A flexible catheter body 314 is used to deliver structure 308 through catheter sheath 312. In some embodiments, each elongate member includes a twisted portion proximate at proximal end 307. Similar twisted portions are described in co-assigned International Application No.: PCT/US2012/022061 and co-assigned International Application No.: PCT/US2012/022062.

In a manner similar to that described in co-assigned International Application No.: PCT/US2012/022061 and co-assigned International Application No.: PCT/US2012/022062, each of the elongate members 304 is arranged in a fanned arrangement 370 in FIG. 3B. In some embodiments, the fanned arrangement 370 is formed during the expanded or deployed configuration in which structure 308 is manipulated to have a size too large for percutaneous or intravascular delivery. In some embodiments, structure 308 includes a proximal portion 308a having a first domed shape 309a and a distal portion 308b having a second domed shape 309b. In some embodiments, the proximal and the distal portions 308a, 308b include respective portions of elongate members 304. In some embodiments, the structure 308 is arranged to be delivered distal portion 308b first into a bodily cavity (again not shown) when the structure is in the unexpanded or delivery configuration as shown in FIG. 3A. In some embodiments, the proximal and the distal portions 308a, 308b are arranged in a clam shell configuration in the expanded or deployed configuration shown in FIG. 3B. In various example embodiments, each of the front surfaces 318a (three called out in FIG. 3B) of the intermediate portions 309 of the plurality of elongate members 304 face outwardly from the structure 308 when the structure 308 is in the deployed configuration. In various example embodiments, each of the front surfaces 318a of the intermediate portions 309 of the plurality of elongate members 304 are positioned adjacent an interior tissue surface of a bodily cavity (not shown) in which the structure 308 (i.e., in the deployed configuration) is located. In various example embodiments, each of the back surfaces 318b (two called out in FIG. 3B) of the intermediate portions 309 of the plurality of elongate members 304 face an inward direction when the structure 308 is in the deployed configuration.

The transducers 306 can be arranged in various distributions or arrangements in various embodiments. In some embodiments, various ones of the transducers 306 are spaced apart from one another in a spaced apart distribution in the delivery configuration shown in FIG. 3A. In some embodiments, various ones of the transducers 306 are arranged in a spaced apart distribution in the deployed configuration shown in FIG. 3B. In some embodiments, various pairs of transducers 306 are spaced apart with respect to one another. In some embodiments, various regions of space are located between various pairs of the transducers 306. For example, in FIG. 3B the transducer-based device 300 includes at least a first transducer 306a, a second transducer 306b and a third transducer 306c (all collectively referred to as transducers 306). In some embodiments each of the first, the second, and the third transducers 306a, 306b and 306c are adjacent transducers in the spaced apart distribution. In some embodiments, the first and the second transducers 306a, 306b are located on different elongate members 304 while the second and the third transducers 306b, 306c are located on a same elongate member 304. In some embodiments, a first region of space 350 is between the first and the second transducers 306a, 306b. In some embodiments, the first region of space 350 is not associated with any physical portion of structure 308. In some embodiments, a second region of space 360 associated with a physical portion of device 300 (i.e., a portion of an elongate member 304) is between the second and the third transducers 306b, 306c. In some embodiments, each of the first and the second regions of space 350, 360 does not include a transducer of transducer-based device 300. In some embodiments, each of the first and the second regions of space 350, 360 does not include any transducer. It is noted that other embodiments need not employ a group of elongate members 304 as employed in the illustrated embodiment. For example, other embodiments may employ a structure having one or more surfaces, at least a portion of the one or more surfaces defining one or more openings in the structure. In these embodiments, a region of space not associated with any physical portion of the structure may extend over at least part of an opening of the one or more openings In other example embodiments, other structures may be employed to support or carry transducers of a transducer-based device such as a transducer-based catheter. For example, an elongated catheter member may be used to distribute the transducers in a linear or curvilinear array. Basket catheters or balloon catheters may be used to distribute the transducers in a two-dimensional or three-dimensional array.

In various example embodiments, at least some of the plurality of transducers 306 include respective electrodes 315 (seven called out in each of FIGS. 3C, 3D, six of the seven called out as 315q, 315r, 315s, 315t, 315u and 315v), each electrode 315 including a respective energy transmission surface 319 (one called out in FIG. 3C, three called out in FIG. 3D, two of the three called out as 319u, 319v) configured for transferring energy to tissue, from tissue or both to and from tissue. In various embodiments, each of the energy transmission surfaces 319 is provided by an electrically conductive surface. In some embodiments, each of the electrodes 315 is solely located on a surface of an elongate member 304 (e.g., front surfaces 318a or back surfaces 318b). In some embodiments, various electrodes 315 are located on one, but not both of the respective front surface 318a and respective back surface 318b of each of various ones of the elongate members 304.

Various conventional percutaneous or intravascular transducer-based device systems employ, or have employed, relatively low numbers of transducers typically on the order of 64 or fewer transducers or a number of transducers arranged with a relatively low spatial distribution density (e.g., a relatively low number of transducers arranged per a given area). Various embodiments disclosed in this detailed description may employ distributions of transducers having relatively high spatial densities (e.g., a relatively high number of transducers arranged per a given region of space) than conventionally employed. Increased number of transducers or increased spatial densities of transducers within a particular distribution of the transducers may be motivated for various reasons. For example, increased numbers of transducers may allow for higher spatial densities in the distributions of the transducers to allow the transducers to interact with a tissue region of a bodily cavity with greater resolution and accuracy. The interactions may include ablation, temperature detection, impedance detection, electrophysiological activity detection and tissue stimulation by way of non-limiting example. In some case, distributions of transducers having relatively high spatial densities may provide enhanced diagnostic or treatment procedures performed on a given tissue region by allowing for the interaction of a greater number of transducers with the given tissue region. Various embodiments disclosed in this detailed description may employ 100 or more transducers, 200 or more transducers or even 300 or more transducers. Various transducer-based devices disclosed in this detailed description (e.g., as depicted at least in part in FIGS. 3A, 3B, 3C, 3D, 3E, 3F, 3G, 3H, 3I, 3J and 3K) are representative of various embodiments that employ several hundreds of transducers. Various transducer-based devices disclosed in this detailed description (e.g., as depicted at least in part in FIGS. 3A, 3B, 3C, 3D, 3E, 3F, 3G, 3H, 3I, 3J and 3K) are representative of various embodiments that employ distributions of transducers having relatively higher spatial densities. Although transducers 306, electrodes 315 or both transducers 306 and electrodes 315 are referenced with respect to various embodiments, it is understood that other transducers or transducer elements may be employed in other embodiments. It is understood that a reference to a particular transducer 306 in various embodiments may also imply a reference to an electrode 315, as an electrode 315 may be part of the transducer 306 as shown, e.g., with FIG. 4.

FIG. 3C is a perspective view of at least one embodiment of the transducer-based device 300 as viewed from a viewing angle that is different from that shown in FIG. 3B. For clarity of illustration, only structure 308 including various ones of the elongate members 304, and a portion of catheter body 314 are shown in FIG. 3C. In a manner similar to that shown in FIG. 3B, transducer-based device 300 is shown in the expanded or deployed configuration. In some embodiments, the respective intermediate portions 309 (only two called out) of various ones of the elongate members 304 are angularly arranged with respect to one another about a first axis 335a when structure 308 is in the deployed configuration. In various embodiments, the respective intermediate portions 309 of a respective pair of the elongate members 304 are angularly spaced with respect to one another by a respective angle radiating from a point on the first axis 335a when structure 308 is in the deployed configuration. The same may apply for each pair of adjacent elongate members 304 in some embodiments. In various embodiments, the intermediate portions 309 of various ones of the elongate members 304 are radially arranged about first axis 335a when structure 308 is in the deployed configuration. In various embodiments, the intermediate portions 309 of various ones of the elongate members 304 are circumferentially arranged about first axis 335a when structure 308 is in the deployed configuration, similar to lines of longitude about an axis of rotation of a body of revolution, which body of revolution may, or may not be spherical. Use of the word circumference in this detailed description, and derivatives thereof, such as circumferential, circumscribe, circumlocutory and other derivatives, refers to a boundary line of a shape, volume or object which may, or may not, be circular or spherical. In some embodiments, each of the elongate members 304 includes a curved portion 323 (only two called out) having a curvature configured to cause the curved portion 323 to extend along at least a portion of a curved path, the curvature configured to cause the curved path to intersect the first axis 335a at each of a respective at least two spaced apart locations along the first axis 335a when structure 308 is in the deployed configuration. In some embodiments, the curved path is defined to include an imagined extension of the curved portion along the curved portion's extension direction while maintaining the curved portion's curvature. In some embodiments, each curved portion 323 may extend entirely along, or at least part way along the respective curved path to physically intersect at least one of the respective at least two spaced apart locations along the first axis 335a. In some particular embodiments, no physical portion of a given elongate member of an employed structure intersects any of the at least two spaced apart locations along the first axis 335a intersected by the respective curved path associated with the curved portion 323 of the given elongate member. For example, the end portion of the given elongate member may be physically separated from the first axis 335a by hub system (not shown) employed to physically couple or align the elongate member to other elongate members. Additionally or alternatively, a given elongate member may include a recurve portion arranged to physically separate the given elongate member from the first axis 335a. In some embodiments, various ones of the elongate members 304 cross one another at a location on the structure 308 passed through by the first axis 335a when the structure 308 is in the deployed configuration. In various embodiments, the curved path is an arcuate path. In various embodiments, at least the portion of the curved path extended along by corresponding curved portion 323 is arcuate. As used herein, the word "curvature" should be understood to mean a measure or amount of curving. In some embodiments, the word "curvature" is associated with a rate of change of the angle through which the tangent to a curve turns in moving along the curve.

In some embodiments, the intermediate portion 309 of first elongate member 304a overlaps the intermediate portion 309 of a second elongate member 304b at a location on structure 308 passed through by first axis 335a when structure 308 is in the deployed configuration. In some embodiments, the intermediate portions 309 of the first elongate member 304a and the second elongate member 304b cross at a location on structure 308 passed through, or intersected, by first axis 335a when structure 308 is in the deployed configuration. In some embodiments, the intermediate portion 309 of first elongate member 304a is adjacent the intermediate portion 309 of the second elongate member 304b when structure 308 is in the deployed configuration. In various embodiments, the intermediate portions 309 of at least some of the plurality of elongate members 304 are, when the structure 309 is in the deployed configuration, sufficiently spaced from the first axis 335a to position each of at least some of the plurality of the electrodes 315 at respective locations suitable for contact with a tissue wall of the bodily cavity (not shown in FIG. 3C).

In various embodiments, at least some of the transducers 306 are radially spaced about first axis 335a when structure 308 is in the deployed configuration. For example, various ones of the electrodes 315 are radially spaced about first axis 335a in the deployed configuration in at least some of the embodiments associated with various ones of FIGS. 3B, 3C, 3D and 3E. In various embodiments, at least some of the transducers 306 are circumferentially arranged about first axis 335a when structure 308 is in the deployed configuration. For example, various ones of the electrodes 315 are circumferentially arranged about first axis 335a in the deployed configuration in at least some of the embodiments associated with various ones of FIGS. 3B, 3C, 3D and 3E. Various methods may be employed to describe the various spatial relationships of the transducers 306 or electrodes 315 or various sets of transducers 306 or sets of electrodes 315 employed according to various embodiments. For example, in FIGS. 3C and 3D the plurality of the electrodes 315 includes a first group 336a (not called out in FIG. 3E) of the electrodes 315 located on first elongate member 304a and a second group 338a (not called out in FIG. 3E) of the electrodes 315 located on second elongate member 304b. It is understood that although electrodes are referred to in these described embodiments, the same analysis applies to the corresponding transducers in some embodiments. It is understood that although groups of electrodes are referred to in these described embodiments, the plurality of electrodes 315 may form part of a plurality of sets of one or more of the electrodes 315, each respective set of the electrodes 315 located on a respective one of the elongate members 304 in other embodiments. The electrodes 315 of the first group 336a are arranged such that each electrode 315 of the first group 336a is intersected by a first plane 342a having no thickness. The phrase "no thickness" in this and similar contexts means no thickness, practically no thickness, or infinitely small thickness, and excludes perceptibly large thicknesses like thicknesses on the order of a size of an electrode 315. The electrodes 315 of the second group 338a are arranged such that each electrode 315 of the second group 338a is intersected by a second plane 344a having no thickness. For clarity, the intersection of each electrode 315 of the first group 336a by first plane 342a is represented in FIG. 3C by intersection line 345a. For clarity, the intersection of each electrode 315 of the second group 338a by second plane 344a is represented in FIG. 3C by intersection line 345b. First plane 342a and second plane 344a are depicted as having boundaries merely for purposes of clarity of illustration in FIG. 3C.

Each of the first plane 342a and the second plane 344a are non-parallel planes that intersect each other along a second axis 337a. In some embodiments, second axis 337a is parallel to first axis 335a. In some embodiments, first axis 335a and second axis 337a are collinear. In some embodiments, the first axis 335a and the second axis 337a form a single axis. In other embodiments, different spatial relationships may exist between first axis 335a and second axis 337a. In some embodiments, the electrodes 315 are arranged in a spatial distribution in which a first electrode 315q associated with transducer 306q is intersected by each of the first plane 342a and the second plane 344a when the structure 308 is in the deployed configuration. In some embodiments, first electrode 315q is not intersected by first axis 335a when structure 308 is in the deployed configuration. In some embodiments, first electrode 315q is not intersected by second axis 337a when structure 308 is in the deployed configuration. In some embodiments, the first group 336a of electrodes 315 includes first electrode 315q. In some embodiments, the second group of electrodes 338a does not include first electrode 315q. In various embodiments, the first axis 335a, the second axis 337a or each of the first axis 335a and the second axis 337a intersects at least one electrode 315 located on structure 308 (e.g., electrode 315r associated with transducer 306r in FIGS. 3C and 3D) that does not include first electrode 315q. In some embodiments, the first axis 335a, the second axis 337a or each of the first axis 335a and the second axis 337a does not intersect any electrode 315 located on structure 308, such as, for example, when no polar electrode (e.g., 315r in FIGS. 3C and 3D) is provided. In some embodiments, the first axis 335a, the second axis 337a or each of the first axis 335a and the second axis 337a does not intersect any electrode or transducer.

FIG. 3D is a plan view of structure 308 in the deployed configuration of FIG. 3C. The plan view of FIG. 3D has an orientation such that each of first plane 342a and second plane 344a is viewed 'on edge' to their respective planar surfaces. (Note that in embodiments where each of the first plane 342a and the second plane 344a have no thickness, 'on edge' is intended to refer to an 'on edge' perspective assuming that each plane had an edge of minimal thickness.) The plan view of FIG. 3D has an orientation such that each of the first axis 335a and second axis 337a is viewed along the axis in this particular embodiment. Each of first plane 342a and second plane 344a are represented by a respective "heavier" line in FIG. 3D. Each of first axis 335a and second axis 337a are represented by a "•" symbol in FIG. 3D. It is understood that each of the depicted lines or symbols "•" used to represent any corresponding plane, intersection line or axis in this disclosure do not impart any size attributes on the corresponding plane or axis.

In various embodiments, each of the first group 336a and the second group 338a includes two or more of the electrodes 315. In some embodiments, the first group 336a, the second group 338a or each of both the first group 336a and the second group 338a includes three or more of the electrodes 315. In various embodiments, the first group 336a, the second group 338a or each of both the first group 336a and the second group 338a includes a pair of adjacent electrodes 315 located on a respective one of the first elongate member 304a and the second elongate member 304b. In some of these various embodiments, a region of space associated with a physical portion of structure 308 (e.g., an elongate member 304 portion) is located between the respective electrodes 315 of the pair of adjacent electrodes 315 included in the first group 336a, and the region of space is intersected by the first plane 342a when the structure 308 is in the deployed configuration. In some embodiments, the respective electrodes 315 of the first group 336a are spaced along a length of a portion of the first elongate member 304a, the length extending between the respective distal and proximal ends 305, 307 (not called out in FIGS. 3B, 3C, 3D and 3E) of the first elongate member 304a, the entirety of the length of the portion of the first elongate member 304a being intersected by the first plane 342a when structure 308 is in the deployed configuration. In some embodiments, the first plane 342a intersects every electrode 315 located on the first elongate member 304a when structure 308 is in the deployed configuration. In some embodiments, the second plane 344a intersects every electrode 315 that is located on the second elongate member 304b when structure 308 is in the deployed configuration. In some embodiments, some, but not all of the respective electrodes 315 located on the first elongate member 304a, the second elongate member 304b, or each of the first elongate member 304a and the second elongate member 304b are intersected by a corresponding one of the first plane 342a and the second plane 344a when structure 308 is in the deployed configuration.

In some embodiments, the second axis 337a is not collinear with the first axis 335a. In some embodiments, the second axis 337a and the first axis 335a do not form a single axis. In some embodiments, the second axis 337a does not intersect the first axis 335a. FIG. 3D shows another embodiment in which each electrode 315 of second group 338b (not called out in FIGS. 3C and 3E) of electrodes 315 located on second elongate member 304b is intersected by a second plane 344b having no thickness. Second plane 344b is viewed transversely to its planar surface in FIG. 3D and is represented by a line. Although second plane 344b is depicted parallel to second plane 344a in FIG. 3D, different orientations may be employed in other embodiments. First plane 342a and second plane 344b are non parallel planes that intersect one another along a second axis 337b represented by a symbol "•" in FIG. 3D. For clarity, each of second plane 344b and second axis 337b is not shown in FIG. 3C. In at least one particular embodiment associated with FIG. 3D, each of the first plane 342a and the second plane 344b intersects a first electrode 315s associated with transducer 306s that is not intersected by the second axis 337b. In at least one particular embodiment associated with FIG. 3D, first electrode 315s is not intersected by the first axis 335a. In at least one particular embodiment associated with FIG. 3D, first electrode 315s is not intersected by the second axis 337b. In at least one particular embodiment associated with FIG. 3D, second axis 337b intersects at least one other electrode (e.g., electrode 315t associated with transducer 306t). In at least one particular embodiment associated with FIG. 3D, the intermediate portion 309 of the first elongate member 304a overlaps the intermediate portion 309 of the second elongate member 304b at each of a first location on structure 308 passed through by first axis 335a and a second location on structure 308 passed through by the second axis 337b when structure 308 is in the deployed configuration, the second and first locations being different locations.

In various embodiments, particular spatial distributions of electrodes or transducers similar to the ones employed in FIGS. 3A, 3B, 3C, 3D and 3E may advantageously allow for higher spatial densities of the electrodes or transducers to be employed. For example, as best seen in FIGS. 3C and 3D, various distributions of electrodes 315 having relatively high spatial densities are created throughout a significant portion of structure 308 including various regions proximate first axis 335a. It is noted that portions of various ones of elongate members 304 shown in FIGS. 3C and 3D overlap one another as the portions approach first axis 335a when structure 308 is in the deployed configuration. In various embodiments, overlapping elongate members 304 may be employed at least in part to provide to distributions of the electrodes 315 having higher spatial densities. In FIGS. 3C and 3D, a portion of a first elongate member 304 (e.g., elongate member 304a) is shown overlapping a portion of at least a second elongate member 304 (e.g., elongate member 304b) when structure 308 is in the deployed configuration. FIG. 3E includes an enlarged view of a portion of the structure 308 depicted in FIG. 3D, the portion of structure 308 including portions of at least elongate members 304a and 304b. For clarity of illustration, planes 342a, 344a, 344b and axis 337b are not shown in FIG. 3E. In at least one particular embodiment associated with FIG. 3E, a portion 346a (i.e., only called out in FIG. 3E) of the front surface of 318a of first elongate member 304a overlaps a portion 347a (i.e., only called out in FIG. 3E, partially bounded by a ghosted line 345a for clarity) of the front surface 318a of second elongate member 304b as viewed normally to the portion 346a of the front surface 318a of first elongate member 304a when structure 308 is in the deployed configuration. In this particular embodiment, the spatial density of the distribution of transducers 306/electrodes 315 is such that at least a first electrode (e.g., electrode 315q associated with transducer 306q) is located at least on the portion 346a of the front surface 318a of first elongate member 304a. In some embodiments, the portion of 347a of the front surface 318a of second elongate member 304b faces the back surface 318b (not called out in FIG. 3E) of first elongate member 304a when structure 308 is in the deployed configuration. In some embodiments, the portion of 347a of the front surface 318a of second elongate member 304b faces the back surface 318b of first elongate member 304a when structure 308 is in the delivery configuration (e.g., when the elongate members 304 are arranged front surface-toward-back surface in a stacked array (e.g., when the structure 308 is in a delivery configuration similar to that depicted in FIG. 3A). In some example embodiments, the portion 347a of the front surface 318a of second elongate member 304b contacts the back surface 318b of first elongate member 304a when structure 308 is in the deployed configuration. In a similar manner, a portion 346b (i.e., only called out in FIG. 3E) of the front surface of 318a of elongate member 304b overlaps a portion 347b (i.e., only called out in FIG. 3E, partially bounded by a ghosted line 345b for clarity) of the front surface 318a of elongate member 304c as viewed normally to the portion 346b of the front surface 318a of elongate member 304b when structure 308 is in the deployed configuration. In this case, a first electrode (e.g., electrode 316u associated with transducer 306u) is located at least on the portion 346b of the front surface 318a of elongate member 304b.

Other spatial characteristics are associated with the distribution of transducers 306/electrodes 315 associated with various embodiments associated with FIGS. 3A, 3B, 3C, 3D and 3E. For example, as best seen in FIG. 3E, a first side edge 327a of the first elongate member 304a crosses a first side edge 327a of the pair of side edges of the second elongate member 304b at a first location 351a and crosses a second side edge 327b of the pair of side edges of the second elongate member 304b at a second location 352a when structure 308 is in the deployed configuration. In various embodiments associated with FIG. 3E, various electrodes 315 are located at least on a portion 348a of the second elongate member 304b, the portion 348a of the second elongate member 304b located between a first transverse line 349a and a second transverse line 349b (e.g., each depicted by a ghosted line in FIG. 3E) when the structure 308 is in the deployed configuration. In various embodiments associated with FIG. 3E, the first transverse line 349a extends across a first width 353a of the second elongate member 304b at the first location 351a, and the second transverse line 349b extends across a second width 353b of the second elongate member 304b at the second location 352a. In at least one particular embodiment associated with FIG. 3E, the first width 353a and the second width 353b are the widths of the front surfaces 318a of the second elongate member 304b. In at least one particular embodiment associated with FIG. 3E, a magnitude of first width 353a is substantially the same as a magnitude of the second width 353b. In some embodiments, the magnitude of the first width 353a is different than the magnitude of the second width 353b. In some embodiments, the first transverse line 349a is perpendicular to one or both of the side edges 327a, 327b of the second elongate member 304b. Similarly, in some embodiments, the second transverse line 349b is perpendicular to one or both of the side edges 327a, 327b of the second elongate member 304b. In some embodiments, the magnitude of the first width 353a is a minimum with respect to all other respective magnitudes of possible widths between side edges 327a, 327b of the second elongate member 304b originating at location 351a. Similarly, in some embodiments, the magnitude of the second width 353b is a minimum with respect to all other respective magnitudes of possible widths between side edges 327a, 327b of the second elongate member 304b originating at location 352a.

In some example embodiments, one or more of the electrodes 315 are wholly located on the portion 348a of the second elongate member 304b when the structure 308 is in the deployed configuration. For example, electrode 315u is wholly located on the portion 348a (which is rectangular in some embodiments such as FIG. 3E) of the second elongate member 304b when the structure 308 is in the deployed configuration. In some example embodiments, at least a portion of an electrode 315 of the plurality of electrodes 315 is located on the portion 348a of the second elongate member 304b when structure 308 is in the deployed configuration. As shown, for example, in FIG. 3E, electrode 315v is located at least on portion 348a in the deployed configuration. In various other embodiments, two or more of the electrodes 315 may be located on the portion 348a of the second elongate member 304b.

It may be noted that distances between adjacent ones of the elongate members 304 shown in FIGS. 3C, 3D and 3E vary as elongate members 304 extend towards first axis 335a when structure 308 is in the deployed configuration. In some cases, the varying distances between adjacent elongate members 304 in the deployed configuration may give rise to shape, size or dimensional constraints for the electrodes 315 located on the elongate members 304. In some cases, the overlapping portions of various ones the elongate members 304 in the deployed configuration may give rise to shape, size or dimensional constraints for the electrodes 315 located on the portions of the various ones of the elongate members 304. For example, it may be desirable to reduce a surface area of an electrode adjacent an overlap region on an overlapped elongate member to accommodate the reduced-exposed-surface area of the overlapped elongate member in the region adjacent the overlap region (e.g., electrode 315u in FIG. 3E).

In various embodiments, the respective shape of various electrically conductive surfaces (e.g., energy transmission surfaces 319) of various ones of the electrodes 315 vary among the electrodes 315. In various embodiments, the respective shape of various electrically conductive surfaces (e.g., energy transmission surfaces 319) of various ones of the electrodes 315 vary among the electrodes 315 in accordance with their proximity to first axis 335a. In various embodiments, one or more dimensions or sizes of various electrically conductive surfaces (e.g., energy transmission surfaces 319) of various ones of the electrodes 315 vary among the electrodes 315. In various embodiments, one or more dimensional sizes of various electrically conductive surfaces (e.g., energy transmission surfaces 319) of various ones of the electrodes 315 vary in accordance with their proximity to first axis 335a. The shape or size variances associated with various ones of the electrodes 315 may be motivated for various reasons. For example, in various embodiments, the shapes or sizes of various ones of the electrodes 315 may be controlled in response to various ones of the aforementioned size or dimensional constraints.

Referring to FIG. 3E, it is noted that each of various ones of the electrodes 315 (e.g., electrodes 315*u* and 315*v*) located at least on second elongate member 304*b* have various electrode edges (e.g., 315-1 in FIG. 3C or 415-1 in FIG. 4) that form a periphery of an electrically conductive surface associated with each of the various electrodes 315 (e.g., an energy transmission surface 319). In at least one particular embodiment associated with FIG. 3E, a first electrode edge 333*a* associated with electrode 315*u* is arranged to follow a portion of the first side edge 327*a* of the first elongate member 304*a* between the first location 351*a* and the second location 352*a* when the structure 308 is an expanded or deployed configuration. In some embodiments, the first electrode edge 333*a* of electrode 315*u* is arranged to be parallel to the portion of the first side edge 327*a* of the first elongate member 304 between the first location 351 and the second location 352 when the structure 308 is in an expanded or deployed configuration. In this particular embodiment, a second electrode edge 333*b* forming part of the periphery of electrically conductive surface associated with electrode 315*u* is positioned opposite across the electrically conductive surface from the first electrode edge 333*a*. In this particular embodiment, the second electrode edge 333*b* is arranged to follow a portion of one of the side edges 327 of the second elongate member 304*b* (e.g., side edge 327*a* of second elongate member 304*b*). In this particular embodiment, the second electrode edge 333*b* is substantially parallel to the side edge 327*a* of second elongate member 304*b*.

FIGS. 3F and 3G respectively show perspective and plan views of a plurality of transducers and electrodes located on a structure 313 (e.g., in a deployed configuration) according to various embodiments. In various embodiments, structure 313 is selectively moveable from a delivery configuration to a deployed configuration in a manner similar to structure 308. It is noted that structure 313 is depicted in FIGS. 3F and 3G in a similar fashion to depictions of structure 308 in FIGS. 3C and 3D. In some embodiments, distributions of transducers or electrodes similar to those employed by structure 313 are employed by the structure 308 of FIGS. 3A, 3B, 3C, 3D and 3E. For the convenience of discussion, various elements associated with structure 313 will be identified by the respective part numbers of the corresponding elements associated with structure 308. For example, in reference to FIGS. 3F and 3G and other associated Figures, transducers are referred to as transducers 306, electrodes are referred to as electrodes 315, energy transmission surfaces are referred to as energy transmission surfaces 319, elongate members are referred to as elongate members 304, et cetera. It is noted that these elements disclosed in FIGS. 3F and 3G and other associated Figures are not limited to the embodiments of corresponding elements disclosed in FIGS. 3A, 3B, 3C, 3D and 3E. In some embodiments, structure 313 may assume a delivery configuration similar to that shown for structure 308 in FIG. 3A.

It may be noted that although the distributions of transducers 306/electrodes 315 associated with structure 313 have differences from the distribution of transducers 306/electrodes 315 associated with structure 308, there are also similarities. The respective intermediate portions 309 of various ones of the elongate members 304 (five called out in each of FIGS. 3F and 3G, four of the five called out as 304*d*, 304*e*, 304*f* and 304*g*) are angularly spaced with respect to one another about a first axis 335*b* when structure 313 is in the deployed configuration in a manner similar to that previously described with respect to structure 308. Various ones of the elongate members 304 cross one another at a location on the structure 313 passed through by first axis 335*b* when the structure 313 is in the deployed configuration. In at least one particular embodiment associated with FIGS. 3F, 3G, the intermediate portion 309 of a first elongate member (e.g., elongate member 304*d*) overlaps the intermediate portion 309 of a second elongate member (e.g., elongate member 304*e*) at a location on structure 313 passed through by first axis 335*b* when structure 313 is in the deployed configuration. In at least one particular embodiment associated with FIGS. 3F, 3G, the intermediate portion 309 of first elongate member 304*d* is adjacent the intermediate portion 309 of the second elongate member 304*e* when structure 313 is in the deployed configuration. The transducers 306 (nine called out in each of FIGS. 3F and 3G, eight of the nine called as transducers 306*w*, 306*x*, 306*y*, 306*z*, 306*aa*, 306*bb*, 306*cc*, and 306*dd*) and electrodes 315 (nine called out in each of FIGS. 3F and 3G, eight of the nine called out as electrodes 315*w*, 315*x*, 315*y*, 315*z*, 315*aa*, 315*bb*, 315*cc* and 315*dd*) are radially spaced about first axis 335*b* when structure 313 is in the deployed configuration in a manner similar to the embodiments associated with structure 308. The plurality of electrodes 315 located on structure 313 includes a first group 336*b* (not called out in FIGS. 3H, 3I) of the electrodes 315 located on first elongate member 304*d* and a second group 338*c* (not called out in FIGS. 3H, 3I) of the electrodes 315 located on second elongate member 304*e*. It is understood that although electrodes are herein described, other forms of transducers or transducer elements may be employed in other embodiments. The electrodes 315 of the first group 336*b* are arranged such that each electrode 315 of the first group 336*b* is intersected by a first plane 342*b* having no thickness. The electrodes 315 of the second group 338*c* are arranged such that each electrode 315 of the second group 338*c* is intersected by a second plane 344*c* having no thickness. For clarity, the intersection of each electrode 315 of the first group 336*b* by first plane 342*b* is represented in FIG. 3F by intersection line 345*c*. For clarity, the intersection of each electrode 315 of the second group 338*c* by second plane 344*c* is represented in FIG. 3F by intersection line 345*d*. First plane 342*b* and second plane 344*c* are depicted as having boundaries for clarity of illustration in FIG. 3F.

Each of the first plane 342*b* and the second plane 344*c* are non-parallel planes that intersect each other along a second axis 337*c* (represented by a symbol "•" in FIG. 3G). In some embodiments, second axis 337*c* is parallel to first axis 335*b*. In some embodiments, first axis 335*b* and second axis 337*c* are collinear. In some embodiments, the first axis 335*b* and the second axis 337*c* form a single axis. In some embodiments, the electrodes 315 are arranged in a spatial distribution in which a first electrode 315 (e.g., electrode 315*w* associated with transducer 306*w*) is intersected by each of the first plane 342*b* and the second plane 344*c* when the structure 313 is in the deployed configuration. In at least one particular embodiment, first electrode 315*w* is not intersected by first axis 335*b* when structure 313 is in the deployed configuration. In at least one particular embodiment, first electrode 315*w* is not intersected by second axis 337*c* when structure 313 is in the deployed configuration. In at least one particular embodiment, the first group 336*b* of electrodes 315 includes first electrode 315*w*. In at least one particular embodiment, the second group of electrodes 338*c* does not include first electrode 315*w*. In various embodiments, the first axis 335*a*, the second axis 337*c* or each of the first axis 335 and the second axis 337c intersects at least one other electrode 315 located on structure 313 (e.g., electrode 315x associated with transducer 306x in FIGS. 3F, 3G and 3I). In some embodiments, the first axis 335b, the second axis 337c or each of the first axis 335b and the second axis 337c do not intersect any electrode 315 located on structure 313.

In some embodiments, the second axis 337c is not collinear with the first axis 335b. In some embodiments, the second axis 337c and the first axis 335b do not form a single axis. In some embodiments, the second axis 337c does not intersect the first axis 335b. FIG. 3G shows another embodiment in which each electrode 315 of second group 338d (not called out in FIG. 3F, 3H and 3I) of electrodes 315 located on a second elongate member 304f is intersected by a second plane 344d having no thickness when structure 313 is in a deployed configuration. Second plane 344d is viewed transversely to its planar surface in FIG. 3G and is represented by a line. For clarity, second plane 344d is not shown in FIG. 3F. First plane 342b and second plane 344d are non parallel planes that intersect one another along a second axis 337d represented by a symbol "•" in FIG. 3G. In at least one particular embodiment, each of the first plane 342b and the second plane 344d intersects a first electrode 315y associated with transducer 306y when structure 313 is in a deployed configuration. In at least one particular embodiment, first electrode 315y is not intersected by the first axis 335b when structure 313 is in a deployed configuration. In at least one particular embodiment, first electrode 315y is not intersected by the second axis 337d when structure 313 is in a deployed configuration. In at least one particular embodiment, second axis 337d intersects at least one other electrode (e.g., electrode 315z associated with transducer 306z) when structure 313 is in a deployed configuration.

Embodiments associated with FIGS. 3F and 3G have spatial distributions of the transducers 306/electrodes 315 that have relatively high spatial densities in various regions of structure 313 including a plurality of regions proximate first axis 335b. In various embodiments, a spatial distribution of the transducers 306/electrodes 315 in various regions proximate first axis 335b have higher spatial densities than similar distributions associated with various embodiments of FIGS. 3A, 3B, 3C, 3D and 3E. Embodiments associated with FIGS. 3F and 3G may provide for electrodes 315 having electrically conductive surfaces (e.g., energy transmission surfaces 319, three called out in each of FIGS. 3F and 3G, two of the three called out as 319c and 319d) of greater size or dimension than some of the electrodes 315 associated with various embodiments of FIGS. 3A, 3B, 3C, 3D and 3E. In particular, larger electrodes 315 may be provided in regions proximate first axis 335b in at least some of the embodiments associated with FIGS. 3F and 3G. The use of larger electrodes (e.g., larger electrically conductive surfaces such as energy transmission surfaces 319c and 319d) may be motivated for various reasons. For example, in some tissue ablation applications, tissue ablation depths may be dependent on the size of the electrodes 315 employed for the ablation, with a use of larger electrodes 315 typically reaching a particular ablation depth in a shorter activation time than a use of relatively smaller electrodes 315. In some tissue ablation applications, deeper tissue ablation depths may be associated with larger electrodes.

FIG. 3H is shows perspective views of each of first elongate member 304d and second elongate member 304e in a "flattened" configuration in which the curved form of these elongate members 304 in FIGS. 3F and 3G is flattened out. It is noted that in embodiments where the elongate members 304 in FIGS. 3F and 3G include a twisted portion similar to the twisted portions of various ones of the elongate members 304 associated with FIGS. 3A, 3B, 3C, 3D and 3E, the twisted portions are shown untwisted in the flattened configuration of FIG. 3H. The flattened configuration is presented for clarity of illustration and it is understood that in the deployed configuration, FIGS. 3F and 3G are better representative of the forms of various ones of the elongate members at least in the deployed configuration. In a manner similar to the elongate members 304 of structure 308, the intermediate portion 309 of each of the elongate members 304d, 304e includes a front surface 318a and back surface 318b opposite across a thickness 318c of the elongate member. In some embodiments, at least some of the transducers 306/electrodes 315 are located on the front surfaces 318a. Each intermediate portion 309 includes a respective pair of side edges 327a, 327b. In various embodiments, the side edges 327a, 327b of each intermediate portion 309 are respective side edges of the front surface 318a, the back surface 318b, or both the front surface 318a and the back surface 318b of the intermediate portion 309. Each of the pair of side edges 327a, 327b extends between the proximal end 307 and the distal end 305 of the elongate member 304.

In some embodiments associated with FIGS. 3F and 3G, various ones of elongate members overlap one another when structure 313 is in the deployed configuration. In various embodiments, overlapping elongate members 304 may be employed at least in part to provide to distributions of the electrodes 315 having higher spatial densities. FIG. 3I includes an enlarged view of a portion of the structure 313 depicted in FIG. 3G, the portion of structure 313 including portions of at least elongate members 304d and 304e. For clarity of illustration, planes 342b, 344c, 344d and axis 337d are not shown in FIG. 3I.

In at least one particular embodiment, various portions of the front surface 318a of the first elongate member 304d overlap various portions of the front surface 318a of each of several ones of the plurality of elongate members 304 when structure 313 is in the deployed configuration. In at least one particular embodiment, various portions of the front surface 318a of the first elongate member 304d overlap various portions of the front surface 318a of every other one of the plurality of elongate members 304 when structure 313 is in the deployed configuration. In at least one particular embodiment associated with FIG. 3I, a portion 346c (i.e., only called out in FIG. 3I) of the front surface of 318a of a first elongate member 304 (e.g., elongate member 304d) overlaps a portion 347c (i.e., only called out in FIG. 3I, partially bounded by a ghosted line 345c) of the front surface 318a of at least a second elongate member (e.g., elongate member 304e) as viewed normally to the portion 346a of the front surface 318a of first elongate member 304a when structure 313 is in the deployed configuration. In at least one particular embodiment, the spatial density of the distribution of transducers 306/electrodes 315 is such that at least a first electrode (e.g., first electrode 315w associated with transducer 306w) is located at least on the portion 346c of the front surface 318a of first elongate member 304d. In at least one particular embodiment, the portion of 347c of the front surface 318a of second elongate member 304e faces the back surface 318b (not called out in FIG. 3I) of first elongate member 304d when structure 313 is in the deployed configuration. In some embodiments, the portion of 347c of the front surface 318a of second elongate member 304e faces the back surface 318b of first elongate member 304d when structure 313 is in the delivery configuration (e.g., when the elongate members 304 are arranged front surface-towardback surface in a stacked array when the structure 313 is in a delivery configuration similar to that depicted in FIG. 3A). In some example embodiments, the portion of 347c of the front surface 318a of second elongate member 304e contacts the back surface 318b of first elongate member 304d when structure 313 is in the deployed configuration.

In FIGS. 3F, 3G and 3I, the first elongate member 304d is positioned such that first edge 327a of the first elongate member 304d crosses at least a second edge of the second elongate member 304e (e.g., second edge 327b of second elongate member 304e) when structure 313 is in the deployed configuration. In some of the embodiments associated with FIG. 3F, 3G, 3H and 3I a portion of the first edge 327a of the first elongate member 304d forms a recessed portion 328a of first elongate member 304d that exposes at least a portion of a second transducer 306aa (e.g., second electrode 315aa in at least one particular embodiment) located on second elongate member 304e. All recessed portions such as recessed portion 328a described herein are collectively referred to as recessed portions 328. In at least some of the embodiments associated with FIGS. 3F, 3G, 3H and 3I, the exposed portion of second transducer 306aa (e.g., electrode 315aa) is located at least on portion of a surface (e.g., front surface 318a) of the second elongate member 304e as viewed normally to the portion of the surface of the second elongate member 304e when structure 313 is in the deployed configuration. In at least some of the embodiments associated with FIGS. 3F, 3G, 3H and 3I, recessed portion 328a of first elongate member 304d exposes at least a portion of second electrode 315aa as viewed normally to a surface of the exposed portion of second electrode 315aa. In at least some of the example embodiments associated with FIGS. 3F, 3G, 3H and 3I, the exposed portion of second transducer 306aa (e.g., electrode 315aa) is located on the second elongate member 304e as viewed towards the second transducer 306aa along a direction parallel to a direction that the first axis 335b extends along when structure 313 is in the deployed configuration. In some embodiments, the second group 338c includes second transducer 306aa (e.g., electrode 315aa). As best shown in FIGS. 3G and 3I, in some embodiments, the second transducer 306aa (e.g., electrode 315aa) is adjacent first transducer 306w (e.g., electrode 315w) when structure 313 is in the deployed configuration. In various embodiments associated with FIGS. 3F, 3G, 3H and 3I, at least some of the plurality of transducers 306/electrodes 315 are arranged in a plurality of concentric ringed arrangements 329 (four called out in FIG. 3G (one of which is shown by a ghosted line), two of the four called out as 329a, 329b) about the first axis 335b when structure 313 is in the deployed configuration, a first one of the ringed arrangements 329 (e.g., ringed arrangement 329a) having a fewer number of the transducers 306 (e.g., electrodes 315) than a second one of the ringed arrangements (e.g., ringed arrangement 329b). In some of these various example embodiments, the first ringed arrangement includes first transducer 306w (e.g., electrode 315w). In some of these various embodiments, the first ringed arrangement 329a does not include any of the transducers 306 (e.g., electrodes 315) located on the second elongate member 304e. In some of these example embodiments, the second ringed arrangement 329b includes the second transducer 306aa. In some of these various embodiments, the first ringed arrangement 329a is adjacent the second ringed arrangement 329b.

In various embodiments, first elongate member 304d includes a second recessed portion 328b (called out in FIGS. 3F, 3G and 3H) arranged to expose a portion of at least one transducer (e.g., electrode 315bb associated with transducer 306bb) located on second elongate member 304e when structure 313 is in the deployed configuration. In various embodiments, second elongate member 304e includes several recessed portions (e.g., recessed portions 328c and 328d called out in FIGS. 3H, 3J. In at least one particular embodiment, each of the recessed portions 328c and 328d has different dimensions or sizes than each of recessed portions 328a and 328b. Differences in the dimensions or sizes of various ones of the recessed portions 328 (e.g., any of recessed portions 328a, 328b, 328c, 328d and other described recessed portions) may be motivated by various reasons including the location of their corresponding elongate member 304 in structure 313 or a spatial relationship between various ones of the transducers 306/electrodes 315 in the deployed configuration. In some embodiments, the differences in the sizes or dimensions of various ones of the recessed portions 328 may be employed to create distribution of transducers 306/electrodes 315 having higher spatial densities. In various embodiments, each recessed portion 328c, 328d is arranged to expose a portion of at least one transducer 306 (e.g., electrode 315cc associated with transducer 306cc and electrode 315dd associated with transducer 306dd) located on elongate member 304g when structure 313 is in the deployed configuration. This is best shown in FIG. 3J which shows a plan view of structure 313 in the deployed configuration similar to that shown in FIG. 3G with the exception that elongate member 304d is not shown. It is understood that elongate member 304d is not shown in FIG. 3J only to better show elongate member 304e and its associated recessed portions 328c and 328d. For clarity of illustration, planes 342b, 344c, 344d and axes 335b, 337c, 337d are not shown in FIG. 3J.

In various embodiments associated with FIG. 3J, a first side edge 327a of a first elongate member (e.g., elongate member 304e) crosses a first side edge 327a of the pair of side edges of a second elongate member (e.g., elongate member 304g) at a first location 351b and crosses a second side edge 327b of the pair of side edges of the second elongate member 304g at a second location 352b when structure 313 is in the deployed configuration. In various embodiments associated with FIG. 3J, various electrodes 315 are located at least on a portion 348b of the second elongate member 304g, the portion 348b of the second elongate member 304g located between a first transverse line 349c and a second transverse line 349d (e.g., each depicted by a ghosted line in FIG. 3J) when the structure 313 is in the deployed configuration. In various embodiments associated with FIG. 3J, the first transverse line 349c extends across a first width 353c of the second elongate member 304g at the first location 351b and the second transverse line 349d extends across a second width 353d of the second elongate member 304g at the second location 352b. In at least one particular embodiment associated with FIG. 3J, the first width 353c and the second width 353d are the widths of the front surfaces 318a of the second elongate member 304g. In at least one particular embodiment associated with FIG. 3J, a magnitude of first width 353c is substantially the same as a magnitude of the second width 353d. In some embodiments, a magnitude of the first width 353c is different than a magnitude of the second width 353d. In at least one particular embodiment associated with FIG. 3J, each of electrodes 315cc associated with transducer 306cc and electrode 315dd associated with transducer 306dd is wholly located on the portion 348b of the second elongate member 304g when the structure 313 is in the deployed configuration. In at least one particular embodiment associated with FIG. 3J, electrode 315*ee* associated with transducer 306*ee* is located at least on portion 348*b* in the deployed configuration. Similar arrangements exist between other sets of the elongate members 304 of structure 313 in the deployed configuration. For example, referring to FIG. 3I, a first elongate member (e.g., elongate member 304*d*) is positioned such that its first edge 327*a* crosses a first side edge 327*a* of a second elongate member (elongate member 304*e*) at a first location 351*c* and crosses a second side edge 327*b* of the second elongate member 304*e* at a second location 352*c* when the structure 313 is in the deployed configuration. Electrode 306*aa* associated with transducer 306*aa* is wholly located on a portion 348*c* of the second elongate member 304*e*, the portion 348*c* located between a first transverse line 349*e* and a second transverse line 349*f* when the structure 313 is in the deployed configuration. The first transverse line 349*e* extends across a first width 353*e* of the second elongate member 304*e* at the first location 351*c*, and the second transverse line 349*f* extends across a second width 353*f* of the second elongate member 304*e* at the second location 352*c*. In this particular embodiment, the first width 353*e* is smaller than the second width 353*f*.

In a manner similar to embodiments associated with FIGS. 3A, 3B, 3C, 3D and 3E, electrically conductive surfaces (e.g., energy transmission surfaces 319) of various ones of the electrodes 315 employed in various embodiments associated with FIGS. 3F, 3G, 3H, 3I, and 3J may have different sizes or shapes. For example, referring to FIG. 3J, it is noted that each of various one of the electrodes 315 (e.g., electrodes 315*cc*, 315*dd* and 315*ee*) located on at least on elongate member 304*g* have different shapes and sizes. In at least one particular embodiment associated with FIG. 3J, a periphery of an electrically conductive surface (e.g., an energy transmission surface 319) of various ones of the electrodes 315 is defined by various electrode edges. For example, electrode 315*dd* includes a first electrode edge 333*c* and a second electrode edge 333*d* opposite across an electrically conductive surface of electrode 315*dd* from the first electrode edge 333*c*. In at least one particular embodiment, the first electrode edge 333*c* associated with electrode 315*dd* is arranged to follow a portion of the first side edge 327*a* of the overlapping elongate member 304*e* between the first location 351*b* and the second location 352*b* when the structure 313 is in an expanded or deployed configuration. In at least one particular embodiment, the first electrode edge 333*c* of electrode 315*dd* is arranged to be parallel to the portion of the first side edge 327*a* of the overlapping elongate member 304*e* between the first location 351*b* and the second location 352*b* when the structure 313 is in an expanded or deployed configuration. In at least one particular embodiment, the first electrode edge 333*c* of electrode 315*dd* is arranged to follow a portion of the first side edge 327*a* that defines or forms part of, the recessed portion 328*c* of overlapping elongate member 304*e* in the expanded or deployed configuration. In at least one particular embodiment, the second electrode edge 333*d* associated with electrode 315*dd* is arranged to follow a portion of one of the side edges 327 of elongate member 304*g* (e.g., side edge 327*a* of second elongate member 304*g*). In at least one particular embodiment, the second electrode edge 333*d* associated with electrode 315*dd* is arranged to follow a portion of one of the side edges 327 of elongate member 304*g* (e.g., side edge 327*a* of second elongate member 304*g*) that defines, or forms part of, a recessed portion 328*j* of the elongate member 304*g*. In at least one particular embodiment, a first part of a first electrode edge 333*e* associated with electrode 315*ee* located on elongate member 304*g* is arranged to follow a portion of the first side edge 327*a* that defines, or forms part of, the recessed portion 328*c* of overlapping elongate member 304*e* when structure 313 is in the deployed configuration, and a second part of the first electrode edge 333*e* of electrode 315*ee* is arranged to follow a portion of the first side edge 327*a* that does not define or form part of the recessed portion 328*c* of overlapping elongate member 304*e* when structure 313 is in an expanded or deployed configuration. In at least one particular embodiment, a first part of a second electrode edge 333*f* associated with electrode 315*ee* is arranged to follow a portion of the first side edge 327*a* that defines, or forms part of, the recessed portion 328*j* of the elongate member 304*g*, and a second part of the second electrode edge 333*f* is arranged to follow a portion of the first side edge 327*a* of elongate member 304*j* that does not define, or form part of, the recessed portion 328*j*.

In at least one particular embodiment associated with FIGS. 3F, 3G, 3H, and 3I, the edge 327*a* of the first elongate member 304*d* is interrupted by a notch 330*a*. Similarly, in some embodiments, the edge 327*a* of the first elongate member 304*d* is interrupted by recessed portion 328*a* of the first elongate member 304*d*. In some embodiments, the recessed portion 328*a* forms at least a portion of the notch 330*a*. In this particular illustrated embodiment, notch 330*a* is located in the intermediate portion 309 of the first elongate member 304*d* and extends towards the second edge 327*b*. In a similar fashion, the recessed portions 328*b*, 328*c* and 328*d* may form a portion of a respective one of notches 330*b*, 330*c* and 330*d* (called out in FIG. 3H) in various embodiments. In various embodiments associated with FIGS. 3F, 3G, 3H, 3I and 3J, various ones of the recessed portions 328 may be advantageously employed to create, at least in part, a spatial distribution of the transducers 315 having a relatively high spatial density. In various embodiments associated with FIGS. 3F, 3G, 3H, 3I and 3J, various ones of recessed portions 328 may be advantageously employed to address, at least in part, transducer size or shape constraints associated with structure 313 (e.g., overlapping regions of elongate members 304 or varying distances between various elongate members 304). In various embodiments associated with FIGS. 3F, 3G, 3H, 3I and 3J, various ones of recessed portions 328 may allow, at least in part, for the use of electrodes 315 having relatively large electrically conductive surfaces (e.g., energy transmission surfaces 319). Other benefits may accompany the use of recessed portions such as recessed portions 328. For example, in some embodiments, recessed portions similar to various ones of recess portions 328 may be employed to increase fluid flow (e.g., blood flow) in a particular region of structure 313 (e.g., a region where elongate members 304 overlap one another) that may hinder or otherwise obstruct a flow of fluid (e.g., blood flow).

In other embodiments, various ones of the recessed portions 328 may take a form other than a notch (e.g., notch 330*a*). For example, FIG. 3K includes a perspective view of two elongate members 304*h* and 304*i* in a flattened configuration similar to that shown by elongate members 304*d* and 304*e* in FIG. 3H. Elongate members 304*h* and 304*i* are similar to elongate members 304*d* and 304*e* in various embodiments, form part of structure of a transducer-based device system (not shown) similar to structures 308, 313. In some of these various embodiments, the structure may be configurable between a delivery configuration and a deployed configuration similar to that previously described in this detailed description. In some of these various embodiments, elongate member 304*h* overlaps elongate member 304*i* when the structure is the deployed configuration in a manner similar to elongate members 304*d* and 304*e*. For convenience of discussion, various elements of each of elongate members 304*h* and 304*i* are identified by the same part numbers employed to identify similar elements in other previously described elongate members. In some embodiments, each of elongate members 304*h* and 304*i* includes an intermediate portion 309 that includes a front surface 318*a* and back surface 318*b* opposite across a thickness 318*c* of the elongate member. In some embodiments, at least some of the transducers 306/electrodes 315 are located on the front surfaces 318*a*. Each intermediate portion 309 includes a respective pair of side edges 327*a*, 327*b* extending between proximal and distal ends 307, 305 of the elongate member 304. In a manner similar to that shown in FIGS. 3F, 3G, and 3I the first elongate member 304*h* may be positioned such that first edge 327*a* of the first elongate member 304*h* crosses a second edge 327*b* of the second elongate member 304*i* when the associated structure is in the deployed configuration. In a manner similar to elongate members 304*d*, 304*e*, each of the elongate members 304*h*, 304*i* includes a set of recessed portions 328 (e.g., associated ones of recessed portions 328*e*, 328*f*, 328*g*, 328*h*). In some embodiments, each of the elongate members 304*h*, 304*i* includes a jogged portion (e.g., a respective one of jogged portions 331*a*, 331*b*), each jogged portion undergoing at least one change in direction as the jogged portion extends between the proximal and distal ends 307, 305 of the respective elongate member. In various embodiments, various ones of the recessed portions 328*e*, 328*f*, 328*g* and 328*h* may form a part of one of the jogged portions 331*a*, 331*b*. In various embodiments, various ones of the recessed portions 328*e*, 328*f*, 328*g* and 328*h* may be located on respective ones of the elongate members 304*h* and 304*i* to expose a portion of at least one transducer 306/electrode 315 located on another elongate member 304 (e.g., when an associated structure that includes the elongate members 304 is in a deployed configuration). In other example embodiments, a surface of a particular one of the elongate members may be interrupted by a channel (e.g., trough, groove, aperture), the channel located to expose a portion of at least one transducer 306/electrode 315 located on another elongate member 304 especially when an associated structure that includes the elongate members 304 is in a deployed configuration.

While some of the embodiments disclosed above are described with examples of cardiac mapping, the same or similar embodiments may be used for mapping other bodily organs, for example gastric mapping, bladder mapping, arterial mapping and mapping of any lumen or cavity into which the devices of the present invention may be introduced.

While some of the embodiments disclosed above are described with examples of cardiac ablation, the same or similar embodiments may be used for ablating other bodily organs or any lumen or cavity into which the devices of the present invention may be introduced.

Subsets or combinations of various embodiments described above can provide further embodiments.

These and other changes can be made to the invention in light of the above-detailed description. In general, in the following claims, the terms used should not be construed to limit the invention to the specific embodiments disclosed in the specification and the claims, but should be construed to include other transducer-based device systems including all medical treatment device systems and medical diagnostic device systems in accordance with the claims. Accordingly, the invention is not limited by the disclosure, but instead its scope is to be determined entirely by the following claims.

What is claimed is:

1. A medical device system comprising:
   a structure comprising a plurality of elongate members; and
   a plurality of electrodes positionable in a bodily cavity and supported by the plurality of elongate members of the structure, the plurality of elongate members including a first elongate member and a second elongate member,
   wherein the structure is selectively moveable between:
      a delivery configuration in which the structure is sized to be percutaneously deliverable to the bodily cavity, and
      a deployed configuration in which the structure is sized too large to be percutaneously deliverable to the bodily cavity, and in which a first portion of the first elongate member is in an at least partially overlapping relationship with a first portion of the second elongate member,
   wherein a first group of electrodes of the plurality of electrodes is arranged in a first ringed arrangement about an axis of the structure in a state in which the structure is in the deployed configuration,
   wherein the first group of electrodes comprises a first electrode supported by the first portion of the first elongate member and comprises a second electrode supported by the first portion of the second elongate member, the first electrode including an exterior surface having a different size, shape, or both size and shape than a corresponding exterior surface of the second electrode, such that the first ringed arrangement in which the first group of electrodes is arranged comprises electrodes including exterior surfaces having different sizes, shapes, or both sizes and shapes,
   wherein the different size, shape, or both size and shape of the exterior surface of the first electrode compared to the corresponding exterior surface of the second electrode is or are configured to accommodate the at least partially overlapping relationship between the first portion of the first elongate member and the first portion of the second elongate member, and
   wherein each electrode of at least one electrode in the first group of electrodes is configured to selectively transmit energy from the exterior surface of the electrode, the energy sufficient to ablate tissue.

2. The medical device system of claim 1,
   wherein an elongate member of the plurality of elongate members includes a proximal end portion and a distal end portion,
   wherein, in a state in which the structure is in the delivery configuration, the elongate member is configured to cause the distal end portion of the elongate member to be deliverable ahead of the proximal end portion of the elongate member to the bodily cavity,
   wherein, in the state in which the structure is in the deployed configuration, the distal end portion of the elongate member is positioned at least proximate the proximal end portion of the elongate member, and
   wherein, at least one electrode in the first group of electrodes is or are supported by the elongate member.

3. The medical device system of claim 2, wherein at least two electrodes of the plurality of electrodes including exterior surfaces having different sizes, shapes, or both sizes and shapes are supported on the elongate member.

4. The medical device system of claim 1,
wherein an elongate member of the plurality of elongate members includes a proximal end portion and a distal end portion,
wherein, in a state in which the structure is in the delivery configuration, the elongate member is configured to cause the distal end portion of the elongate member to be deliverable ahead of the proximal end portion of the elongate member to the bodily cavity,
wherein, in the state in which the structure is in the deployed configuration, the distal end portion of the elongate member is positioned at least proximate the proximal end portion of the elongate member, and
wherein at least two electrodes of the plurality of electrodes including exterior surfaces having different sizes, shapes, or both sizes and shapes are supported by the elongate member.

5. The medical device system of claim 1,
wherein at least a portion of an elongate member of the plurality of elongate members comprises a coiled profile in the state in which the structure is in the deployed configuration, and
wherein at least one electrode in the first group of electrodes is or are supported by the at least the portion of the elongate member.

6. The medical device system of claim 1,
wherein at least a portion of an elongate member of the plurality of elongate members comprises a coiled profile in the state in which the structure is in the deployed configuration, and
wherein at least two electrodes of the plurality of electrodes including exterior surfaces having different sizes, shapes, or both sizes and shapes are supported by the at least the portion of the elongate member.

7. The medical device system of claim 1,
wherein at least a portion of an elongate member of the plurality of elongate members comprises a volute-shaped profile in the state in which the structure is in the deployed configuration, and
wherein at least one electrode in the first group of electrodes is or are supported by the at least the portion of the elongate member.

8. The medical device system of claim 1, further comprising an elongated shaft member configured to percutaneously deliver the structure to the bodily cavity in a state in which the structure is in the delivery configuration, the elongated shaft member comprising a proximal end portion, a distal end portion, and an elongated portion extending between the proximal end portion of the elongated shaft member and the distal end portion of the elongated shaft member,
wherein an elongate member of the plurality of elongate members includes a proximal end portion, a distal end portion comprising a distal end, and an intermediate portion between the distal end portion of the elongate member and the proximal end portion of the elongate member, the intermediate portion located along a length of the elongate member,
wherein, in the state in which the structure is in the delivery configuration, the elongate member is configured to cause the distal end portion of the elongate member to be deliverable ahead of the proximal end portion of the elongate member to the bodily cavity,
wherein in the state in which the structure is in the deployed configuration, the elongate member comprises (a) a first portion positioned proximately to the distal end portion of the elongated shaft member, the first portion of the elongate member bending away from the distal end portion of the elongated shaft member, and (b) a loop-shaped second portion positioned along the length of the elongate member closer toward the distal end of the elongate member than the first portion of the elongate member, and
wherein at least one electrode in the first group of electrodes is or are supported by the loop-shaped second portion of the elongate member.

9. The medical device system of claim 8, wherein the loop-shaped second portion of the elongate member comprises a region skewed with respect to the distal end portion of the elongated shaft member in the state in which the structure is in the deployed configuration.

10. The medical device system of claim 8, wherein the loop-shaped second portion of the elongate member comprises a region transverse with respect to the distal end portion of the elongated shaft member.

11. The medical device system of claim 8, wherein the axis of the structure is configured to avoid intersecting the distal end portion of the elongated shaft member at least in the state in which the structure is in the deployed configuration.

12. The medical device system of claim 1, further comprising an elongated shaft member configured to percutaneously deliver the structure to the bodily cavity in a state in which the structure is in the delivery configuration, the elongated shaft member comprising a proximal end portion, a distal end portion, and an elongated portion extending between the proximal end portion of the elongated shaft member and the distal end portion of the elongated shaft member,
wherein an elongate member of the plurality of elongate members includes a proximal end portion, a distal end portion comprising a distal end, and an intermediate portion between the distal end portion of the elongate member and the proximal end portion of the elongate member, the intermediate portion located along a length of the elongate member,
wherein, in the state in which the structure is in the delivery configuration, the elongate member is configured to cause the distal end portion of the elongate member to be deliverable ahead of the proximal end portion of the elongate member to the bodily cavity,
wherein in the state in which the structure is in the deployed configuration, the elongate member comprises (a) a first portion positioned proximately to the distal end portion of the elongated shaft member, the first portion of the elongate member bending away from the distal end portion of the elongated shaft member, and (b) a loop-shaped second portion positioned along the length of the elongate member closer toward the distal end of the elongate member than the first portion of the elongate member, and
wherein at least two electrodes of the plurality of electrodes including exterior surfaces having different sizes, shapes, or both sizes and shapes are supported by the at least the loop-shaped second portion of the elongate member.

13. The medical device system of claim 1, wherein a second group of electrodes of the plurality of electrodes is arranged in a second ringed arrangement about the axis of the structure in the state in which the structure is in the deployed configuration.

14. The medical device system of claim 13, wherein the second group of electrodes of the plurality of electrodes comprises a third electrode, the third electrode including an exterior surface having a different size, shape, or both size and shape than each of (i) a corresponding exterior surface of the first electrode, and (ii) the corresponding exterior surface of the second electrode.

15. The medical device system of claim 13, wherein the second group of electrodes of the plurality of electrodes comprises a third electrode and a fourth electrode, the third electrode including an exterior surface having a different size, shape, or both size and shape than a corresponding exterior surface of the fourth electrode, such that the second ringed arrangement in which the second group of electrodes is arranged comprises electrodes including exterior surfaces having different sizes, shapes, or both sizes and shapes.

16. The medical device system of claim 15, wherein the exterior surfaces of the first electrode, the second electrode, and the third electrode have different sizes, shapes, or both sizes and shapes from one another.

17. The medical device system of claim 15, wherein the exterior surfaces of the first electrode, the second electrode, the third electrode, and the fourth electrode have different sizes, shapes, or both sizes and shapes from one another.

18. The medical device system of claim 13, wherein each electrode in the second group of electrodes includes a respective exterior surface, and wherein the respective exterior surfaces of all the electrodes in the second group have a same shape.

19. The medical device system of claim 13, wherein the first ringed arrangement and the second ringed arrangement are concentrically arranged about the axis of the structure in the state in which the structure is in the deployed configuration.

20. The medical device system of claim 1, wherein the structure forms part of a basket catheter.

21. The medical device system of claim 1, wherein the structure forms part of a balloon catheter.

22. The medical device system of claim 1, wherein the energy is radio-frequency (RF) energy.

23. The medical device system of claim 1, wherein the plurality of electrodes includes a plurality of electrode sets, each electrode set of the plurality of electrode sets supported by a respective elongate member of the plurality of elongate members.

24. The medical device system of claim 1, wherein each electrode in the first group of electrodes is configured to selectively transmit energy from the exterior surface of the electrode, the energy sufficient to ablate tissue.

25. A catheter device system comprising:
an elongated catheter member including a proximal end portion, a distal end portion comprising a distal end, and an elongated portion between the distal end portion of the elongated catheter member and the proximal end portion of the elongated catheter member, the elongated portion located along a length of the elongated catheter member, the elongated catheter member selectively moveable between:
a delivery configuration in which at least the distal end portion of the elongated catheter member is sized to be percutaneously deliverable to a bodily cavity, the elongated catheter member configured to cause the distal end portion of the elongated catheter member to be deliverable ahead of the elongated portion of the elongated catheter member to the bodily cavity in a state in which the elongated catheter member is in the delivery configuration, and
a deployed configuration in which at least the distal end portion of the elongated catheter member is sized too large to be percutaneously deliverable to the bodily cavity; and
a plurality of electrodes positionable in the bodily cavity, each electrode of the plurality of electrodes comprising a respective external energy transmission surface,
wherein each electrode of at least one electrode of the plurality of electrodes is configured to selectively transmit energy from the external energy transmission surface of the electrode, the energy sufficient to ablate tissue,
wherein, in a state in which the elongated catheter member is in the deployed configuration, the distal end portion of the elongated catheter member comprises (a) a first portion bending away from the elongated portion of the elongated catheter member, and (b) a loop-shaped second portion positioned along the length of the elongated catheter member closer toward the distal end of the distal end portion of the elongated catheter member than the first portion of the distal end portion of the elongated catheter member, the plurality of electrodes located on the loop-shaped second portion of the distal end portion of the elongated catheter member,
wherein, in the state in which the elongated catheter member is in the deployed configuration, a first portion of the loop-shaped second portion of the distal end portion of the elongated catheter member is in an at least partially overlapping relationship with a second portion of the loop-shaped second portion of the distal end portion of the elongated catheter member,
wherein the plurality of electrodes comprises a first electrode and a second electrode, the external energy transmission surface of the first electrode having a different size, shape, or both size and shape than the corresponding external energy transmission surface of the second electrode, such that the plurality of electrodes include external energy transmission surfaces having different sizes, shapes, or both sizes and shapes, and
wherein the different size, shape, or both size and shape of the external energy transmission surface of the first electrode compared to the corresponding external energy transmission surface of the second electrode is or are configured to accommodate the at least partially overlapping relationship between the first portion of the loop-shaped second portion of the distal end portion of the elongated catheter member and the second portion of the loop-shaped second portion of the distal end portion of the elongated catheter member.

26. The catheter device system of claim 25, wherein the loop-shaped second portion comprises a coiled profile in the state in which the elongated catheter member is in the deployed configuration.

27. The catheter device system of claim 25, wherein the loop-shaped second portion comprises a volute-shaped profile in the state in which the elongated catheter member is in the deployed configuration.

28. The catheter device system of claim 25, wherein the first portion comprises a region skewed with respect to the elongated portion in the state in which the elongated catheter member is in the deployed configuration.

29. The catheter device system of claim 25, wherein the first portion comprises a region transverse with respect to the elongated portion in the state in which the elongated catheter member is in the deployed configuration.

30. The catheter device system of claim 25, wherein the plurality of electrodes is arranged in a first ringed arrangement in the state in which the elongated catheter member is in the deployed configuration.

31. The catheter device system of claim 30, wherein the plurality of electrodes is a first plurality of electrodes, and wherein the catheter device system comprises a second plurality of electrodes other than the first plurality of electrodes, the second plurality of electrodes arranged in a second ringed arrangement in the state in which the elongated catheter member is in the deployed configuration.

32. The catheter device system of claim 31, wherein each electrode of the second plurality of electrodes comprises a respective external energy transmission surface, and wherein each electrode of the second plurality of electrodes is configured to selectively transmit energy from the external energy transmission surface of the electrode, the energy sufficient to ablate tissue.

33. The catheter device system of claim 31, wherein each electrode of the second plurality of electrodes comprises a respective external energy transmission surface, the second plurality of electrodes comprising a third electrode, the external energy transmission surface of the third electrode having a different size, shape, or both size and shape than the corresponding external energy transmission surface of (a) the first electrode of the first plurality of electrodes, (b) the second electrode of the first plurality of electrodes, or each of (a) and (b).

34. The catheter device system of claim 31, wherein each electrode of the second plurality of electrodes comprises a respective external energy transmission surface, the second plurality of electrodes comprising a third electrode and a fourth electrode, the external energy transmission surface of the third electrode having a different size, shape, or both size and shape than the corresponding external energy transmission surface of the fourth electrode, such that the second plurality of electrodes include external energy transmission surfaces having different sizes, shapes, or both sizes and shapes.

35. The catheter device system of claim 34, wherein the external energy transmission surfaces of the first electrode, the second electrode, the third electrode, and the fourth electrode have different sizes, shapes, or both sizes and shapes from one another.

36. The catheter device system of claim 31, wherein the second plurality of electrodes are located on the distal end portion.

37. The catheter device system of claim 25, wherein the distal end portion forms part of a basket catheter.

38. The catheter device system of claim 25, wherein the distal end portion forms part of a balloon catheter.

39. The catheter device system of claim 25, wherein the energy is radio-frequency (RF) energy.

40. The catheter device system of claim 25, wherein each electrode of the plurality of electrodes is configured to selectively transmit energy from the external energy transmission surface of the electrode, the energy sufficient to ablate tissue.

* * * * *